(12) United States Patent
Hosoya et al.

(10) Patent No.: US 9,422,294 B2
(45) Date of Patent: Aug. 23, 2016

(54) CYCLIC COMPOUND, METHOD FOR PRODUCING CYCLIC COMPOUND, AND METHOD FOR MODIFYING BIOLOGICAL MOLECULE

(71) Applicant: JNC CORPORATION, Tokyo (JP)

(72) Inventors: Takamitsu Hosoya, Tokyo (JP); Isao Kii, Kyoto (JP); Suguru Yoshida, Tokyo (JP); Takeshi Matsushita, Chiba (JP)

(73) Assignee: JNC CORPORATION, Tokyo (JP)

( * ) Notice: Subject to any disclaimer, the term of this patent is extended or adjusted under 35 U.S.C. 154(b) by 0 days.

(21) Appl. No.: 14/338,829

(22) Filed: Jul. 23, 2014

(65) Prior Publication Data

US 2014/0364594 A1 Dec. 11, 2014

Related U.S. Application Data

(62) Division of application No. 13/634,263, filed as application No. PCT/JP2011/055548 on Mar. 9, 2011, now Pat. No. 8,901,312.

(30) Foreign Application Priority Data

Mar. 26, 2010 (JP) ................. 2010-073429

(51) Int. Cl.
*C07D 487/04* (2006.01)
*C07K 1/107* (2006.01)
*C07D 249/04* (2006.01)

(52) U.S. Cl.
CPC ............ *C07D 487/04* (2013.01); *C07K 1/1077* (2013.01); *C07D 249/04* (2013.01)

(58) Field of Classification Search
CPC .................................................. C07D 249/04
See application file for complete search history.

(56) References Cited

FOREIGN PATENT DOCUMENTS

WO    WO-2009067663 A1    5/2009

OTHER PUBLICATIONS

Prescher, et al., "Chemical remodeling of cell surfaces in living animals", Nature, Aug. 19, 2004, vol. 430, pp. 873-877.
Gribanova, 2009, Doklady Chemistry, vol. 426, part 1, p. 105-110.
International Search Report dated Apr. 26, 2011 issued in PCT Application No. PCT/JP2011/055548.
Agard, et al., "A Strain-Promoted [3+2] Azide-Alkyne Cycloaddition for Covalent Modification of Biomolecules in Living Systems", Journal of American Chemical Society, 2004, Vo.. 126, pp. 15046-15047.
Ning, et al., "Visualizing Metabolically Labeled Glycoconjugates of Living Cells by Copper-Free and Fast Huisgen Cycloadditions", Angewandte Chemie, 2008, vol. 47, pp. 2253-2255.
Lutz, "Copper-Free Azide-Alkyne Cycloadditions: New Insights of Perspectives", Angewandte Chemie, 2008, vol. 47, pp. 2182-2184.
Agard, et al., "A Comparative Study of Bioorthogonal Reactions with Azides", ACS Chemical Biology, 2006, Vo. 1, pp. 644-648.
Codelli, et al., "Second-Generation Difluorinated Cyclooctynes for Copper-Free Click Chemistry", Journal of American Chemical Society, 2008, vol. 130, pp. 11486-11493.
Sirivolu, et al., "DNA with Branched Internal Side Chains: Synthesis of 5-Tripropargylamine-dU and Conjugation by an Azide-Alkyne Double Click Reaction", ChemBioChem, 2008, vol. 9, pp. 2305-2316.
Godeau, et al., "Glycosyl-Nucleoside Lipids as Low-Molecular-Weight Gelators", Langmiur, 2009, vol. 25, pp. 8447-8450.
Seela, et al., "'Double-Click' Reaction on 7-Deazaguanine DNA: Synthesis and Excimer Fluorescence of Nucleosides and Oligonucleotides with Branched Side Chains Decorated with Proximal Pyrenes", Journal of Organic Chemistry, 2010, vol. 75, pp. 284-295.
Kii, et al., "Strain-promoted double-click reaction for chemical modification of azido-biomolecules", Organic & Biomolecular Chemistry, Sep. 21, 2010, vol. 8, pp. 4051-4055.
Saxon, et al., "Cell Surface Engineering by a Modified Staudinger Reaction", Science, Mar. 17, 2000, 287, pp. 2007-2010.
Laughlin, et al., "In Vivo Imaging of Membrane-Associated Glycans in Developing Zebrafish", Science, 2008, 320, 664-667.
Kiick, et al., "Incorporation of azides into recombinant proteins for chemoselective modification by the Staudinger ligation", Proc. Natl. Acad. Sci. USA, Jan. 8, 2002, vol. 99, pp. 19-24.
Poloukhtine, et al., "Selective Labeling of Living Cells by a Photo-Triggered Click Reaction", J. Am. Chem. Soc., 2009, 131, pp. 15769-15776.
Baskin, et al., "Copper-Free click chemistry for dynamic in vivo imaging", Proc. Natl. Acad. Sci. USA, Oct. 23, 2007, vol. 104, pp. 16793-16797.
Laughlin, et al., "In Vivo Imaging of *Caenorhabditis elegans* Glycans", ACS Chem. Biol., 2009, vol. 4, pp. 1068-1072.
Debets, et al., "Aza-dibenzocyclooctynes for fast and efficient enzyme PEGylation via copper-free (3+2) cycloaddition", Chem Commun, 2010, 46, pp. 97-99.
Chang, et al., Copper-free click chemistry in living animals, Proc. Natl. Acad. Sci. USA, 2010, 107, 1821-1826.

*Primary Examiner* — Michael Barker
*Assistant Examiner* — Karen Cheng
(74) *Attorney, Agent, or Firm* — Drinker Biddle & Reath LLP

(57) ABSTRACT

The invention aims in establishing a method for modifying biomolecules using a reaction that efficiently modifies biomolecules and is widely applicable. The invention thus provides a cyclic compound containing two triazole rings formed by adding and ligating an azide compound possessing an azido group to each of the two carbon-carbon triple bond sites of an eight-membered cyclic skeleton of a cyclic diyne compound by a double click reaction; a method for producing a cyclic compound using a double click reaction; and a method for modifying biomolecules.

5 Claims, 7 Drawing Sheets

FIG. 9

CYCLIC COMPOUND, METHOD FOR PRODUCING CYCLIC COMPOUND, AND METHOD FOR MODIFYING BIOLOGICAL MOLECULE

CROSS REFERENCE TO RELATED APPLICATIONS

This application is a divisional application of co-pending application Ser. No. 13/634,263, filed Sep. 26, 2012, which is the National Stage of International Application No. PCT/JP2011/055548, filed Mar. 9, 2011, and claims benefit of Japanese Application No. 2010-073429, filed Mar. 26, 2010.

TECHNICAL FIELD

The present invention relates to a cyclic compound, a method for producing the cyclic compound by a strain-promoted double-click reaction, and a method for modifying biomolecules.

BACKGROUND ART

Chemical modification of biomolecules is performed to clarify the mechanism for the activity expression of biologically active substances or the function of biomolecules. There is known a method for selectively modifying glycoconjugates with fluorescent dyes, etc., which involves introducing an azido group into biomolecules, e.g., glycoconjugates at the cell membrane surface, etc. and reacting the azido group with triarylphosphines having a fluorescent functional group, etc. as a probe to ligate them through covalent bond (e.g., see Non-Patent Documents 1 to 3).

Also, a method using a single click reaction in which a single azide compound is added and ligated to an alkyne is also known. In this case, probe-bearing biomolecules can be identified by reacting the azido group introduced into the target biomolecule with an alkyne compound as a probe. As examples of the click reaction, a reaction using Cu(I) catalyst and a catalyst-free reaction are both known (e.g., see Non-Patent Documents 4 to 13).

CITATION LIST

Non Patent Literature

[Non-Patent Document 1] E. Saxon, C. R. Bertozzi, Science, 2000, 287, 2007-2010
[Non-Patent Document 2] K. L. Kiick, E. Saxon, D. A. Tirrell, C. R. Bertozzi, Proc. Natl. Acad. Sci. USA, 2002, 99, 19-24
[Non-Patent Document 3] J. A. Prescher, D. H. Dube, C. R. Bertozzi, Nature, 2004, 430, 873-877; Nicholas J. Agard, Jennifer A. Prescher, and Carolyn R Bertozzi, J. Am. Chem. Soc. 126, 15046-15047, 2004
[Non-Patent Document 4] N. J. Agard, J. A. Prescher, C. R. Bertozzi, J. Am. Chem. Soc. 2004, 126, 15046-15047
[Non-Patent Document 5] N. J. Agard, J. M. Baskin, J. A. Prescher, A. Lo, C. R. Bertozzi, ACS Chem. Biol. 2006, 1, 644-648
[Non-Patent Document 6] J. M. Baskin, J. A. Prescher, S. T. Laughlin, N. J. Agard, P. V. Chang, I. A. Miller, A. Lo, J. A. Codelli, C. R. Bertozzi, Proc. Natl. Acad. Sci. USA 2007, 104, 16793-16797
[Non-Patent Document 7] J. A. Codelli, J. M. Baskin, N. J. Agard, C. R. Bertozzi, J. Am. Chem. Soc. 2008, 130, 11486-11493
[Non-Patent Document 8] S. T. Laughlin, J. M. Baskin, S. L. Amacher, C. R. Bertozzi, Science 2008, 320, 664-667
[Non-Patent Document 9] X. Ning, J. Guo, M. A. Wolfert, G J. Boons, Angew. Chem. 2008, 120, 2285-2287; Angew. Chem. Int. Ed. 2008, 47, 2253-2255
[Non-Patent Document 10] A. A. Poloukhtine, N. E. Mbua, M. A. Wolfert, G-J. Boons, V. V. Popik, J. Am. Chem. Soc. 2009, 131, 15769-15776
[Non-Patent Document 11] S. T. Laughlin, C. R. Bertozzi, ACS Chem. Biol. 2009, 4, 1068-1072
[Non-Patent Document 12] M. F. Debets, S. S. van Berkel, S. Schoffelen, F. P. J. T. Rutjes, J. C. M. van Hest, F. L. van Delft, Chem. Commun. 2010, 46, 97-99
[Non-Patent Document 13] P. V. Chang, J. A. Prescher, E. M. Sletten, J. M. Baskin, I. A. Miller, N. J. Agard, A. Lo, C. R. Bertozzi, Proc. Natl. Acad. Sci. USA 2010, 107, 1821-1826

SUMMARY OF THE INVENTION

Technical Problem

The modification reaction between an azido group and a phosphine derivative described above requires a plurality of steps including at least a probing reaction of the phosphine derivative and a ligation reaction of the azido group and the phosphine derivative. For this reason, it is difficult to modify biomolecules efficiently. In particular, the reaction rate between the azido group and phosphine derivative is generally slow, and it is therefore more difficult to accelerate the modification reaction. Furthermore, phosphine derivatives are susceptible to oxidation and hence, biomolecules cannot always be modified with a high efficiency.

Also in the single click reaction of adding a single azide compound to an alkyne, previous probing of the alkyne molecule is required each time depending upon the purpose of experimentation. It is therefore difficult to modify biomolecules in a small number of steps. In addition, the catalyst-free single click reaction involves complicated substrate synthesis and when catalysts are used, the catalysts show cytotoxicity, and so on. Thus, the single click reaction is disadvantageous in that the reaction is not widely available to modification of biomolecules.

Under the circumstances above, there is a need for cyclic compounds obtained by a reaction for efficiently modifying biomolecules using a substrate readily available in a less number of steps, which reaction is broadly applicable, a method for producing cyclic compounds using such a reaction, and a method for modifying biomolecules.

Solution To Problem

The present inventors have found that by taking advantage of a double click reaction using highly strained diynes, biomolecules can be efficiently modified in a less number of steps and this method is broadly applicable. Based on the finding, the present invention has been accomplished. The present invention provides cyclic compounds, a method for producing cyclic compounds by the double click reaction, and a method for modifying biomolecules.

<1> A cyclic compound comprising a cyclic skeleton and two triazole rings sharing carbon-carbon double bond sites with the cyclic skeleton.

<2> The cyclic compound according to <1> above, which contains the triazole rings formed by adding and ligating an azide compound having an azido group to each of the two carbon-carbon triple bond sites on the cyclic skeleton in a cyclic diyne compound by a double click reaction.

<3> The cyclic compound according to <1> or <2> above, which contains the cyclic skeleton of an 8-membered ring.

<4> The cyclic compound according to any one of <1> to <3> above, which further contains a benzene ring and/or heteroaromatic ring sharing the carbon-carbon double bond sites with the cyclic skeleton.

<5> The cyclic compound according to any one of <1> to <4> above, which is represented by formula (1) or (2) below:

[Chemical formula (1)]

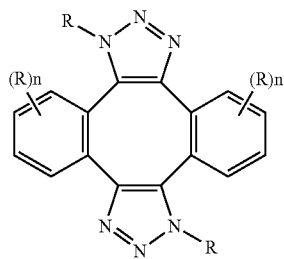

(1)

(in formula (1), each R independently represents hydrogen or a hydrocarbon group, and each n independently represents an integer of 0 to 4, preferably an integer of 0 or 1), and,

[Chemical formula (2)]

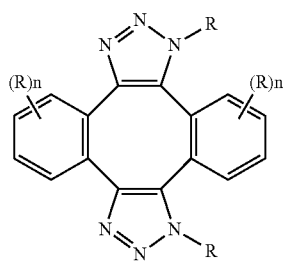

(2)

(in formula (2), each R independently represents hydrogen or a hydrocarbon group, and each n independently represents an integer of 0 to 4, preferably an integer of 0 or 1).

<6> A method for producing a cyclic compound, which comprises adding and ligating an azide compound having an azido group to each of the two carbon-carbon triple bond sites in a cyclic diyne compound by a double click reaction to produce a cyclic compound containing two triazole rings.

<7> A method for modifying a biomolecule, which comprises adding and ligating the azido group of an azide compound as a probe and the azido group incorporated into the biomolecule to each of the two carbon-carbon triple bond sites in a cyclic diyne compound by a double click reaction to produce a cyclic compound.

<8> The modifying method according to <7> above, wherein the cyclic diyne compound has an 8-membered cyclic skeleton containing two carbon-carbon triple bond sites.

<9> The modifying method according to <8> above, wherein the cyclic diyne compound further has a benzene ring and/or heteroaromatic ring sharing the carbon-carbon double bond sites with the cyclic skeleton.

<10> The modifying method according to any one of <7> to <9> above, wherein the cyclic diyne compound is represented by formula (3) below:

[Chemical formula (3)]

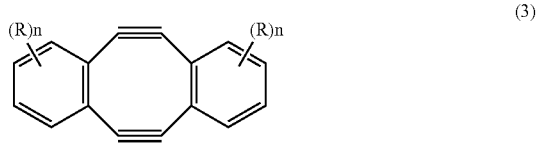

(3)

(in formula (3), each R independently represents hydrogen or a hydrocarbon group, and each n independently represents an integer of 0 to 4, preferably an integer of 0 or 1).

<11> The modifying method according to any one of <7> to <10> above, wherein the addition reaction of the azide compound and the biomolecule proceeds without using any catalyst.

<12> The modifying method according to any one of <7> to <11> above, wherein the double click reaction is performed in the co-presence of the azide compound and the biomolecule.

<13> The modifying method according to any one of <7> to <12> above, wherein the biomolecule is added to the cyclic diyne compound, the unreacted cyclic diyne compound is removed and the azide compound is added to the Advantageous Effects of Invention According to the present invention, biomolecules can be efficiently modified in a less number of steps by a double click reaction using a highly strained diyne which can be readily synthesized. In addition, the double click reaction is applicable to a variety of compounds, and such an efficient modifying method can be utilized broadly.

BRIEF DESCRIPTION OF DRAWINGS

FIG. 9 shows the results of fluorescence labeling test of glycoconjugates on the living cell surface by the SPDC reaction and the single click reaction, respectively.

DESCRIPTION OF EMBODIMENTS

Figure 1:
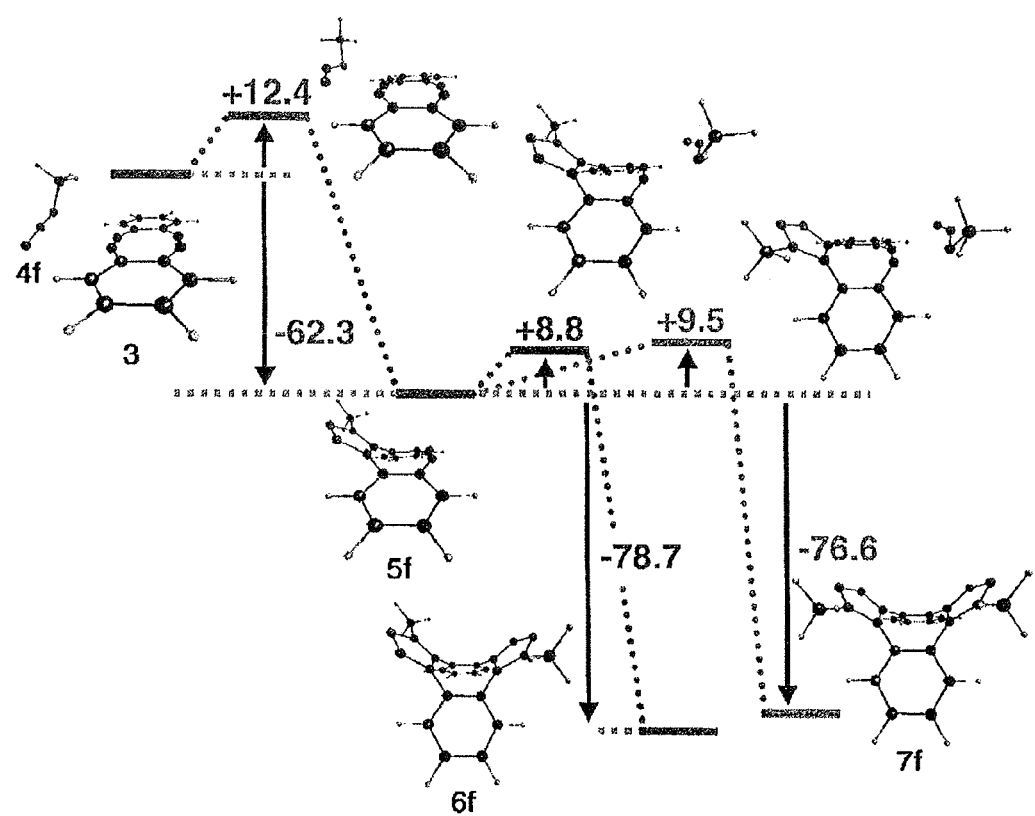
FIG. 1 shows the calculated results of activation energies and transition states in the SPDC reaction of highly strained diyne with methyl azide.

1. Cyclic Compound and Method for Producing Cyclic Compound by Double Click Reaction The cyclic compound of the present invention comprises the cyclic skeleton and two 1,2,3-triazole ring sharing the carbon-carbon double bond sites with the cyclic compound. The cyclic compound is produced via a double click reaction by adding an azide compound with an azido group to the cyclic diyne compound at each of the two carbon-carbon triple bond sites to form two 1,2,3-triazole rings which are fused rings.

1A. Double Click Reaction

The reaction of adding two azide compounds to one diyne compound so as to add the azide compounds to each of the two carbon-carbon triple bond sites of the cyclic diyne compound is called a double click reaction. In the double click reaction shown by general reaction scheme (I) below, different azide compounds can be added to the two carbon-carbon triple bond sites to ligate three molecules spontaneously.

[Reaction Scheme (I)]

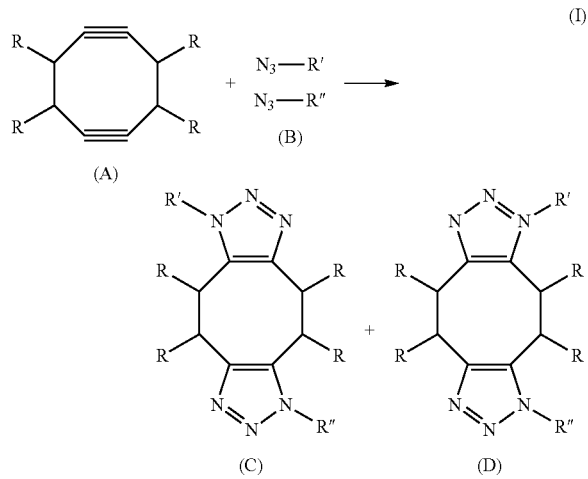

(in general scheme (I), each of R, R' and R" independently represents hydrogen or a hydrocarbon group).

An 8-membered cyclic diyne compound is used as a substrate for the double click reaction. This is because the 8-membered cyclic diyne compound is highly strained to promote the double click reaction. As such, the double click reaction in which distortion of the cyclic diyne compound promote is referred to as the SPDC reaction (Strain-Promoted Double-Click Reaction).

In the double click reaction including the SPDC reaction, an excess amount of the azide compound is used based on the diyne compound. For example, 2 to 10 equivalents, preferably 2 to 5 equivalents, more preferably 2 to 3 equivalents, of the azide compound is used based on 1 equivalent of the diyne compound.

In the double click reaction, various types of solvents can be used. That is, mainly lower alcohols such as methanol, ethanol, etc., organic solvents such as acetonitrile, tetrahydrofuran, dimethylsulfoxide, N,N-dimethylformamide, pyridine, dichloromethane, chloroform, benzene, toluene, diethyl ether, dioxan, acetone, ethyl acetate, hexane, etc., water or a buffer aqueous solution of appropriate pH, a solvent mixture thereof, can be used, as long as the azide compounds and cyclic diyne compounds are suitably soluble therein.

The double click reaction is promoted by distortion of the cyclic diyne compound and proceeds under relatively mild conditions. More specifically, the double click reaction can be performed around room temperature in the absence of a catalyst, e.g., a copper catalyst used to expedite the double click reaction. In this regard, however, heating may be performed, if necessary, by elevating to approximately 150° C. or by using a suitable solvent, the reaction may also be performed under low temperature conditions of approximately −100° C. The reaction time for the double click reaction may vary depending upon substrate and its concentration or reaction solvent, etc. but generally ranges approximately from one minute to one day, normally approximately from 10 minutes to 2 hours.

1B. Cyclic Diyne Compound ((A) in General Scheme (I) Described Above)

Preferably, the cyclic diyne compound is strained and furthermore a reasonable stability is required. Therefore, at least an 8-membered cyclic diyne compound is more preferred than unstable cyclic diyne compounds having a 7-membered ring or less. In particular, the cyclic diyne compound having an 8-membered cyclic skeleton is desired. The cyclic diyne compound which can be used further includes a heterocyclic compound containing oxygen, nitrogen, sulfur, etc.

Cyclic triyne compounds, cyclic tetrayne compounds and cyclic compounds having a larger number of the carbon-carbon triple bonds can also be used for the double click reaction, triple click reaction, quadruple click reaction, and so on, as far as they can be present stably. In the cyclic skeleton having, e.g., a 9-membered ring, triyne and tetrayne compounds can be present stably.

In the cyclic diyne compound, it is preferred to have a cyclic skeleton having preferably an 8-membered ring containing two carbon-carbon triple bonds and a benzene ring, etc. sharing the carbon-carbon double bond sites with the cyclic skeleton described above. This is because the cyclic diyne compound can attain its planarity due to such a benzene to provide a good reactivity with an azide which is a 1,3-dipolar compound. The cyclic diyne compound preferably contains two benzene rings. In addition to the benzene ring, the following cyclic diyne compounds can also be used in the double click reaction (SPDC reaction); a benzene ring which is substituted with a hydrocarbon group, etc.; a heteroaromatic ring including a pyridine ring, a pyrimidine ring, a pyrazine ring, a furan ring, a thiophene ring, a pyrrole ring, an imidazole ring, a triazole ring, an oxazole ring, a thiazole ring, etc., which may be substituted; a polycyclic type diyne compound formed by fusing a plurality of these heteroaromatic rings including a naphthalene ring, an anthracene ring, a quinoline ring, an isoquinoline ring, a quinoxaline ring, a benzofuran ring, a benzothiophene ring, an indole ring, a benzimidazole ring, etc. The aromatic rings described above may also be combined and provided for use, for example, as a cyclic diyne compound having each one of these aromatic rings.

The substituent (R in general scheme (I) described above) contained in the cyclic diyne compound includes a hydrocarbon group such as a C1-10 alkyl group (methyl, ethyl, propyl, etc.), a C2-10 alkenyl group (ethenyl, 1-propenyl, 2-propenyl, etc.), a C2-10 alkynyl group (ethynyl, 1-propynyl, 2-propynyl, etc.), a C3-10 cycloalkyl group (cyclopropyl, cyclobutyl, cyclopentyl, etc.), a C3-10 cycloalkenyl 85137356.2 group (2-cyclopenten-1-yl, 3-cyclopenten-1-yl, 2-cyclohexen-1-yl, etc.), a C4-10 cycloalkadienyl group (2,4-cyclopentadien-1-yl, 2,4-cyclohexadien-1-yl, 2,5-cyclohexadien-1-yl, etc.), a C6-14 aryl group (phenyl, naphthyl, anthryl, etc.), a C7-13 aralkyl group (benzyl, phenethyl, naphthylmethyl, etc.), a C8-13 arylalkenyl group (styryl, etc.), a C3-10 cycloalkyl-C1-6 alkyl group (cyclohexylmethyl, etc.), etc.; hydroxy group, a C1-10 alkoxyl group, a C1-10 alkoxycarbonyl group, thiol group, a C1-10 alkylthio group, amino group, a di- or mono-C1-10 alkylamino group, carboxyl group, amido group, thioamido group, thiol group, ether group, ester group, sulfo group, sulfonamido group and a halogen; a substituted or unsubstituted heteroaromatic ring such as a pyridine ring, a pyrimidine ring, a pyrazine ring, a furan ring, a thiophene ring, a pyrrole ring, an imidazole ring, a triazole ring, an oxazole ring, a thiazole ring, etc.; a polycyclic ring system formed by a plurality of the heteroaromatic rings described above and a C6-14 aryl group, etc.; a substituent containing at least one of halogen, nitrogen, oxygen, sulfur, etc. in one of the substituents above; a substituent(s) further containing at least one of hydroxy group, amino group, carboxyl group, amido group, thioamido group, thiol group, ether group, ester group, sulfo group, sulfonamido group, etc. in one of the substituents above; etc. Among them, preferred examples of the substituent R are a hydrocarbon group including a C1-10 alkyl group (methyl, ethyl, propyl, etc.), a C2-10 alkenyl group (ethenyl, 1-propenyl, 2-propenyl, etc.), a C2-10 alkynyl group (ethynyl, 1-propynyl, 2-propynyl, etc.), a C3-10 cycloalkyl group (cyclopropyl, cyclobutyl, cyclopentyl, etc.), a C3-10 cycloalkenyl group (2-cyclopenten-1-yl, 3-cyclopenten-1-yl, 2-cyclohexen-1-yl, etc.), a C4-10 cycloalkadienyl group (2,4-cyclopentadien-1-yl, 2,4-cyclohexadien-1-yl, 2,5-cyclohexadien-1-yl, etc.), a C6-14 aryl group (phenyl, naphthyl, anthryl, etc.), a C7-13 aralkyl group (benzyl, phenethyl, naphthylmethyl, etc.), a C8-13 arylalkenyl group (styryl, etc.), a C3-10 cycloalkyl-C1-6 alkyl group (cyclohexylmethyl, etc.), etc. More preferred examples of the substituent R are a C1-10 alkyl group (methyl, ethyl, propyl, etc.), a C2-10 alkenyl group (ethenyl, 1-propenyl, 2-propenyl, etc.), a C2-10 alkynyl group (ethynyl, 1-propynyl, 2-propynyl, etc.), a C3-10 cycloalkyl group (cyclopropyl, cyclobutyl, cyclopentyl, etc.), a C3-10 cycloalkenyl group (2-cyclopenten-1-yl, 3-cyclopenten-1-yl, 2-cyclohexen-1-yl, etc.) and a C4-10 cycloalkadienyl group (2,4-cyclopentadien-1-yl, 2,4-cyclohexadien-1-yl, 2,5-cyclohexadien-1-yl, etc.). In these substituents, the carbon number is generally preferably within the range described above to avoid steric hindrance that might prevent the addition reaction of an azido molecule. The substituent(s) described above is/are bound to the cyclic diyne compound, either via a C1-10 alkyl linker, etc. containing, e.g., a single or plurality of oxygen atoms, amido bonds or ester bonds, or directly.

Based on the foregoing, preferred examples of the cyclic diyne compound as the substrate for the strain-promoted double click reaction (SPDC reaction) are sym-dibenzo-1,5-cyclooctadiene-3,7-diyne(5,6,11,12-tetrahydrodibenzo[a,e]cyclooctene), 5,6,11,12-tetrahydro-1,4,7,10-tetramethyldibenzo[a,e]cyclooctene, 5,6,11,12-tetrahydro-2,3,8,9-tetramethoxydibenzo[a,e]cyclooctene,1,7-dibutyl-5,6,11,12-tetrahydrodibenzo[a,e]cyclooctene, 6,7,14,15-tetrahydrocycloocta[1,2-b:5,6-b']dinaphthalene, etc., and more preferably, the cyclic diyne compound is, e.g., sym-dibenzo-1,5-cyclooctadiene-3,7-diyne(5,6,11,12-tetrahydrodibenzo[a,e]cyclooctene).

1C. Azide Compound ((B) in general scheme (I) above)

Almost all organic azide compounds are usable as the azide compounds for the double click reaction, since organic azide compounds are generally reactive with diynes. In addition to the aromatic azides, aliphatic azides, azido sugars and azido proteins used as the azide compounds in EXAMPLES later described, there may also be used, for example, azido-amino acids, azido-peptides, azido-nucleic acids, azido-lipids, etc.

The azide compound contains as the substituents (R' and R" in general scheme (I) above) a hydrocarbon group such as a C1-10 alkyl group (methyl, ethyl, propyl, etc.), a C2-10 alkenyl group (ethenyl, 1-propenyl, 2-propenyl, etc.), a C2-10 alkynyl group (ethynyl, 1-propynyl, 2-propynyl, etc.), a C3-10 cycloallcyl group (cyclopropyl, cyclobutyl, cyclopentyl, etc.), a C3-10 cycloalkenyl group (2-cyclopenten-1-yl, 3-cyclopenten-1-yl, 2-cyclohexen-1-yl, etc.), a C4-10 cycloallcadienyl group (2,4-cyclopentadien-1-yl, 2,4-cyclohexadien-1-yl, 2,5-cyclohexadien-1-yl, etc.), a C6-14 aryl group (phenyl, naphthyl, anthryl, etc.), a C7-13 aralkyl group (benzyl, phenethyl, naphthylmethyl, etc.), a C8-13 arylalkenyl group (styryl, etc.), a C3-10 cycloalkyl-C1-6 alkyl group (cyclohexylmethyl, etc.), etc.; a substituted heteroaromatic ring including a pyridine ring, a pyrimidine ring, a pyrazine ring, a furan ring, a thiophen ring, a pyrrole ring, an imidazole ring, a triazole ring, an oxazole ring, a thiazole ring, etc. and a polycyclic ring system formed by fusing a plurality of these heteroaromatic rings including a C6-14 aryl group; and further contains hydroxy group, amino group, carboxyl group, amido group, thioamido group, thiol group, ether group, ester group, sulfo group, sulfonamido group, etc., in these substituents. In addition to these compounds, the azide compound further includes protected or unprotected sugar derivatives, nucleic acid derivatives, lipid derivatives, amino acid or peptide derivatives, etc. In these substituents, the carbon number is generally preferably within the range described above to avoid steric hindrance that might prevent the addition to the cyclic diyne compound.

More preferably, the azide compound contains as the substituents R' and R" a hydrocarbon group such as a C1-6 alkyl group, a C2-6 alkenyl group, a C2-6 alkynyl group, a C6-10 cycloalkyl group, a C6-10 cycloalkenyl group, a C6-10 cycloalkadienyl group, a C6-12 aryl group, a C7-10 aralkyl group, a C8-10 arylalkenyl group, a C6-10 cycloalkyl-C3-6 alkyl group, etc.

Examples of these preferred azide compounds include methyl azide, ethyl azide, propyl azide, azidoacetate, azidoadamantane, phenyl azide and its derivatives, benzyl azide and its derivatives, cyclohexyl azide, etc.

More specific examples of the preferred azide compound are methyl azide, ethyl azidoacetate, 1-azidoadamantane, phenyl azide, 2-methylphenyl azide, 2-isopropylphenyl azide, 2,6-dimethylphenyl azide, 2,6-diethylphenyl azide, 2,6-diisopropylphenyl azide, 2-t-butyl-6-methylphenyl azide, 2,6-dibromophenyl azide, 4-methoxyphenyl azide, 4-trifluoromethylphenyl azide, 3,5-bis (trifluoromethyl)phenyl azide, methyl 4-(azidomethyl)benzoate, benzyl azide, 4-(azidomethyl)benzyl alcohol, etc.

1D. Cyclic Compound and Triazole Rings

As a result of the double click reaction, the cyclic compound (formulae (1) and (2) as well as (C) and (D) in general scheme (I) described above) is produced. In this cyclic compound, two triazole rings are formed by addition of the azide compounds ((B) in general scheme (I) described above). As such, the triazole rings derived from the azido groups of the azide compounds are both fused to the cyclic skeleton and share the carbon-carbon double bond sites.

The cyclic compound has the structure corresponding to the cyclic diyne compound and azide compounds employed in the double click reaction. More specifically, substituents $R^1$ and $R^2$ are introduced into the triazole rings as shown in formulae (1-1) to (2-3) described below. Furthermore, in the cyclic diyne compound used in the reaction, when the two benzene rings fused to the cyclic skeleton contain no substituent, the benzene ring in the cyclic compound contain no substituent (cf., formulae (1-1) and (2-1) described below) and when the two benzene rings contain substituents $R^3$ and $R^4$, the cyclic compound contains the corresponding substituents $R^3$ and $R^4$ as well (cf., formulae (1-2) and (2-2) described below). Each symbol n in formulae (1-2) and (2-2) described below independently represents an integer of 0 to 4. Furthermore, where rings A and B other than the benzene ring are fused to the cyclic diyne compound, the corresponding rings A and B are contained also in the cyclic compound formed (cf., formulae (1-3) and (2-3) described below).

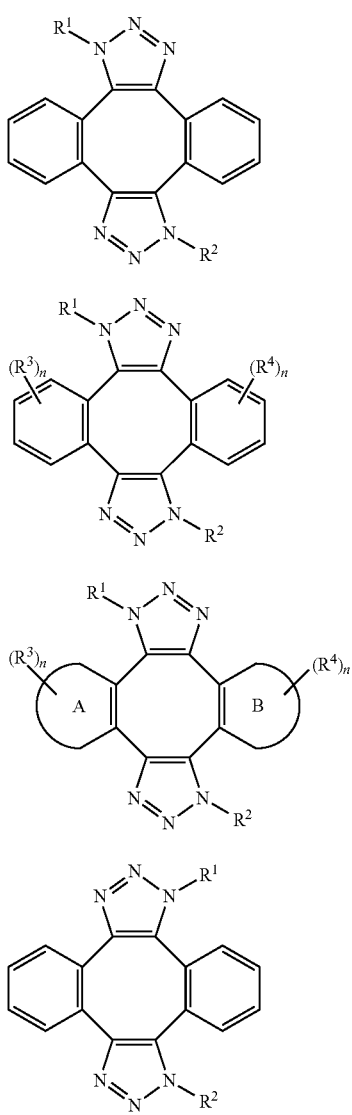

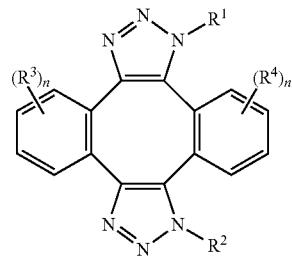

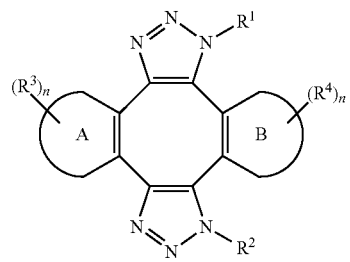

As is clear from the foregoing, both the cyclic compound containing none of the substituents $R^1$ to $R^4$ and the cyclic compound having a part or all of substituents $R^1$ to $R^4$ can be used in the double click reaction. The substituents $R^1$ and $R^2$ in formulae (1-1), (2-1), (1-2), (2-2), (1-3) and (2-3) described above are the same as R' and R" in general scheme (I) above and the substituents $R^3$ and $R^4$ are the same as R in general scheme (I).

Specific examples of preferred cyclic compounds include those formed by the double click reaction of the cyclic diyne compound with the azide compounds which are described above as being preferred. More specifically, the cyclic compounds are the following compounds, i.e.;

1,8-dihydro-1,8-dimethyldibenzo[3,4:7,8]cycloocta[1,2-d:5,6-d']bis([1,2,3]triazole),
1,10-dihydro-1,10-dimethyldibenzo[3,4:7,8]cycloocta[1,2-d:5,6-d']bis([1,2,3]triazole),
1,8-bis(ethoxycarbonylmethyl)-1,8-dihydrodibenzo[3,4:7,8]cycloocta[1,2-d:5,6-d']bis([1,2,3]triazole),
1,10-bis(ethoxycarbonylmethyl)-1,10-dihydrodibenzo[3,4:7,8]cycloocta[1,2-d:5,6-d']bis([1,2,3]triazole),
1,8-diadamantyl-1,8-dihydrodibenzo[3,4:7,8]cycloocta[1,2-d:5,6-d']bis([1,2,3]triazole),
1,10-diadamantyl-1,10-dihydrodibenzo[3,4:7,8]cycloocta[1,2-d:5,6-d']bis([1,2,3]triazole),
1,8-dihydro-1,8-diphenyldibenzo[3,4:7,8]cycloocta[1,2-d:5,6-d']bis([1,2,3]triazole),
1,10-dihydro-1,10-diphenyldibenzo[3,4:7,8]cycloocta[1,2-d:5,6-d']bis([1,2,3]triazole),
1,8-dihydro-1,8-bis(2-methylphenyl)dibenzo[3,4:7,8]cycloocta[1,2-d:5,6-d']bis([1,2,3]triazole),
1,10-dihydro-1,10-bis(2-methylphenyl)dibenzo[3,4:7,8]cycloocta[1,2-d:5,6-d']bis([1,2,3]triazole),
-1,8-dihydro-1,8-bis(2-isopropylphenyl)dibenzo[3,4:7,8]cycloocta[1,2-d:5,6-d']bis([1,2,3]triazole),
1,10-dihydro-1,10-bis(2-isopropylphenyl)dibenzo[3,4:7,8]cycloocta[1,2-d:5,6-d']bis([1,2,3]triazole),
1,8-bis(2,6-dimethylphenyl)-1,8-dihydrodibenzo[3,4:7,8]cycloocta[1,2-d:5,6-d']bis([1,2,3]triazole),
1,10-bis(2,6-dimethylphenyl)-1,10-dihydrodibenzo[3,4:7,8]cycloocta[1,2-d:5,6-d']bis([1,2,3]triazole),
1,8-bis(2,6-diethylphenyl)-1,8-dihydrodibenzo[3,4:7,8]cycloocta[1,2-d:5,6-d']bis([1,2,3]triazole), 1,10-bis(2,6-diethylphenyl)-1,10-dihydrodibenzo[3,4:7,8]cycloocta[1,2-d:5,6-d']bis([1,2,3]triazole),
1,8-bis(2,6-diisopropylphenyl)-1,8-dihydrodibenzo[3,4:7,8]cycloocta[1,2-d:5,6-d']bis([1,2,3]triazole),
1,10-bis(2,6-diisopropylphenyl)-1,10-dihydrodibenzo[3,4:7,8]cycloocta[1,2-d:5,6-d']bis([1,2,3]triazole),
1,8-bis(2-t-butyl-6-methylphenyl)-1,8-dihydrodibenzo[3,4:7,8]cycloocta[1,2-d:5,6-d']bis([1,2,3]triazole),
1,10-bis(2-t-butyl-6-methylphenyl)-1,8-dihydrodibenzo[3,4:7,8]cycloocta[1,2-d:5,6-d']bis([1,2,3]triazole),
1,8-bis(2,6-dibromophenyl)-1,8-dihydrodibenzo[3,4:7,8]cycloocta[1,2-d:5,6-d']bis([1,2,3]triazole),
1,10-bis(2,6-dibromophenyl)-1,10-dihydrodibenzo[3,4:7,8]cycloocta[1,2-d:5,6-d']bis([1,2,3]triazole),
1,8-dihydro-1,8-bis(4-methoxyphenyl)dibenzo[3,4:7,8]cycloocta[1,2-d:5,6-d']bis([1,2,3]triazole),
1,10-dihydro-1,10-bis(4-methoxyphenyl)dibenzo[3,4:7,8]cycloocta[1,2-d:5,6-d']bis([1,2,3]triazole),
1,8-dihydro-1,8-bis(4-trifluoromethylphenyl)dibenzo[3,4:7,8]cycloocta[1,2-d:5,6-d']bis([1,2,3]triazole),
1,10-dihydro-1,10-bis(4-trifluoromethylphenyl)dibenzo[3,4:7,8]cycloocta[1,2-d:5,6-d']bis([1,2,3]triazole),
1,8-bis[3,5-bis(trifluoromethyl)phenyl]-1,8-dihydrodibenzo[3,4:7,8]cycloocta[1,2-d:5,6-d']bis([1,2,3]triazole),
1,10-bis[3,5-bis(trifluoromethyl)phenyl]-1,10-dihydrodibenzo[3,4:7,8]cycloocta[1,2-d:5,6-d']bis([1,2,3]triazole),
1,8-dihydro-1,8-bis[4-(methoxycarbonyl)benzyl]dibenzo[3,4:7,8]cycloocta[1,2-d:5,6-d']bis([1,2,3]triazole),
1,10-dihydro-1,10-bis[4-(methoxycarbonyl)benzyl]dibenzo[3,4:7,8]cycloocta[1,2-d:5,6-d']bis([1,2,3]triazole),
1,8-dibenzyl-1,8-dihydrodibenzo[3,4:7,8]cycloocta[1,2-d:5,6-d']bis([1,2,3]triazole),
1,10-dibenzyl-1,10-dihydrodibenzo[3,4:7,8]cycloocta[1,2-d:5,6-d']bis([1,2,3]triazole),
1,8-dihydro-1,8-bis[4-(hydroxymethyl)benzyl]dibenzo[3,4: 7,8]cycloocta[1,2-d:5,6-d']bis([1,2,3]triazole),
1,10-dihydro-1,10-bis[4-(hydroxymethyl)benzyl]dibenzo[3,4:7,8]cycloocta[1,2-d:5,6-d']bis([1,2,3]triazole), and so on.

In the cyclic compounds formed by the double click reaction, although it varies in accordance with the sizes of substituents $R^1$ and $R^2$, the trans forms (shown in (C) of the general scheme (I) and formulae (1-1) to (1-3)) which are thermodynamically stable are contained in a higher proportion than cis forms (shown in (D) of the general scheme (I) and formulae (2-1) to (2-3)).

2. Modification of Biomolecules by Double Click Reaction

In the method for modifying a biomolecule according to the present invention, the double click reaction (SPDC reaction) is used. That is, the azido group of the azide compound as a probe and the azido group previously introduced into the biomolecule are added and ligated to each of the two carbon-carbon triple bond sites in the cyclic diyne compound to form the cyclic compound. The substituent derived from the azide compound as the probe is incorporated into the cyclic compound thus produced which contains the biomolecule.

Double click reaction is carried out by ligating an azide compound having the function as a molecular imaging probe, e.g., a fluorescence probe, a probe for positron emission tomography (PET), etc., to an azido-protein, an azido-glycoconjugate, etc., which are previously prepared. Thus, biomolecules including proteins, glycoconjugates on the membrane surface of living cells, etc. can be modified and labeled while maintaining their functions. More specifically, details are described in EXAMPLES 21 and 22 below.

In the double click reaction, the azide compound as the probe can also be added sequentially after a biomolecule is added to the cyclic diyne compound. In this sequential double click reaction, it is preferred to remove the unreacted cyclic diyne compound remained after the addition of biomolecule and then add the azide compound only to the biomolecule-added cyclic diyne compound. On the other hand, while the biomolecule and the azide compounds are co-present, they can be added to the cyclic diyne compound. In this case, the biomolecule and the azide compounds can be ligated in one step via the cyclic diyne compound, which enables efficient chemical modification.

2A. Biomolecule

The biomolecules that can be modified according to the present invention include previously azido-incorporated proteins (including an enzyme, antibody, receptor, hormone, binding factor, ligand, cytoskeletal protein, etc.), sugars, nucleic acids, and conjugated molecules thereof, etc. In addition, the biomolecules further include not only those prepared in vitro but also biomolecules located inside, outside and on the surface of living cells.

Examples of the biomolecules are a variety of biomolecules, including cytoskeletal proteins such as actin, tubulin, vimentin, lamin, etc., and functional proteins bound thereto such as actinin, cofilin, profilin, Arp2/3, zyxin, MRTF (MAL), etc., motor proteins such as myosin, dynein, kinesin, ATP synthase, etc., adhesion proteins such as cadherin, integrin, etc., extracellular matrix proteins such as collagen, fibronectin, tenascin, biglycan, syndecan, fibrinogen, thrombin, fibrin, laminin, entactin, elastin, fasciclin, periostin, beta ig-h3, versican, decorin, etc., and proteins bound to extracellular matrix (transglutaminase, lysyl oxidase, collagen C-terminal cleavage enzyme, matrix metalloprotease, collagen receptor, etc.), etc., peptides (collagelin, etc.), sugars (hyaluronic acid, etc.), intercellular adhesion complex-associated proteins such as FAK, p130CAS, talin, vinculin, Rap, etc., heat shock proteins, endoplasmic reticulum chaperone proteins such as calreticulin, calnexin, etc., Golgi protein components such as GM130, etc., mitochondrial protein components such as cytochrome complex, etc., cell growth or cell transfer-inducing secretory proteins such as proteasome protein components, growth factor receptor proteins, Toll-like receptors, a group of signaling proteins such as STAT, MAPK, Ras, Rho, Rac, etc., epidermal growth factor EGF, fibroblast growth factor FGF, platelet-derived growth factor PDGF, neurotrophic factor, insulin, insulin-like growth factor, vascular endothelial growth factor VEGF, stem cell factor, TGFβ, etc., inflammatory cytokines such as TNFα, etc., neurotransmitters such as serotonin, adrenaline, etc., hormones such as parathyroid hormone, inhibin, calcitonin, gonadotropic hormone, melatonin, insulin, prolactin, thyroid stimulating hormone, antidiuretic hormone, epinephrine, norepinephrine, androgen, estrogen, corticoid, etc., transcription activators such as NFκB, c-fos, c-jun, SRF, heat shock factor HSF, hypoxia-inducible factor HIF, sterol regulatory element-binding protein SREBP, Hox family, Sox family, c-myc, c-myb, etc., transcription factor complex protein components such as RNA polymerase, etc., spliceosomal complex protein components such as SAP130, etc., ribosome complex protein components such as S6, etc., DNA-binding proteins such as nuclear pore complex protein components, telomerase, histone, etc., marker proteins such as annexin V specifically bound to apoptotic cells, etc., antibody proteins, luminescent proteins such as aequorin, obelin, clytin, mitrocomin, etc., fluorescent proteins such as green fluorescent protein (GFP), blue fluorescent protein (BF), fluorescent protein (RFP), etc., luciferases such as firefly luciferase, Vargula luciferase, Renilla luciferase, Gaussia luciferase, Oplophorus luciferase, BFP, etc., ligand covalent proteins such as HaloTag proteins previously specifically bound covalently with a ligand having an azido group, SNAP-tag proteins, CLIP-tag proteins, etc., low molecular ligand non-covalent proteins such as avidin, streptavidin, dehydrofolate reductase, tetracysteine motif (-CCXXCC-: X is an optional amino acid) peptide sequence-containing proteins, tetraserine motif (-SSXXSS-: X is an optional amino acid) peptide sequence-containing proteins, etc. The biomolecules further include a variety of molecules including kinases such as protein kinase C, protein kinase A, calmodulin, DYRK, p70S6K, Clk, receptor type kinases (fibroblast growth factor receptor, neurotrophic factor receptor, fibroblast growth factor receptor, insulin receptor, insulin-like growth factor receptor, vascular endothelial growth factor receptor, stem cell factor receptor, etc.), mTOR complex, GSK3, MAP kinase, Mos/Raf kinase, cdc2, etc., phosphatases such as calcineurin, lipid phosphatase PTEN, histidine phosphatase, serine/threonine-specific phosphatase, tyrosine-specific phosphatase, acidic phosphatase, alkaline phosphatase, etc., and all variants thereof, proteins previously incorporated with an azido group and obtained by fusing a plurality of the proteins above via a suitable linker, respectively, peptides and proteins prepared using non-natural amino acids containing an azido group such as azidotyrosine, azidophenylalanine, azidoalanine, azidohomoalanine, etc., glycoconjugates at the cell membrane surface including derivatives of previously azido-incorporated sialic acid, glucose, glucosamine, mannose, mannosamine, galactose, galactosamine, ribose, deoxyribose, etc., nucleotides such as previously azido-incorporated oligonucleotides, deoxynucleotides, morpholinonucleotides, etc., nucleotides and deoxynucleotides synthesized from nucleic acids such as azidoadenosine, azidoguanosine, azidothymidine, azidocytosine, azidouracil, etc., lipids such as previously azido-incorporated diacylglycerols, ceramides, sphingophospholipids, glycerophospholipids, sphingoglycolipids, glyceroglycolipids, sulfolipids, fatty acids, terpenoids, steroids, carotenoids, etc., and biological culture cells, etc., all of the natural biomolecules described above previously incorporated with an azido group that are chemically modified at random or site-specifically by photo-cross-linking or with a highly reactive functional low molecular ligand such as FITC, etc.

The biomolecules further include artificial biomolecules such as proteins artificially prepared using *Escherichia coli*, insect cells, yeast, etc., proteins artificially synthesized from amino acids in vivo. These biomolecules can all be labeled with probes.

Hereinafter, Examples are explained. However, the present invention is not limited to those Examples.

Method for Synthesis of Cyclic Diyne Compound

Diyne 3 (sym-dibenzo-1,5-cyclooctadiene-3,7-diyne) used as the cyclic diyne compound in EXAMPLES later described can be easily synthesized by the methods described in, e.g., Non-Patent Documents (a) H. N. C. Wong, P. J. Garratt, F. Sondheimer, J. Am. Chem. Soc. 1974, 96, 5604-5605; b) A. Orita, D. Hasegawa, T. Nakano, J. Otera, Chem. Eur. J. 2002, 8, 2000-2004; and c) S. Chaffin, M. Brettreich, F. Wudl, Synthesis 2002, 1191-1194).

In the synthesis of each compound, flash column chromatography was performed using silica-gel (37563-85 manufactured by Kanto Chemical Co., Inc., Silica Gel 60 N (spherical, neutral), particle size of 40-50 μm), or 37565-85 manufactured by Kanto Chemical Co., Inc., Silica Gel 60 N (spherical, neutral), particle size of 63-210 μm).

Thin-layer chromatography (TLC) was performed using a glass plate previously coated with silica-gel (1.05715 manufactured by Merck Inc., Silica Gel 60 $F_{254}$).

Measurement of Physical Properties of Compound

Structural analyses and physical properties of the compounds produced in EXAMPLES later described were determined as follows.

Melting point (Mp) was measured using a MP-J3 Micro Melting Point Measuring Apparatus manufactured by YANACO New Science Inc. (uncorrected data).

$^1H$ and $^{13}C$ NMR (nuclear magnetic resonance) spectra were measured at 300 MHz and 75.5 MHz, respectively, using a Mercury 300 NMR Spectrometer manufactured by Varian Inc., or at 500 MHz and 126 MHz, respectively, using an AVANCE 500 NMR Spectrometer manufactured by Bruker Corp. $CDCl_3$, DMSO-$d_6$ or $CD_3OD$ (all manufactured by CIL Inc.) was used as a solvent for NMR spectrometry.

Chemical shifts (δ) are given in relative values downfield from tetramethylsilane (($CH_3$)$_4$Si) (δ 0 ppm for $^1H$ NMR measured in $CDCl_3$) or the solvent peak (δ 2.49 ppm for $^1H$ NMR in DMSO-$d_6$; δ 3.30 ppm for $^1H$ NMR in $CD_3OD$; and δ 77.0 ppm for $^{13}C$ NMR in $CDCl_3$) as an internal reference with coupling constants (J) in Hz. The abbreviations s, d, t, q, m and br later described signify singlet, doublet, triplet, quartet, multiplet and broad, respectively.

Infrared (IR) spectra were measured by a diffuse reflectance method on an IRPrestige-21 Fourier Transform Infrared Spectrophotometer attached with DRS-8000A Diffuse Reflectance Accessory, manufactured by SHIMADZU Corp.

Ultraviolet (UV) absorbance spectra were measured with a UV-3100 Ultraviolet Visible Infrared Spectrophotometer, manufactured by SHIMADZU Corp. at 25° C. using a quartz cuvette (10 mm light path) under the conditions of a high speed scanning rate.

Fluorescence (FL) spectra were measured with a RF-5300PC spectrofluorophotometer manufactured by SHIMADZU Corp. at 25° C. using a quartz cuvette (10 mm light path) under the conditions of emission and excitation bandwidth, 3 nm and scan speed, medium.

High-resolution mass spectra (HRMS) were measured by positive fast atom bombardment (FAB$^+$) method or electron impact ionization (EI) method using a JMS-700 mass spectrometer manufactured by JEOL, or by positive electrospray ionization (ESI$^+$) method using a micrOTOF mass spectrometer manufactured by Bruker Inc. In the FAB$^+$ method, m-nitrobenzyl alcohol (NBA) was used as a matrix.

X-Ray crystallography was determined on an Imaging Plate Single Crystal X-ray Diffractometer for Structure Analysis manufactured by Rigaku Corp. Crystal structure was determined using a SHELXL-97 program. The crystal structure data were registered in CSD (Cambridge Crystal Structure Databases) and are available, upon request, from Cambridge Crystallographic Data Centre:CCDC, www.ccdc.-cam.ac.uk/data_request/cif.

EXAMPLE 1

Production 1 of Bis-cycloadducts by SPDC Reaction

[Chemical formula (4)]

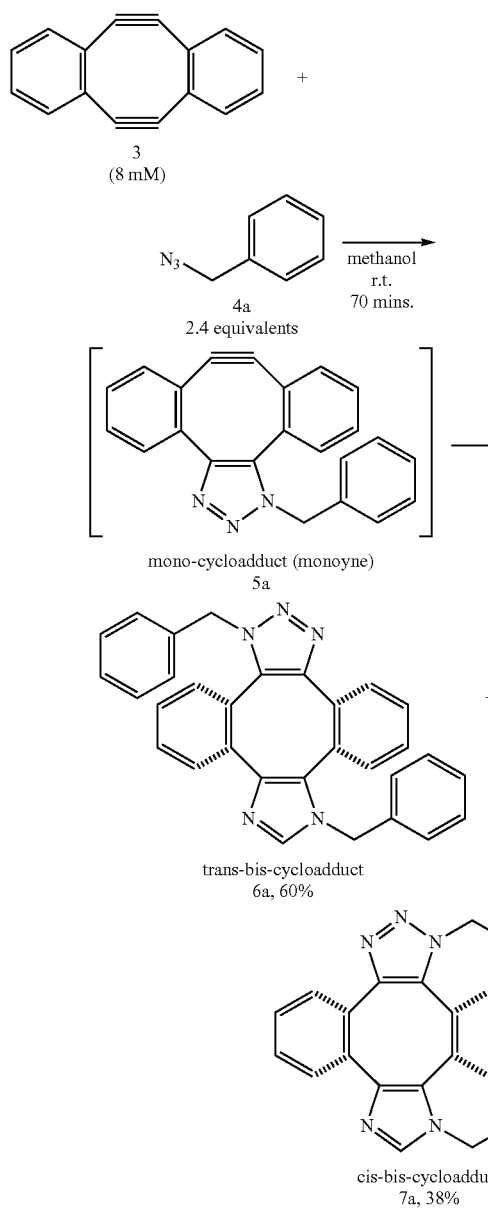

(4)

As shown in the reaction scheme (4) above, to a solution of diyne 3 (40.0 mg, 200 μmol) in methanol (23.5 mL) was added a solution of benzyl azide (4a, commercial product) (63.9 mg, 480 μmol) in methanol (1.5 mL) at room temperature. After stirring for 70 minutes at the same temperature, the reaction solution was concentrated under reduced pressure using an evaporator. The residue was purified by flash column chromatography (silica-gel 10 g, dichloromethane only to dichloromethane/methanol=6/1) to give two regioisomeric bis-cycloadducts of trans-6a (55.8 mg, 120 μmol, 59.9%) and cis-7a (35.2 mg, 75.4 μmol, 37.8%). The geometries of the respective compounds were confirmed by X-ray crystallographical analyses (CCDC 759900 (6a) and CCDC 759902 (7a)).

1,8-Dibenzyl-1,8-dihydrodibenzo[3,4:7,8]cycloocta[1,2-d:5,6-d']bis([1,2,3]triazole) (6a)

Recrystallization from n-hexane/ethyl acetate gave colorless crystals. The following physical properties of the crystals were measured to conduct structural analysis.

Mp 230-232° C.;
$R_f$=0.26 (hexane/ethyl acetate=1/1);
$R_f$=0.69 (dichloromethane/methanol=9/1);
$^1$H NMR (300 MHz, CDCl$_3$) δ 5.31 (d, 2H, J=15.3 Hz), 5.50 (d, 2H, J=15.3 Hz), 6.94-7.01 (m, 4H), 7.09 (dd, 2H, J=0.8, 7.6 Hz), 7.22-7.30 (m, 6H), 7.40 (ddd, 2H, J=1.3, 7.6, 7.6 Hz), 7.52 (ddd, 2H, J=1.3, 7.6, 7.6 Hz), 7.71 (dd, 2H, J=0.8, 7.6 Hz);
$^{13}$C NMR (75.5 MHz, CDCl$_3$) δ 52.1 (2C), 126.4 (2C), 127.0 (4C), 128.2 (2C), 128.7 (2C), 128.8 (4C), 129.9 (2C), 130.2 (2C), 131.2 (2C), 132.6 (2C), 134.9 (2C), 135.1 (2C), 145.0 (2C);
IR (KBr, cm$^{-1}$) 706, 731,764, 910, 984, 1028, 1215, 1250, 1350, 1454, 1497, 1514, 3063;
HRMS (ESI$^+$) m/z 467.1984 ([M+H]$^+$, C$_{30}$H$_{23}$N$_6$$^+$ Calcd. 467.1979).

1,10-Dibenzyl-1,10-dihydrodibenzo[3,4:7,8]cycloocta[1,2-d:5,6-d']bis([1,2,3]triazole) (7a)

Recrystallization from n-hexane/ethyl acetate gave colorless crystals. The following physical properties of the crystals were measured to conduct structural analysis.

Mp 274-277° C.;
$R_f$=0.26 (hexane/ethyl acetate=1/1);
$R_f$=0.44 (dichloromethane/methanol=9/1);
$^1$H NMR (300 MHz, CDCl$_3$) δ 4.89 (d, 2H, J=15.5 Hz), 5.31 (d, 2H, J=15.5 Hz), 6.94-7.04 (m, 4H), 7.04-7.14 (m, 2H), 7.24-7.36 (m, 6H), 7.36-7.45 (m, 2H), 7.45-7.54 (m, 2H), 7.62-7.72 (m, 2H);
$^{13}$C NMR (75.5 MHz, CDCl$_3$) δ 52.0 (2C), 127.2 (4C), 127.9 (2C), 128.3 (2C), 128.8 (4C), 129.1 (2C), 129.8 (2C), 130.3 (2C), 130.7 (2C), 130.9 (2C), 133.6 (2C), 135.3 (2C), 146.2 (2C);
IR (KBr, cm$^{-1}$) 698, 729, 766, 910, 984, 1028, 1211, 1246, 1344, 1427, 1454, 1497, 1516, 3061;
HRMS (ESI$^+$) m/z 467.1982 ([M+H]$^+$, C$_{30}$H$_{23}$N$_6$$^+$ Calcd. 467.1979).

EXAMPLE 2

Production 2 of Bis-cycloadducts by SPDC Reaction

[Chemical formula (5)]

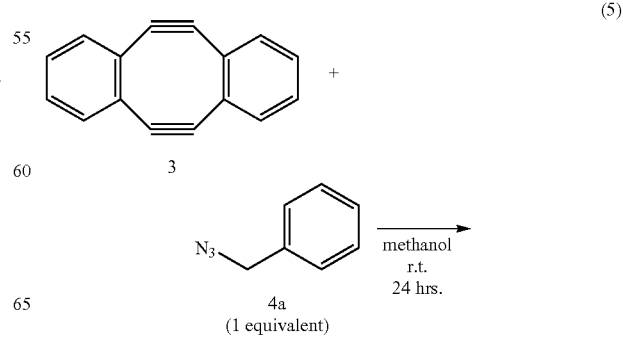

(5)

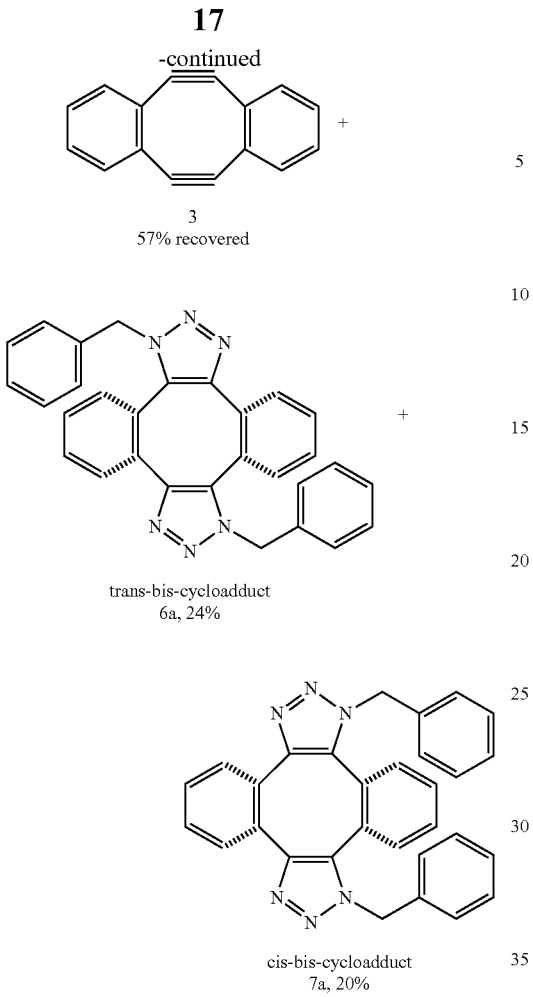

trans-bis-cycloadduct
6a, 24% cis-bis-cycloadduct
7a, 20%

As shown in the reaction scheme (5) above, to a solution of diyne 3 (40.0 mg, 200 μmol) in methanol (23.5 mL) was added a solution of benzyl azide (4a) (26.6 mg, 200 μmol) in methanol (1.5 mL) at room temperature. After stirring for 24 hours at the same temperature, the reaction solution was concentrated under reduced pressure using an evaporator. The residue was purified by flash column chromatography (silica-gel 10 g, dichloromethane only to dichloromethane/methanol=6/1) to give two regioisomeric bis-cycloadducts of trans-6a (22.0 mg, 47.2 μmol, 23.6%) and cis-7a (19.0 mg, 40.7 μmol, 20.4%) along with recovery of starting diyne 3 (22.7 mg, 113 μmol, 56.8%).

In the SPDC reaction of EXAMPLE 1 described above, the mono-cycloadduct 5a (cf., reaction scheme (4) above), a presumable monoyne intermediate, was neither detected nor isolated. Furthermore, as in the SPDC reaction of EXAMPLE 2, the mono-cycloadduct 5a was not obtained even by reaction of diyne 3 with an equimolar amount of benzyl azide (4a) but bis-cycloadducts 6a and 7a and diyne 3 were only recovered. The combined yield of bis-cycloadducts 6a and 7a and recovered diyne 3 was 100% based on the starting diyne 3. These results indicate that the intermediate 5a is more reactive toward benzyl azide 4a than the starting diyne 3. As such, the higher reactivity of the intermediate in the SPDC reaction than the starting diyne was also supported by calculated results of the activation energy, etc. of the reactions later described.

As such, two azide compounds are added and ligated to the cyclic diyne compound to form the cyclic skeleton of an 8-membered ring and the two 1,2,3-triazole ring sharing the carbon-carbon double bond sites with the cyclic skeleton. Diyne 3 has a strain, is stable and easily handled and thus suitable as the substrate for the SPDC reaction. As shown in formula (3) above, the cyclic diyne compound having a substituent such as a hydrocarbon group(s) on either one or both of the two benzene rings of diyne 3 can be used instead of diyne 3.

EXAMPLE 3

Production 3 of Bis-cycloadducts by SPDC Reaction

[Chemical formula (6)]

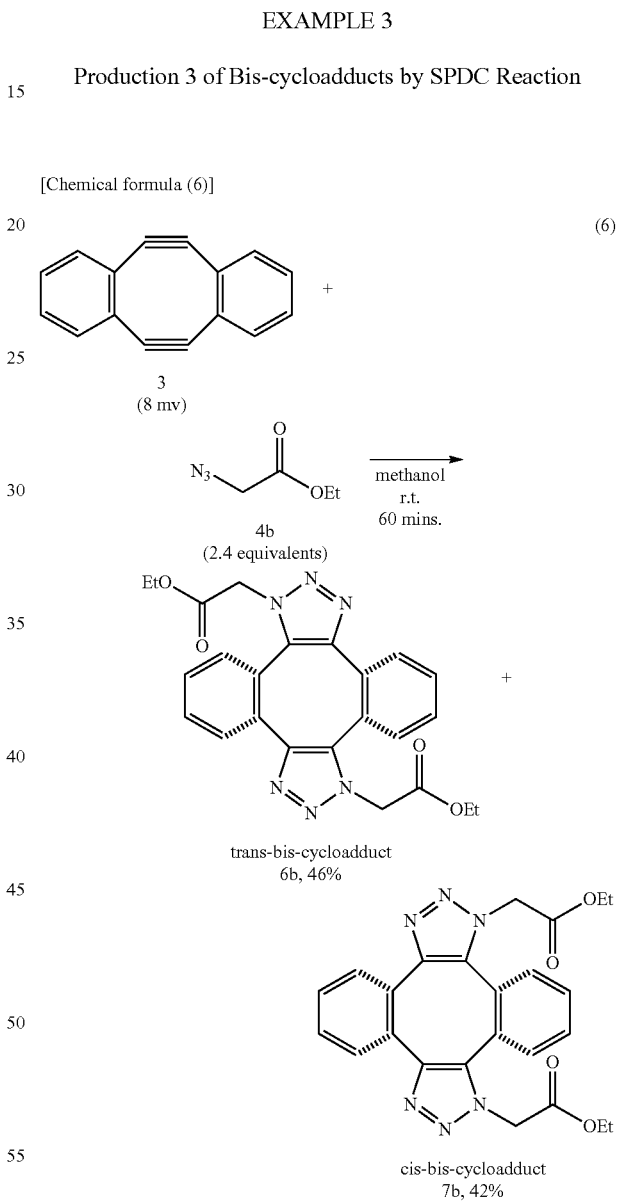

trans-bis-cycloadduct
6b, 46% cis-bis-cycloadduct
7b, 42%

As shown in the reaction scheme (6) above, to a solution of diyne 3 (40.0 mg, 200 μmol) in methanol (23.5 mL) was added a solution of ethyl azidoacetate (4b, commercial product) (55.0 μL, 480 μmol) in methanol (1.5 mL) at room temperature. After stirring for 60 minutes at the same temperature, the reaction solution was concentrated under reduced pressure using an evaporator. The residue was purified by flash column chromatography (silica-gel 10 g, hexane/ethyl acetate=1/1) to give two regioisomeric bis-cycloadducts of trans-6b (41.9 mg, 91.5 μmol, 45.8%) and cis-7b (38.8 mg, 84.7 μmol, 42.4%). The geometries of the respective compounds were confirmed by X-ray crystallographical analyses (CCDC 759901 (6b) and CCDC 759903 (7b)).

1,8-Bis(ethoxycarbonylmethyl)-1,8-dihydrodibenzo[3,4:7,8]cycloocta[1,2-d:5,6-d']bis([1,2,3]triazole) (6b)

Recrystallization from n-hexane/ethyl acetate gave colorless crystals. The following physical properties of the crystals were measured to conduct structural analysis.

Mp 204-205° C.;

$R_f$=0.55 (hexane/ethyl acetate=1/3);

$^1$H NMR (300 MHz, CDCl$_3$) δ 1.23 (t, 6H, J=7.1 Hz), 4.10-4.34 (m, 4H), 4.87 (d, 2H, J=17.4 Hz), 5.09 (d, 2H, J=17.4 Hz), 7.31 (d, 2H, J=7.1 Hz), 7.48 (dd, 2H, J=7.1, 7.1 Hz), 7.57 (dd, 2H, J=7.1, 7.1 Hz), 7.78 (d, 2H, J=7.1 Hz);

$^{13}$C NMR (75.5 MHz, CDCl$_3$) δ 13.8 (2C), 49.4 (2C), 62.3 (2C), 125.7 (2C), 129.0 (2C), 129.1 (2C), 130.3 (2C), 131.5 (2C), 132.4 (2C), 135.3 (2C), 144.4 (2C), 166.3 (2C);

IR (KBr, cm$^{-1}$) 737, 766, 779, 876, 910, 986, 1022, 1134, 1161, 1211, 1256, 1348, 1364, 1418, 1474, 1516, 1748, 2982;

HRMS (ESI$^+$) m/z 459.1788 ([M+H]$^+$, C$_{24}$H$_{23}$N$_6$O$_4^+$ Calcd. 459.1775).

1,10-Bis(ethoxycarbonylmethyl)-1,10-dihydrodibenzo[3,4:7,8]cycloocta[1,2-d:5,6-d']bis([1,2,3]triazole) (7b)

Recrystallization from n-hexane/ethyl acetate gave colorless crystals. The following physical properties of the crystals were measured to conduct structural analysis.

Mp 214-217° C.;

$R_f$=0.38 (hexane/ethyl acetate=1/3);

$^1$H NMR (300 MHz, CDCl$_3$) δ 1.26 (t, 6H, J=7.1 Hz), 4.21 (q, 4H, J=7.1 Hz), 5.03 (d, 2H, J=17.4 Hz), 5.13 (d, 2H, J=17.4 Hz), 7.35-7.44 (m, 2H), 7.47-7.59 (m, 4H), 7.66-7.76 (m, 2H);

$^{13}$C NMR (75.5 MHz, CDCl$_3$) δ 13.9 (2C), 49.3 (2C), 62.2 (2C), 128.3 (2C), 129.0 (2C), 129.8 (2C), 130.19 (2C), 130.22 (2C), 130.8 (2C), 134.5 (2C), 145.6 (2C), 166.5 (2C);

IR (KBr, cm$^{-1}$) 733, 768, 799, 876, 912, 986, 1020, 1132, 1161, 1211, 1250, 1346, 1362, 1414, 1474, 1518, 1748, 2984;

HRMS (ESI$^+$) m/z 459.1783 ([M+H]$^+$, C$_{24}$H$_{23}$N$_6$O$_4^+$ Calcd. 459.1775).

EXAMPLE 4

Production 4 of Bis-cycloadducts by SPDC Reaction

[Chemical formula (7)]

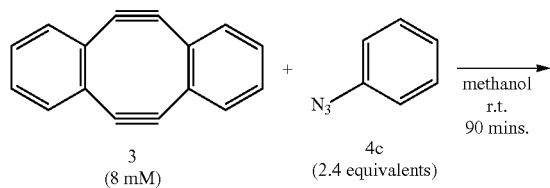

(7)

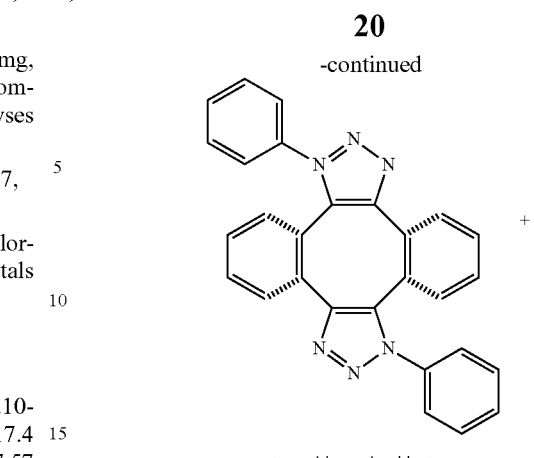

trans-bis-cycloadduct
6c, 42%

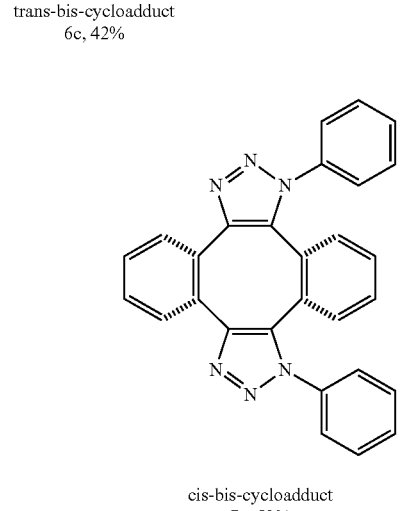

cis-bis-cycloadduct
7c, 53%

As shown in the reaction scheme (7) above, to a solution of diyne 3 (40.0 mg, 200 μmol) in methanol (23.5 mL) was added a solution of phenyl azide (4c, synthesized by the method described in Non-Patent Document N. D. Obushak, N. T. Pokhodylo, N. I. Pidlypnyi, V. S. Matiichuk, Russ. J. Org. Chem. 2008, 44, 1522-1527) (57.2 mg, 480 μmol) in methanol (1.5 mL) at room temperature. After stirring for 90 minutes at the same temperature, the reaction solution was concentrated under reduced pressure using an evaporator. The residue was purified by flash column chromatography (silica-gel 10 g, hexane/ethyl acetate=4/1) to give two regioisomeric bis-cycloadducts of trans-6c (36.5 mg, 83.2 μmol, 41.7%) and cis-7c (46.1 mg, 105 μmol, 52.6%). The geometries of the respective compounds were confirmed by X-ray crystallographical analyses (CCDC 759898 (6c) and CCDC 759905 (7c)).

1,8-Dihydro-1,8-diphenyldibenzo[3,4:7,8]cycloocta[1,2-d:5,6-d']bis([1,2,3]triazole) (6c)

Recrystallization from n-hexane/dichloromethane gave colorless crystals. The following physical properties of the crystals were measured to conduct structural analysis.

Mp >300° C.;

$R_f$=0.23 (hexane/ethyl acetate=3/1);

$^1$H NMR (300 MHz, CDCl$_3$) δ 6.84 (dd, 2H, J=1.2, 7.8 Hz), 7.21 (ddd, 2H, J=1.2, 7.8, 7.8 Hz), 7.29-7.43 (m, 10H), 7.48 (ddd, 2H, J=1.2, 7.8, 7.8 Hz), 7.83 (dd, 2H, J=1.2, 7.8 Hz);

$^{13}$C NMR (75.5 MHz, CDCl$_3$) δ 125.0 (4C), 126.7 (2C), 128.8 (2C), 129.1 (2C), 129.3 (4C), 130.0 (2C), 130.8 (2C), 131.3 (2C), 131.9 (2C), 134.2 (2C), 135.9 (2C), 145.8 (2C);

IR (KBr, cm$^{-1}$) 692, 734, 768, 997, 1265, 1361, 1497, 1512, 1595;

HRMS (ESI$^+$) m/z 439.1667 ([M+H$^+$], C$_{28}$H$_{19}$N$_6$$^+$ Calcd. 439.1666).

1,10-Dihydro-1,10-diphenyldibenzo[3,4:7,8]cycloocta[1,2-d:5,6-d']bis([1,2,3]triazole) (7c)

Recrystallization from n-hexane/dichloromethane gave colorless crystals. The following physical properties of the crystals were measured to conduct structural analysis.

Mp >300° C.;

R$_f$=0.13 (hexane/ethyl acetate=3/1);

$^1$H NMR (300 MHz, CDCl$_3$) δ 6.87-6.95 (m, 2H), 7.12-7.21 (m, 2H), 7.39-7.51 (m, 10H), 7.52-7.62 (m, 2H), 7.77-7.85 (m, 2H);

$^{13}$C NMR (75.5 MHz, CDCl$_3$) δ 126.1 (4C), 127.4 (2C), 129.4 (4C), 129.6 (2C), 129.8 (2C), 130.3 (2C), 130.6 (2C), 131.4 (2C), 131.6 (2C), 134.1 (2C), 135.8 (2C), 145.1 (2C);

IR (KBr, cm$^{-1}$) 527, 608, 687, 734, 762, 997, 1069, 1132, 1175, 1263, 1358, 1427, 1476, 1497, 1514, 1595;

HRMS (ESI$^+$) m/z 439.1670 ([M+H]$^+$, C$_{28}$H$_{19}$N$_6$$^+$ Calcd. 439.1666).

EXAMPLE 5

Production 5 of Bis-cycloadducts by SPDC Reaction

[Chemical formula (8)]

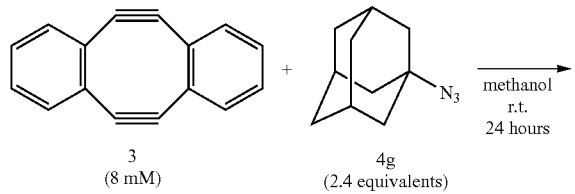

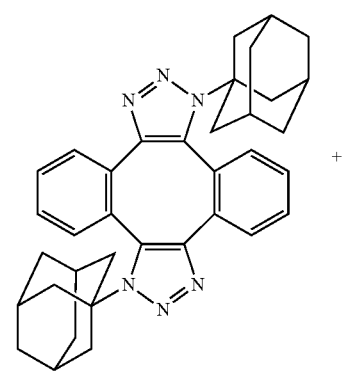

trans-bis-cycloadduct
6g, 25%

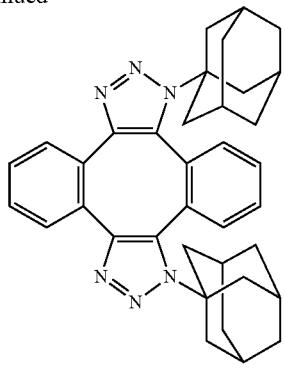

cis-bis-cycloadduct
7g, 70%

(6g/7g = 26/74)

As shown in the reaction scheme (8) above, to a solution of diyne 3 (40.0 mg, 200 μmol) in methanol (25.0 mL) was added 1-azidoadamantane (4g) (85.1 mg, 480 μmol) at room temperature. After stirring for 24 hours at room temperature, the reaction solution was concentrated under reduced pressure. The residue was purified by thin-layer chromatography (dichloromethane/methanol=49/1) to give trans-6g (27.5 mg, 49.6 μmol, 24.8%) and cis-7g (77.9 mg, 140 μmol, 70.3%). The geometries of the respective compounds were confirmed by X-ray crystallographical analyses (CCDC 810930 (6g) and CCDC 810837 (7g)).

1,8-Diadamantyl-1,8-dihydrodibenzo[3,4:7,8]cycloocta[1,2-d:5,6-d']bis([1,2,3]triazole) (6g)

The following physical properties of the colorless crystals obtained were measured to perform structural analysis.

Mp 240-242° C.;

R$_f$=0.79 (dichloromethane/methanol=9/1);

$^1$H NMR (500 MHz, CDCl$_3$) δ 1.56-1.65 (m, 12H), 2.02-2.11 (m, 12H), 2.21-2.25 (m, 6H), 7.32-7.38 (m, 4H), 7.47 (ddd, 2H, J=1.5, 7.5, 7.5 Hz), 7.64 (d, 2H, J=7.5 Hz);

$^{13}$C NMR (126 MHz, CDCl$_3$) 29.7 (6C), 35.7 (6C), 42.7 (6C), 63.9 (2C), 127.6 (2C), 129.6 (2C), 129.8 (2C), 130.5 (2C), 130.9 (2C), 132.5 (2C), 134.3 (2C), 146.5 (2C);

IR (KBr, cm$^{-1}$) 731, 764, 777, 839, 912, 1011, 1101, 1125, 1260, 1306, 1323, 1358, 1452, 2853, 2909;

HRMS (ESI$^+$) m/z 555.3237 ([M+H]$^+$, C$_{36}$H$_{39}$N$_6$$^+$ requires 555.3231).

1,10-Diadamantyl-1,10-dihydrodibenzo[3,4:7,8]cycloocta[1,2-d:5,6-d']bis([1,2,3]triazole) (7g)

The following physical properties of the colorless crystals obtained were determined to perform structural analysis.

Mp >300° C.;

R$_f$=0.57 (dichloromethane/methanol=9/1);

$^1$H NMR (500 MHz, CDCl$_3$) δ 1.68 (br d, 6H, J=12.0 Hz), 1.74 (br d, 6H, J=12.0 Hz), 2.18 (br s, 6H), 2.34 (br s, 12H), 7.31-7.35 (m, 2H), 7.36-7.43 (m, 4H), 7.58-7.63 (m, 2H);

$^{13}$C NMR (126 MHz, CDCl$_3$) δ 29.8 (6C), 35.8 (6C), 44.0 (6C), 63.9 (2C), 128.4 (2C), 128.7 (2C), 130.2 (2C), 130.8 (2C), 131.1 (2C), 132.3 (2C), 132.9 (2C), 147.2 (2C); IR (KBr, cm$^{-1}$) 737, 766, 908, 1011, 1101, 1308, 1321, 1452, 2855, 2914;

HRMS (ESI+) m/z 555.3257 ([M+H]+, C36H39N6+ requires 555.3231).

EXAMPLE 6

Production 6 of Bis-cycloadducts by SPDC Reaction

[Chemical formula (9)]

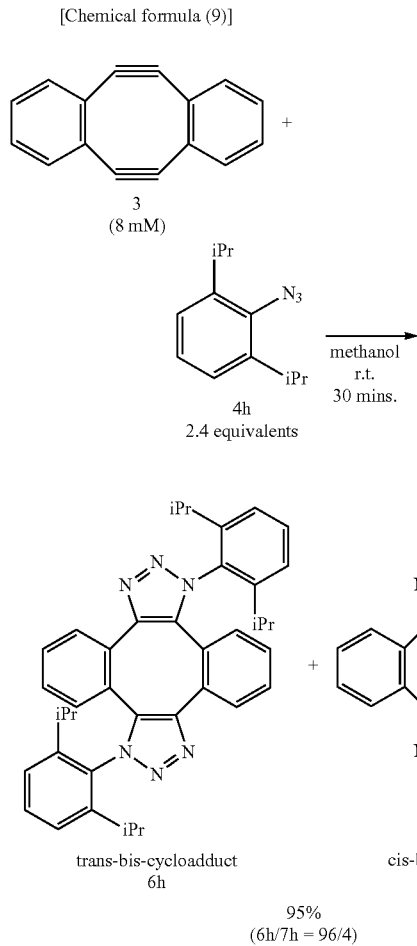

(9)

As shown in the reaction scheme (9) above, to a solution of diyne 3 (10.0 mg, 50.0 µmol) in methanol (5.00 mL) was added a solution of 2,6-diisopropylphenyl azide (4h) (24.4 mg, 120 µmol) in methanol (1.25 mL) at room temperature. After stirring for 30 minutes at room temperature, the reaction solution was concentrated under reduced pressure. The residue was purified by flash column chromatography (silica-gel 10 g, dichloromethane/methanol=100/1) to give a mixture of trans-6h and cis-7h (28.9 mg, 47.6 µmol, 95.4%). The ratio of the trans-6h to cis-7h was determined based on the 1H NMR spectrum. The geometries of the respective compounds were confirmed by X-ray crystallographical analyses (CCDC 810931 (6h) and CCDC 810838 (7h)).

1,8-Bis(2,6-diisopropylphenyl)-1,8-dihydrodibenzo[3,4:7,8]cycloocta[1,2-d:5,6-d']bis([1,2,3]triazole) (6h)

The following physical properties of the colorless crystals obtained were determined to perform structural analysis.
Mp 273-275° C.;
$R_f$=0.65 (dichloromethane/methanol=49/1);
1H NMR (500 MHz, CDCl3) δ 0.73 (d, 6H, J=7.0 Hz), 0.78 (d, 6H, J=7.0 Hz), 1.410 (d, 6H, J=6.5 Hz), 1.413 (d, 6H, J=6.5 Hz), 1.96 (qq, 2H, J=7.0, 7.0 Hz), 2.63 (qq, 2H, J=6.5, 6.5 Hz), 6.87 (d, 2H, J=7.5 Hz), 7.06 (d, 2H, J=7.5 Hz), 7.17 (ddd, 2H, J=1.0, 7.8, 7.8 Hz), 7.35 (dd, 2H, J=1.0, 7.8 Hz), 7.38-7.45 (m, 4H), 7.81 (d, 2H, J=7.5 Hz);
13C NMR (126 MHz, CDCl3) δ 22.3 (2C), 22.8 (2C), 24.4 (2C), 26.2 (2C), 28.3 (2C), 29.2 (2C), 123.85 (2C), 123.92 (2C), 126.3 (2C), 128.4 (2C), 129.6 (2C), 129.7 (2C), 130.7 (2C), 131.5 (4C), 132.5 (2C), 135.9 (2C), 144.1 (2C), 145.6 (2C), 146.9 (2C);
IR (KBr, cm−1) 733, 756, 768, 995, 1362, 1470, 2868, 2930, 2965;
HRMS (ESI+) m/z 607.3525 ([M+H]+, C40H43N6+ requires 607.3544);
C40H42N6: Calcd.: C, 79.17; H, 6.98; N, 13.85%; Found: C, 79.09; H, 6.99; N, 13.59%.

1,10-Bis(2,6-diisopropylphenyl)-1,10-dihydrodibenzo[3,4:7,8]cycloocta[1,2-d:5,6-d']bis([1,2,3]triazole) (7h)

The following physical properties of the colorless crystals obtained were determined to perform structural analysis.
$R_f$=0.40 (dichloromethane/methanol=49/1);
1H NMR (500 MHz, CDCl3) δ 0.42 (d, 6H, J=6.8 Hz), 0.98 (d, 6H, J=6.8 Hz), 1.29 (d, 6H, J=6.8 Hz), 1.32 (d, 6H, J=6.8 Hz), 2.07 (dq, 2H, J=6.8, 6.8 Hz), 2.21 (dq, 2H, J=6.8, 6.8 Hz), 6.93 (dd, 2H, J=3.5, 5.5 Hz), 7.03 (dd, 2H, J=3.5, 5.5 Hz), 7.12 (d, 2H, J=7.5 Hz), 7.33 (d, 2H, J=7.5 Hz), 7.45 (dd, 2H, J=7.5, 7.5 Hz), 7.55 (dd, 2H, J=3.5, 5.5 Hz), 7.76 (dd, 2H, J=3.5, 5.5 Hz);
13C NMR (126 MHz, CDCl3) δ 21.8 (2C), 22.5 (2C), 25.5 (2C), 26.2 (2C), 29.0 (2C), 29.3 (2C), 124.26 (2C), 124.34 (2C), 127.7 (2C), 128.8 (2C), 129.2 (2C), 130.9 (2C), 131.00 (2C), 131.02 (2C), 131.1 (2C), 132.3 (2C), 135.7 (2C), 145.7 (2C), 146.2 (2C), 147.9 (2C);
IR (KBr, cm−1) 733, 764, 991, 1277, 1354, 1456, 1724, 2868, 2928, 2964;
HRMS (ESI+) m/z 629.3348 ([M+Na]+, C40H42N6Na+ requires 629.3363).

EXAMPLE 7

Production 7 of Bis-cycloadducts by SPDC Reaction

[Chemical formula (10)]

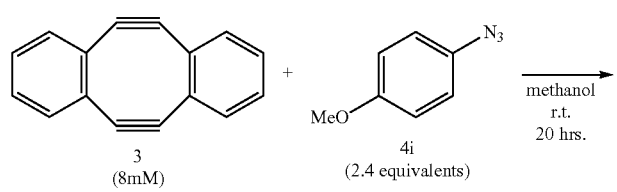

(10)

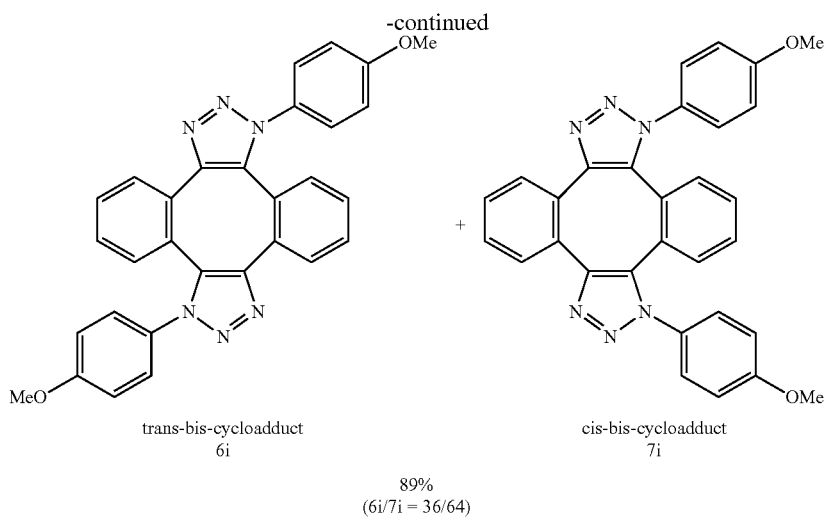

trans-bis-cycloadduct
6i cis-bis-cycloadduct
7i

89%
(6i/7i = 36/64)

As shown in the reaction scheme (10) above, to a solution of diyne 3 (40.0 mg, 200 μmol) in methanol (22.0 mL) was added a solution of 4-methoxyphenyl azide (4i) (71.6 mg, 480 μmol) in methanol (3.00 mL) at room temperature. After stirring for 20 minutes at room temperature, the reaction solution was concentrated under reduced pressure. The residue was purified by flash column chromatography (silica-gel 10 g, dichloromethane only to dichloromethane/methanol=49/1) to give a mixture of trans-6i and cis-7i (88.8 mg, 178 μmol, 89.2%). The ratio of trans-6i and cis-7i was determined based on the $^1$H NMR spectrum. The geometries of the respective compounds were confirmed by X-ray crystallographical analyses (CCDC 810932 (6i) and CCDC 810839 (7i)).

1,8-Dihydro-1,8-bis(4-methoxyphenyl)dibenzo[3,4:7,8]cycloocta[1,2-d:5,6-d']bis([1,2,3]triazole) (6i)

The following physical properties of the colorless crystals obtained were determined to perform structural analysis.

Mp 250-251° C.;
$R_f$=0.47 (n-hexane/ethyl acetate/dichloromethane/toluene=1/1/1/1);
$^1$H NMR (500 MHz, CDCl$_3$) δ 3.82 (s, 6H), 6.83-6.88 (m, 6H), 7.19-7.24 (m, 6H), 7.47 (ddd, 2H, J=1.0, 7.5, 7.5 Hz), 7.81 (d, 2H, J=7.5 Hz);
$^{13}$C NMR (126 MHz, CDCl$_3$) δ 55.5 (2C), 114.4 (4C), 126.4 (4C), 126.8 (2C), 128.8 (2C), 129.1 (2C), 129.9 (2C), 130.8 (2C), 131.2 (2C), 132.1 (2C), 134.2 (2C), 145.7 (2C), 159.9 (2C);
IR (KBr, cm$^{-1}$) 538, 592, 733, 764, 833, 910, 993, 1028, 1053, 1103, 1115, 1169, 1182, 1252, 1302, 1443, 1464, 1514, 1589, 1609;
HRMS (ESI$^+$) m/z 499.1886 ([M+H]$^+$, C$_{30}$H$_{23}$N$_6$O$_2$$^+$ requires 499.1877);
C$_{30}$H$_{22}$N$_6$O$_2$: Calcd.: C, 72.28; H, 4.45; N, 16.86%; Found: C, 72.09; H, 4.32; N, 16.60%.

1,10-Dihydro-1,10-bis(4-methoxyphenyl)dibenzo[3,4:7,8]cycloocta[1,2-d:5,6-d']bis([1,2,3]triazole) (7i)

The following physical properties of the colorless crystals obtained were determined to perform structural analysis.

Mp >300° C.;
$R_f$=0.38 (n-hexane/ethyl acetate/dichloromethane/toluene=1/1/1/1);
$^1$H NMR (500 MHz, CDCl$_3$) δ 3.87 (s, 6H), 6.89-6.95 (m, 2H), 6.94 (AA'BB', 4H), 7.13-7.19 (m, 2H), 7.31 (AA'BB', 4H), 7.52-7.57 (m, 2H), 7.76-7.82 (m, 2H);
$^{13}$C NMR (126 MHz, CDCl$_3$) δ 55.6 (2C), 114.5 (4C), 126.5 (4C), 128.4 (2C), 129.2 (2C), 129.3 (2C), 129.4 (2C), 130.5 (2C), 130.7 (2C), 131.6 (2C), 133.5 (2C), 146.4 (2C), 160.1 (2C);
IR (KBr, cm$^{-1}$) 532, 594, 733, 762, 775, 831, 995, 1020, 1036, 1256, 1306, 1516, 1611;
HRMS (ESI$^+$) m/z 499.1876 ([M+H]$^+$, C$_{30}$H$_{22}$N$_6$O$_2$$^+$ requires 499.1877);
C$_{30}$H$_{22}$N$_6$O$_2$: Calcd.: C, 72.28; H, 4.45; N, 16.86%; Found: C, 72.14; H, 4.38; N, 16.81%.

EXAMPLE 8

Production 8 of Bis-cycloadducts by SPDC Reaction

[Chemical formula (11)]

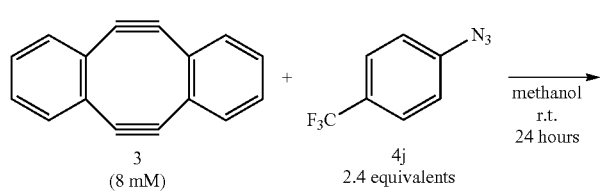

(11)

3
(8 mM)

4j
2.4 equivalents methanol
r.t.
24 hours

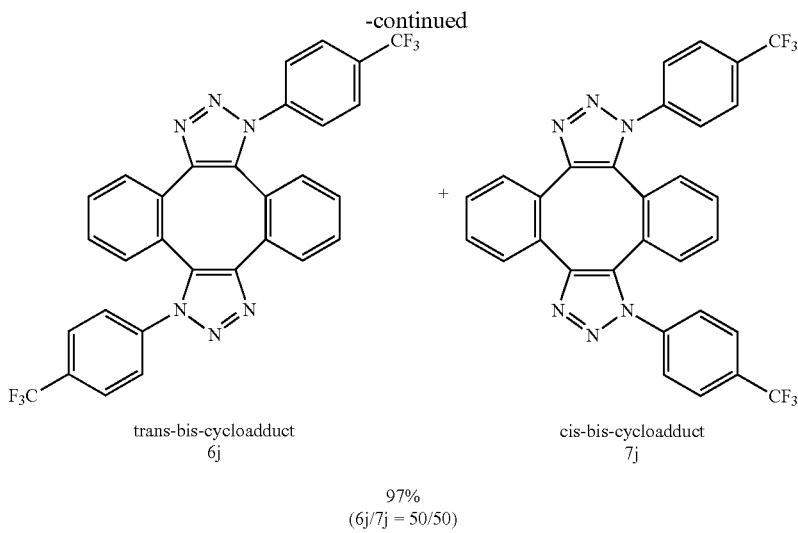

trans-bis-cycloadduct
6j cis-bis-cycloadduct
7j

97%
(6j/7j = 50/50)

As shown in the reaction scheme (11) above, to a solution of diyne 3 (40.0 mg, 200 μmol) in methanol (22.0 mL) was added a solution of 4-trifluoromethylphenyl azide (4j) (89.8 mg, 480 μmol) in methanol (3.00 mL) at room temperature. After stirring for 24 hours at room temperature, the reaction solution was concentrated under reduced pressure. The residue was purified by thin-layer chromatography (n-hexane/ethyl acetate=9/1) to give a mixture of trans-6j and cis-7j (111 mg, 193 μmol, 96.7%). The ratio of trans-6j and cis-7j was determined based on the $^1$H NMR spectrum.

1,8-Dihydro-1,8-bis(4-trifluoromethylphenyl)dibenzo[3,4:7,8]cycloocta[1,2-d:5,6-d']bis([1,2,3]triazole) (6j)

The following physical properties of the colorless crystals obtained were determined to perform structural analysis.

Mp 270-272° C.;
$R_f$=0.19 (n-hexane/ethyl acetate=9/1);
$^1$H NMR (500 MHz, CDCl$_3$) δ 6.85 (dd, 2H, J=1.0, 7.5 Hz), 7.28 (ddd, 2H, J=1.0, 7.5, 7.5 Hz), 7.45 (d, 4H, J=8.5 Hz), 7.55 (ddd, 2H, J=1.0, 7.5, 7.5 Hz), 7.66 (d, 4H, J=8.5 Hz), 7.86 (dd, 2H, J=1.0, 7.5 Hz);
$^{13}$C NMR (126 MHz, CDCl$_3$) δ 123.4 (q, 2C, $J^1_{cf}$=273 Hz), 125.0 (4C), 126.2 (2C), 126.6 (q, 4C, $J^3_{cf}$=3.5 Hz), 129.4 (2C), 130.5 (2C), 130.8 (2C), 131.1 (q, 2C, $J^2_{cf}$=32.9 Hz), 131.5 (2C), 131.6 (2C), 134.2 (2C), 138.6 (2C), 146.1 (2C);
IR (KBr, cm$^{-1}$) 733, 764, 845, 995, 1043, 1070, 1130, 1171, 1323, 1366, 1406, 1520, 1614, 3065;
HRMS (ESI$^+$) m/z 575.1399 ([M+H]$^+$, C$_{30}$H$_{17}$F$_6$N$_6^+$ requires 575.1413).

1,10-Dihydro-1,10-bis(4-trifluoromethylphenyl)dibenzo[3,4:7,8]cycloocta[1,2-d:5,6-d']bis([1,2,3]triazole) (7j)

Mp >300° C.;
$R_f$=0.13 (n-hexane/ethyl acetate=9/1);
$^1$H NMR (500 MHz, CDCl$_3$) δ 6.91-6.96 (m, 2H), 7.24-7.30 (m, 2H), 7.56 (d, 2H, J=8.0 Hz), 7.56-7.61 (m, 4H), 7.78 (d, 2H, J=8.0 Hz), 7.77-7.82 (m, 4H);
$^{13}$C NMR (126 MHz, CDCl$_3$) δ 123.3 (q, 2C, $J^1_{cf}$=273 Hz), 124.9 (4C), 126.8 (q, 4C, $J^3_{cf}$=3.5 Hz), 127.8 (2C), 129.7 (2C), 129.9 (2C), 130.2 (2C), 130.9 (2C), 131.4 (q, 2C, $J^2_{cf}$=33.3 Hz), 131.9 (2C), 133.2 (2C), 138.9 (2C), 147.1 (2C);
IR (KBr, cm$^{-1}$) 733, 764, 775, 843, 997, 1047, 1063, 1076, 1119, 1169, 1329, 1360, 1412, 1522, 1618, 3071;
HRMS (ESI$^+$) m/z 575.1412 ([M+H]$^+$, C$_{30}$H$_{17}$F$_6$N$_6^+$ requires 575.1413);
C$_{30}$H$_{16}$F$_6$N$_6$: Calcd.: C, 62.72; H, 2.81; N, 14.63%; Found: C, 63.01; H, 3.06; N, 14.48%.

EXAMPLE 9

Production 9 of Bis-cycloadducts by SPDC Reaction

[Chemical formula (12)]

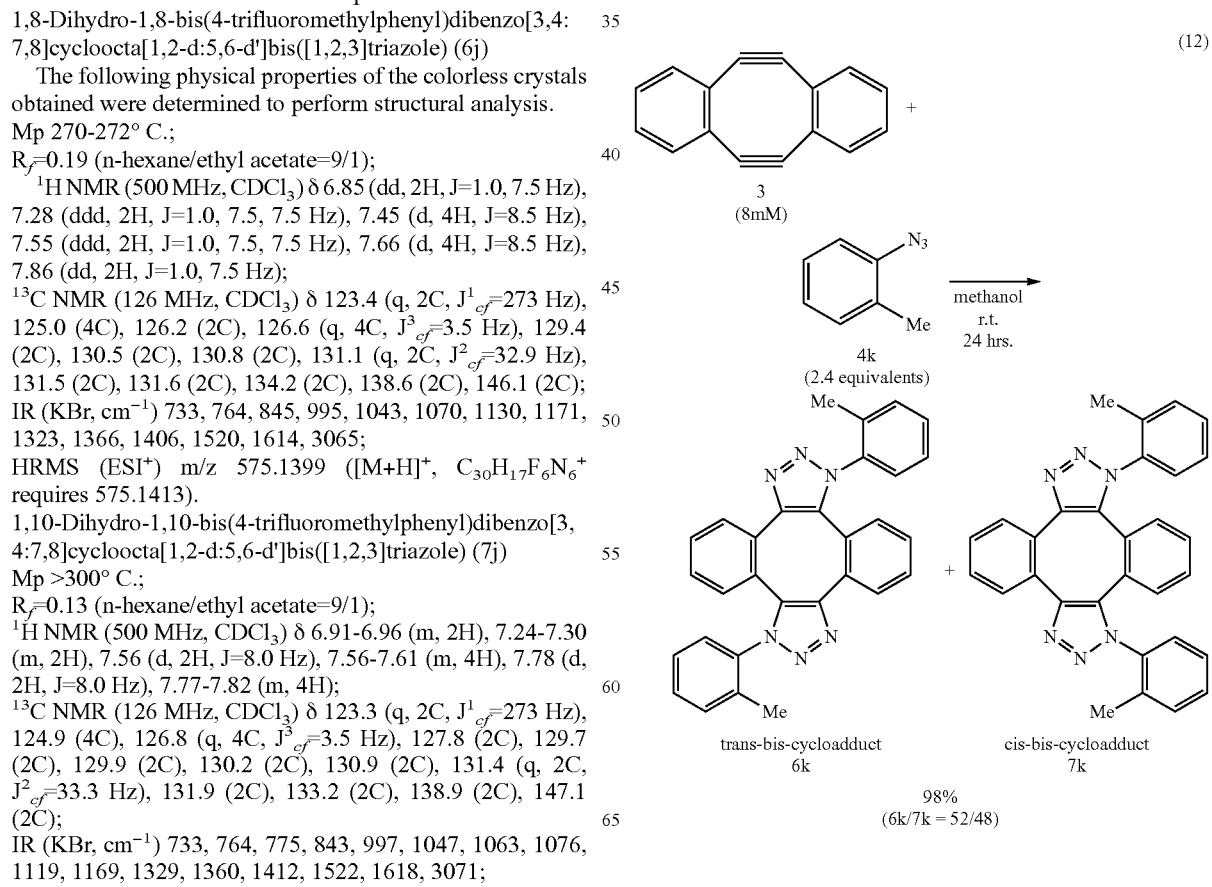

trans-bis-cycloadduct
6k cis-bis-cycloadduct
7k

98%
(6k/7k = 52/48)

As shown in the reaction scheme (12) above, to a solution of diyne 3 (10.0 mg, 50.0 μmol) in methanol (5.00 mL) was added a solution of 2-methylphenyl azide (4k) (16.0 mg, 120 μmol) in methanol (1.25 mL) at room temperature. After stirring for 24 hours at room temperature, the reaction solution was concentrated under reduced pressure. The residue was purified by flash column chromatography (silica-gel 10 g, dichloromethane only to dichloromethane/methanol=9/1) to give a mixture of trans-6k and cis-7k (22.9 mg, 49.1 μmol, 98.3%). The ratio of trans-6k and cis-7k was determined based on the $^1$H NMR spectrum. The geometries of the respective compounds were confirmed by X-ray crystallographical analyses (CCDC 810933 (6k) and CCDC 810840 (7k)).

1,8-Dihydro-1,8-bis(2-methylphenyl)dibenzo[3,4:7,8]cycloocta[1,2-d:5,6-d']bis([1,2,3]triazole) (6k)

The following physical properties of the colorless crystals obtained were determined to perform structural analysis.

Mp >300° C.;

$R_f$=0.36 (dichloromethane/methanol=49/1);

$^1$H NMR (500 MHz, CDCl$_3$) δ 1.88 (br s, 6H), 6.86 (br d, 2H, J=7.5 Hz), 7.17 (ddd, 2H, J=1.0, 1.0, 7.5 Hz), 7.19-7.37 (m, 8H), 7.43 (ddd, 2H, J=1.0, 7.5, 7.5 Hz), 7.77 (dd, 2H, J=1.0, 7.5 Hz);

$^{13}$C NMR (126 MHz, CDCl$_3$) δ 17.5 (2C), 126.4 (2C), 126.7 (2C), 127.9 (2C), 128.6 (2C), 129.9 (2C), 130.0 (2C), 130.4 (2C), 131.2 (2C), 131.3 (2C), 132.1 (2C), 135.09 (2C), 135.10 (2C), 135.8 (2C), 144.8 (2C);

IR (KBr, cm$^{-1}$) 613, 719, 739, 770, 908, 997, 1267, 1362, 1425, 1466, 1497, 1514;

HRMS (ESI$^+$) m/z 467.1958 ([M+H]$^+$, C$_{30}$H$_{23}$N$_6{}^+$ requires 467.1979);

C$_{30}$H$_{22}$N$_6$: Calcd.: C, 77.23; H, 4.75; N, 18.01%; Found: C, 77.19; H, 4.65; N, 17.80%.

1,10-Dihydro-1,10-bis(2-methylphenyl)dibenzo[3,4:7,8]cycloocta[1,2-d:5,6-d']bis([1,2,3]triazole) (7k)

The following physical properties of the colorless crystals obtained were determined to perform structural analysis.

Mp >300° C.;

$R_f$=0.22 (dichloromethane/methanol=49/1);

$^1$H NMR (500 MHz, CDCl$_3$) δ 2.33 (s, 6H), 6.75-6.80 (m, 2H), 7.01 (d, 2H, J=7.5 Hz), 7.03-7.08 (m, 2H), 7.17 (dd, 2H, J=7.5, 7.5 Hz), 7.37 (dd, 2H, J=7.5, 7.5 Hz), 7.40 (d, 2H, J=7.5 Hz), 7.54-7.59 (m, 2H), 7.79-7.84 (m, 2H);

$^{13}$C NMR (126 MHz, CDCl$_3$) δ 18.3 (2C), 126.4 (2C), 127.2 (2C), 127.8 (2C), 129.2 (2C), 129.3 (2C), 130.1 (2C), 130.6 (2C), 130.9 (2C), 131.0 (2C), 131.6 (2C), 134.3 (2C), 135.2 (2C), 135.7 (2C), 145.9 (2C);

IR (KBr, cm$^{-1}$) 611, 718, 737, 762, 781, 999, 1117, 1138, 1263, 1287, 1356, 1429, 1462, 1473, 1497, 1512;

HRMS (ESI$^+$) m/z 467.1979 ([M+H]$^+$, C$_{30}$H$_{23}$N$_6{}^+$ requires 467.1979);

C$_{30}$H$_{22}$N$_6$: Calcd.: C, 77.23; H, 4.75; N, 18.01%; Found: C, 77.22; H, 4.68; N, 17.77%.

EXAMPLE 10

Production 10 of Bis-cycloadducts by SPDC Reaction

[Chemical formula (13)]

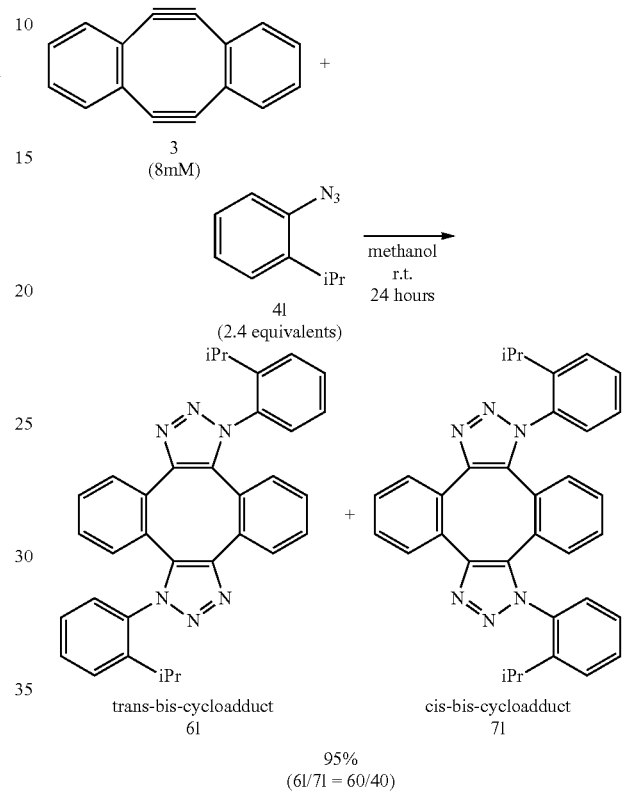

As shown in the reaction scheme (13) above, to a solution of diyne 3 (40.0 mg, 200 μmol) in methanol (22.0 mL) was added a solution of 2-isopropylphenyl azide (41) (77.4 mg, 480 μmol) in methanol (3.0 mL) at room temperature. After stirring for 24 hours at room temperature, the reaction solution was concentrated under reduced pressure. The residue was purified by thin-layer chromatography (n-hexane/ethyl acetate=9/1) to give a mixture of trans-61 and cis-71 (99.5 mg, 190 μmol, 95.3%). The ratio of trans-61 and cis-71 was determined based on the $^1$H NMR spectrum. The geometries of the respective compounds were confirmed by X-ray crystallographical analyses (CCDC 810934 (61) and CCDC 810841 (71)).

1,8-Dihydro-1,8-bis(2-isopropylphenyl)dibenzo[3,4:7,8]cycloocta[1,2-d:5,6-d']bis([1,2,3]triazole) (61)

The following physical properties of the colorless crystals obtained were determined to perform structural analysis.

Mp 298-300° C.;

$R_f$=0.70 (dichloromethane/methanol=24/1);

$^1$H NMR (500 MHz, CDCl$_3$) δ 0.76 (br s, 12H), 2.07 (br s, 2H), 6.95 (br, 2H), 7.17 (dd, 2H, J=7.5, 7.5 Hz), 7.35-7.48 (m, 8H), 7.67 (br, 2H), 7.77 (d, 2H, J=7.5 Hz);

$^{13}$C NMR (126 MHz, CDCl$_3$) δ 21.9 (br, 2C), 24.2 (br, 2C), 27.8 (br, 2C), 126.4 (4C), 126.8 (br, 2C), 128.4 (br, 2C), 128.5 (2C), 129.8 (4C), 130.5 (br, 2C), 131.3 (2C), 132.3 (br, 2C), 133.7 (br, 2C), 135.8 (br, 2C), 144.6 (2C), 145.4 (br, 2C);

IR (KBr, cm$^{-1}$) 611, 735, 766, 783, 908, 995, 1045, 1111, 1211, 1269, 1360, 1454, 1493, 1512, 2967; HRMS (ESI$^+$) m/z 523.2587 ([M+H]$^+$, C$_{34}$H$_{31}$N$_6{}^+$ requires 523.2605);

$C_{34}H_{30}N_6$: Calcd.: C, 78.13; H, 5.79; N, 16.08%; Found: C, 77.90; H, 5.60; N, 15.85%.

1,10-Dihydro-1,10-bis(2-isopropylphenyl)dibenzo[3,4:7,8]cycloocta[1,2-d:5,6-d']bis([1,2,3]triazole) (7l)

The following physical properties of the colorless crystals obtained were determined to perform structural analysis.

Mp >300° C.;

$R_f$=0.48 (dichloromethane/methanol=24/1);

$^1$H NMR (500 MHz, CDCl$_3$) δ 1.35 (br s, 6H), 1.45 (br s, 6H), 3.04 (br s, 2H), 6.72-6.78 (m, 2H), 6.82-6.91 (m, 2H), 6.98-7.06 (m, 2H), 7.07-7.16 (m, 2H), 7.40-7.49 (m, 2H), 7.52-7.61 (m, 4H), 7.79-7.87 (m, 2H);

$^{13}$C NMR (126 MHz, CDCl$_3$) δ 23.1 (2C), 25.2 (2C), 28.6 (2C), 126.0 (2C), 127.1 (2C), 127.5 (2C), 128.0 (2C), 129.1 (2C), 129.2 (2C), 130.4 (2C), 130.7 (2C), 130.9 (2C), 131.0 (2C), 133.9 (2C), 134.5 (2C), 145.8 (2C), 146.6 (2C);

IR (KBr, cm$^{-1}$) 523, 611, 733, 758, 910, 997, 1028, 1092, 1134, 1213, 1261, 1360, 1452, 1495, 1512, 2965;

HRMS (ESI$^+$) m/z 523.2585 ([M+H]$^+$, $C_{34}H_{31}N_6^+$ requires 523.2605).

EXAMPLE 11

Production 11 of Bis-cycloadducts by SPDC Reaction

[Chemical formula (14)]

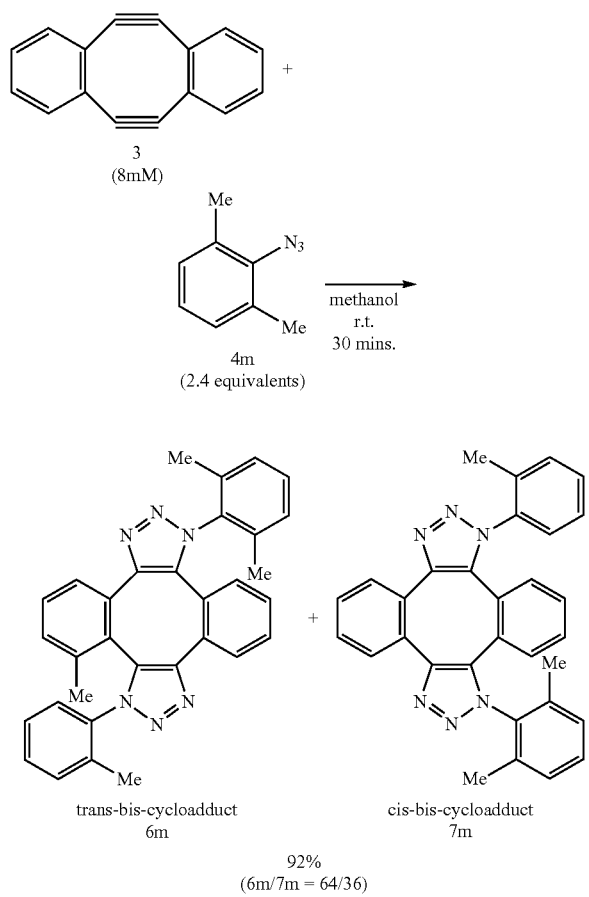

(14)

As shown in the reaction scheme (14) above, to a solution of diyne 3 (10.0 mg, 50 μmol) in methanol (5.00 mL) was added a solution of 2,6-dimetylphenyl azide (4m) (17.7 mg, 120 μmol) in methanol (1.25 mL) at room temperature. After stirring for 30 minutes at room temperature, the reaction solution was concentrated under reduced pressure. The residue was purified by flash column chromatography (silica-gel 10 g, dichloromethane/methanol=9/1) to give a mixture of trans-6m and cis-7m (22.7 mg, 45.9 μmol, 91.9%). The ratio of trans-6m and cis-7m was determined based on the $^1$H NMR spectrum. The geometries of the respective compounds were confirmed by X-ray crystallographical analyses (CCDC 810935 (6m) and CCDC 810842 (7m)).

1,8-Bis(2,6-dimethylphenyl)-1,8-dihydrodibenzo[3,4:7,8]cycloocta[1,2-d:5,6-d']bis([1,2,3]triazole) (6m)

The following physical properties of the colorless crystals obtained were determined to perform structural analysis.

Mp >300° C.;

$R_f$=0.49 (dichloromethane/methanol=49/1);

$^1$H NMR (500 MHz, CDCl$_3$) δ 1.53 (s, 6H), 2.41 (s, 6H), 6.87 (dd, 2H, J=1.0, 7.5 Hz), 6.94 (dd, 2H, J=5.0, 5.0 Hz), 7.19 (ddd, 2H, J=1.0, 7.5, 7.5 Hz), 7.23 (d, 2H, J=5.0 Hz), 7.23 (d, 2H, J=5.0 Hz), 7.43 (ddd, 2H, J=1.0, 7.5, 7.5 Hz), 7.77 (dd, 2H, J=1.0, 7.5 Hz);

$^{13}$C NMR (126 MHz, CDCl$_3$) δ 17.3 (2C), 18.4 (2C), 126.4 (2C), 128.4 (2C), 128.5 (2C), 128.6 (2C), 129.4 (2C), 129.9 (2C), 130.0 (2C), 131.4 (2C), 132.0 (2C), 134.3 (2C), 135.7 (2C), 135.8 (2C), 136.1 (2C), 144.7 (2C);

IR (KBr, cm$^{-1}$) 735, 764, 781, 912, 995, 1113, 1354, 1427, 1474, 1512;

HRMS (ESI$^+$) m/z 495.2276 ([M+H]$^+$, $C_{32}H_{27}N_6^+$ requires 495.2292);

$C_{32}H_{26}N_6$: Calcd.: C, 77.71; H, 5.30; N, 16.99%; Found: C, 77.95; H, 5.41; N, 16.88%.

1,10-Bis(2,6-dimethylphenyl)-1,10-dihydrodibenzo[3,4:7,8]cycloocta[1,2-d:5,6-d']bis([1,2,3]triazole) (7m)

The following physical properties of the colorless crystals obtained were determined to perform structural analysis.

Mp >300° C.;

$R_f$=0.24 (dichloromethane/methanol=49/1);

$^1$H NMR (500 MHz, CDCl$_3$) δ 1.76 (s, 6H), 2.23 (s, 6H), 6.87-6.93 (m, 2H), 7.00 (d, 2H, J=7.5 Hz), 7.03-7.08 (m, 2H), 7.22-7.29 (m, 4H), 7.53-7.58 (m, 2H), 7.74-7.79 (m, 2H);

$^{13}$C NMR (126 MHz, CDCl$_3$) δ 18.4 (2C), 18.8 (2C), 127.0 (2C), 128.2 (2C), 128.8 (2C), 129.1 (2C), 129.3 (2C), 130.2 (2C), 130.6 (2C), 130.7 (2C), 131.1 (2C), 134.2 (2C), 134.8 (2C), 135.3 (2C), 137.3 (2C), 146.1 (2C);

IR (KBr, cm$^{-1}$) 704, 733, 764, 918, 995, 1134, 1267, 1290, 1346, 1474, 1508;

HRMS (ESI$^+$) m/z 495.2315 ([M+H]$^+$, $C_{32}H_{27}N_6^+$ requires 495.2292);

$C_{32}H_{26}N_6$: Calcd.: C, 77.71; H, 5.30; N, 16.99%; Found: C, 77.59; H, 5.33; N, 16.73%.

EXAMPLE 12

Production 12 of Bis-cycloadducts by SPDC Reaction

[Chemical formula (15)]

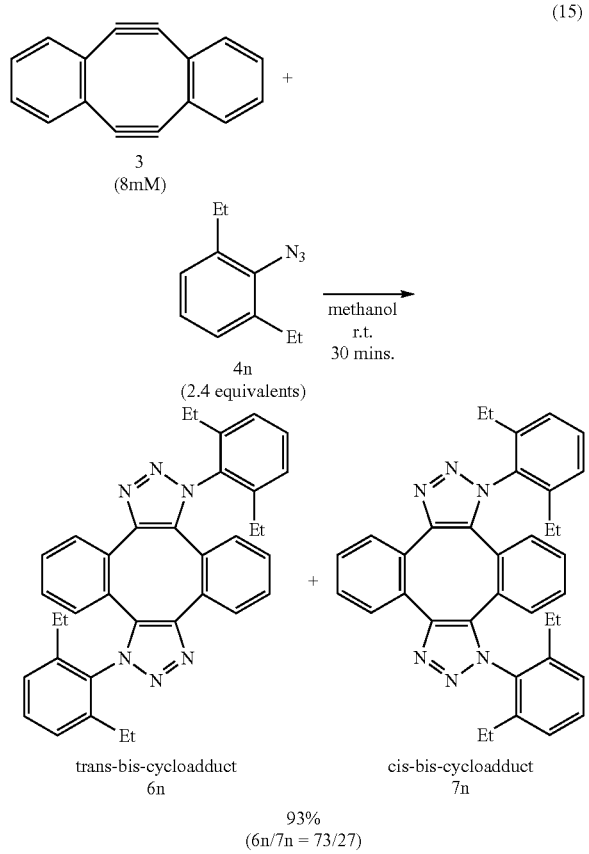

As shown in the reaction scheme (15) above, to a solution of diyne 3 (10.0 mg, 50 μmol) in methanol (5.00 mL) was added a solution of 2,6-dietylphenyl azide (4n) (21.0 mg, 120 μmol) in methanol (1.25 mL) at room temperature. After stirring for 30 minutes at room temperature, the reaction solution was concentrated under reduced pressure. The residue was purified by flash column chromatography (silica-gel 10 g, dichloromethane only to dichloromethane/methanol=24/1) to give a mixture of trans-6n and cis-7n (25.7 mg, 46.7 μmol, 93.4%). The ratio of trans-6n and cis-7n was determined based on the $^1$H NMR spectrum. The geometries of the respective compounds were confirmed by X-ray crystallographical analyses (CCDC 810936 (6n) and CCDC 810843 (7n)).

1,8-Bis(2,6-diethylphenyl)-1,8-dihydrodibenzo[3,4:7,8]cycloocta[1,2-d:5,6-d']bis([1,2,3]triazole) (6n)

The following physical properties of the colorless crystals obtained were determined to perform structural analysis.
Mp 255-257° C.;
$R_f$=0.57 (dichloromethane/methanol=49/1);
$^1$HNMR (500 MHz, CDCl$_3$) δ 0.73 (dd, 6H, J=7.5, 7.5 Hz), 1.41 (dd, 6H, J=7.5, 7.5 Hz), 1.74 (dq, 2H, J=7.5, 15.0 Hz), 1.92 (dq, 2H, J=7.5, 15.0 Hz), 2.59 (dq, 2H, J=7.0, 14.0 Hz), 2.64 (dq, 2H, J=7.0, 14.0 Hz), 6.85 (dd, 2H, J=1.0, 7.5 Hz), 7.00 (d, 2H, J=7.5 Hz), 7.17 (ddd, 2H, J=1.0, 7.5, 7.5 Hz), 7.30 (d, 2H, J=7.5 Hz), 7.35 (dd, 2H, J=7.5, 7.5 Hz), 7.41 (ddd, 2H, J=1.0, 7.5, 7.5 Hz) 7.76 (dd, 2H, J=1.0, 7.5 Hz);
$^{13}$C NMR (126 MHz, CDCl$_3$) δ 13.5 (2C), 15.2 (2C), 24.0 (2C), 24.7 (2C), 126.45 (2C), 126.49 (2C), 126.57 (2C), 128.5 (2C), 129.4 (2C), 129.9 (2C), 130.3 (2C), 131.4 (2C), 132.2 (2C), 133.15 (2C), 135.9 (2C), 141.0 (2C), 142.1 (2C), 144.6 (2C);
IR (KBr, cm$^{-1}$) 733, 758, 910, 995, 1358, 1466, 1510, 2876, 2936, 2970;
HRMS (ESI$^+$) m/z 551.2912 ([M+H]$^+$, C$_{36}$H$_{35}$N$_6$$^+$ requires 551.2918);
C$_{36}$H$_{34}$N$_6$: Calcd.: C, 78.52; H, 6.22; N, 15.26%; Found: C, 78.26; H, 6.47; N, 14.97%.

1,10-Bis(2,6-diethylphenyl)-1,10-dihydrodibenzo[3,4:7,8]cycloocta[1,2-d:5,6-d']bis([1,2,3]triazole) (7n)

The following physical properties of the colorless crystals obtained were determined to perform structural analysis.
Mp >300° C.;
$R_f$=0.30 (dichloromethane/methanol=49/1);
$^1$H NMR (500 MHz, CDCl$_3$) δ 0.91 (dd, 6H, J=7.5, 7.5 Hz), 1.32 (dd, 6H, J=7.5, 7.5 Hz), 2.04 (dq, 2H, J=7.5, 15.0 Hz), 2.09 (dq, 2H, J=7.5, 15.0 Hz), 2.26 (dq, 2H, J=7.5, 15.0 Hz), 2.41 (dq, 2H, J=7.5, 15.0 Hz), 6.83-6.87 (m, 2H), 6.96-7.01 (m, 2H), 7.08 (d, 2H, J=7.5 Hz), 7.31 (d, 2H, J=7.5 Hz), 7.40 (dd, 2H, J=7.5, 7.5 Hz), 7.53-7.57 (m, 2H), 7.74-7.79 (m, 2H);
$^{13}$C NMR (126 MHz, CDCl$_3$) δ 14.9 (2C), 15.2 (2C), 24.7 (2C), 25.3 (2C), 126.7 (2C), 126.8 (2C), 126.9 (2C), 129.0 (2C), 129.1 (2C), 130.6 (2C), 130.7 (2C), 130.8 (2C), 131.2 (2C), 133.6 (2C), 134.2 (2C), 140.9 (2C), 143.3 (2C), 145.9 (2C);
IR (KBr, cm$^{-1}$) 733, 758, 783, 908, 993, 1061, 1113, 1128, 1261, 1352, 1470, 1508, 2872, 2932, 2965;
HRMS (ESI$^+$) m/z 551.2940 ([M+H]$^+$, C$_{36}$H$_{35}$N$_6$$^+$ requires 551.2918);
C$_{36}$H$_{34}$N$_6$: Calcd.: C, 78.52; H, 6.22; N, 15.26%; Found: C, 78.49; H, 6.20; N, 15.03%.

EXAMPLE 13

Production 13 of Bis-cycloadducts by SPDC Reaction

[Chemical formula (16)]

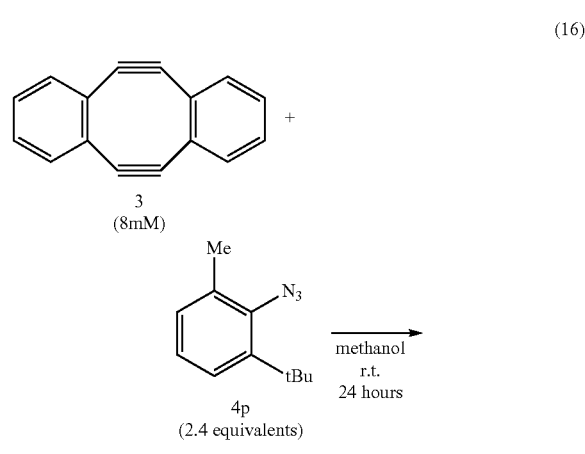

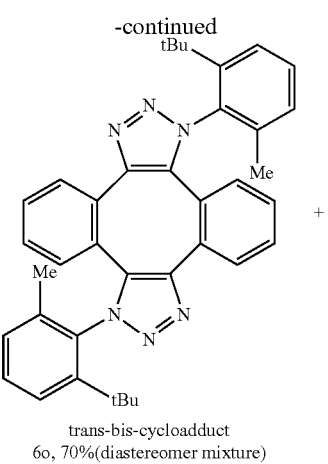

trans-bis-cycloadduct
6o, 70%(diastereomer mixture)

+

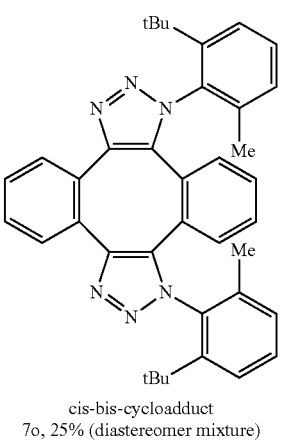

cis-bis-cycloadduct
7o, 25% (diastereomer mixture)

As shown in the reaction scheme (16) above, to a solution of diyne 3 (20.3 mg, 102 μmol) in methanol (9.0 mL) was added a solution of 2-t-butyl-6-methylphenyl azide (4o) (45.4 mg, 240 μmol) in methanol (3.5 mL) at room temperature. After stirring for 24 hours at room temperature, the reaction solution was concentrated under reduced pressure. The residue was purified by flash column chromatography (silica-gel 10 g, hexane only to ethyl acetate) to give a mixture of diastereomers of trans-6o and cis-7o (58.4 mg, 101 μmol, 99.7%).

1,8-Bis(2-tert-butyl-6-methylphenyl)-1,8-dihydrodibenzo[3,4:7,8]cycloocta[1,2-d:5,6-d']bis([1,2,3]triazole) (6o, a Mixture of Diastereomers)

The following physical properties of the colorless crystals obtained were determined to perform structural analysis.

$R_f$=0.47 (dichloromethane/methanol=3/1);

$^1$H NMR (400 MHz, CDCl$_3$) (major isomer) δ 0.87 (s, 18H), 2.07 (s, 6H), 6.77 (dd, 2H, J=1.2, 8.0 Hz), 7.13 (ddd, 2H, J=1.2, 7.6, 7.6 Hz), 7.23-7.26 (m, 2H), 7.34-7.36 (m, 4H), 7.39 (dd, 2H, J=1.2, 8.0 Hz), 7.69 (dd, 2H, J=1.2, 7.6 Hz).

1,10-Bis(2-tert-butyl-6-methylphenyl)-1,10-dihydrodibenzo[3,4:7,8]cycloocta[1,2-d:5,6-d']bis([1,2,3]triazole) (7o, a Mixture of Diastereomers)

The following physical properties of the colorless crystals obtained were determined to perform structural analysis.

$R_f$=0.30 (dichloromethane/methanol=3/1);

$^1$H NMR (400 MHz, CDCl$_3$) (major isomer) δ 0.93 (s, 18H), 1.80 (s, 6H), 6.98-7.02 (m, 2H), 7.30-7.42 (m, 6H), 7.51-7.57 (m, 4H), 7.63-7.67 (m, 2H).

EXAMPLE 14

Production 14 of Bis-cycloadducts by SPDC Reaction

[Chemical formula (17)]

(17)

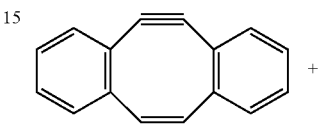

3
(8mM)

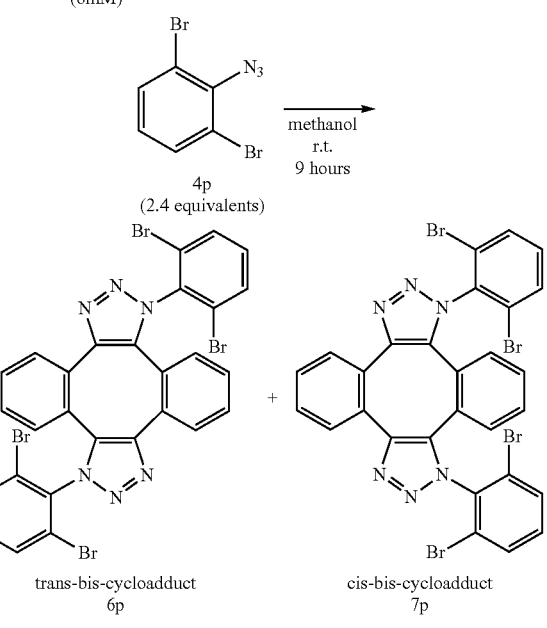

trans-bis-cycloadduct
6p

+ cis-bis-cycloadduct
7p

99%
(6p/7p = 63/37)

As shown in the reaction scheme (17) above, to a solution of diyne 3 (20.0 mg, 100 μmol) in methanol (12.5 mL) was added 2,6-dibromophenyl azide (4p) (66.5 mg, 240 μmol) at room temperature. After stirring for 9 hours at room temperature, the reaction solution was concentrated under reduced pressure. The residue was purified by thin-layer chromatography (dichloromethane) to give a mixture of trans-6p and cis-7p (74.3 mg, 98.7 μmol, 98.7%). The ratio of trans-6p and cis-7p was determined based on the $^1$H NMR spectrum.

1,8-Bis(2,6-dibromophenyl)-1,8-dihydrodibenzo[3,4:7,8]cycloocta[1,2-d:5,6-d']bis([1,2,3]triazole) (6p)

The following physical properties of the colorless crystals obtained were determined to perform structural analysis.

$R_f$=0.07 (dichloromethane);

$^1$H NMR (400 MHz, CDCl$_3$) δ 7.16-7.27 (m, 6H), 7.46-7.48 (m, 4H), 7.75 (dd, 2H, J=1.2, 8.4 Hz), 782 (dd, 2H, J=0.8, 7.6 Hz).

1,10-Bis(2,6-dibromolphenyl)-1,10-dihydrodibenzo[3,4:7,8]cycloocta[1,2-d:5,6-d']bis([1,2,3]triazole) (7p)

The following physical properties of the colorless crystals obtained were determined to perform structural analysis.
$R_f$=0.01 (dichloromethane);
$^1$H NMR (400 MHz, CDCl$_3$) δ 7.16 (dd, 2H, J=3.6, 6.0 Hz), 7.22-7.30 (m, 4H), 7.53-7.57 (m, 4H), 7.75-7.79 (m, 4H).

EXAMPLE 15

Production 15 of Bis-cycloadducts by SPDC Reaction

[Chemical formula (18)]

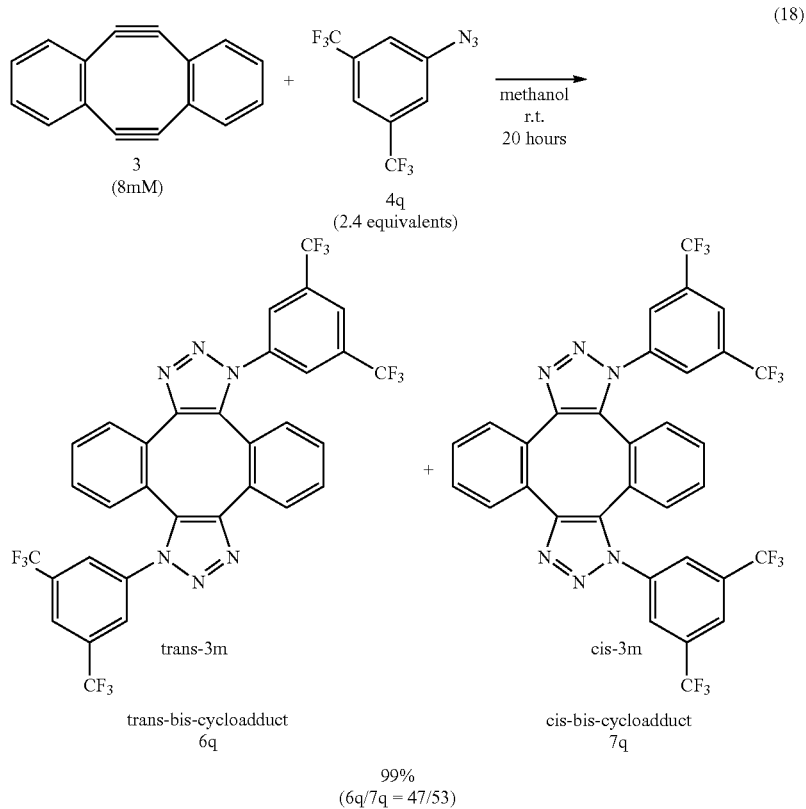

As shown in the reaction scheme (18) above, to a solution of diyne 3 (20.4 mg, 102 μmol) in methanol (9.0 mL) was added a solution of 3,5-bis(trifluoromethyl)phenyl azide (4q) (61.2 mg, 240 μmol) in methanol (3.5 mL) at room temperature. After stirring for 20 hours at room temperature, the reaction solution was concentrated under reduced pressure. The residue was purified by thin-layer chromatography (dichloromethane/hexane=3/1) to give a mixture of trans-6q and cis-7q (71.6 mg, 101 μmol, 99.0%). The ratio of trans-6q and cis-7q was determined based on the $^1$H NMR spectrum. 1,8-Bis[3,5-bis(trifluoromethyl)phenyl]-1,8-dihydrodibenzo [3,4:7, 8]cycloocta[1,2-d:5,6-d']bis([1,2,3]triazole) (6q)

The following physical properties of the colorless crystals obtained were determined to perform structural analysis.
$^1$H NMR (400 MHz, CDCl$_3$) δ 6.84 (dd, 2H, J=0.8, 8.0 Hz), 7.32 (ddd, 2H, J=1.2, 7.6, 7.6 Hz), 7.60 (ddd, 2H, J=1.2, 7.6, 7.6 Hz), 7.75 (s, 4H), 7.90-7.93 (m, 4H).
1,10-Bis[3,5-bis(trifluoromethyl)phenyl]-1,10-dihydrodibenzo[3,4:7,8]cycloocta[1,2-d:5,6-d']bis([1,2,3]triazole) (7q)

The following physical properties of the colorless crystals obtained were determined to perform structural analysis.
$^1$H NMR (400 MHz, CDCl$_3$) δ 7.00-7.03 (m, 2H), 7.34-7.38 (m, 2H), 7.58-7.61 (m, 2H), 7.75-7.78 (m, 2H), 7.88 (d, 4H, J=1.6 Hz), 7.99 (s, 2H).

EXAMPLE 16

Production 16 of Bis-cycloadducts by SPDC Reaction

[Chemical formula (19)]

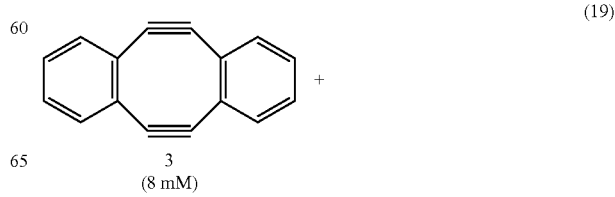

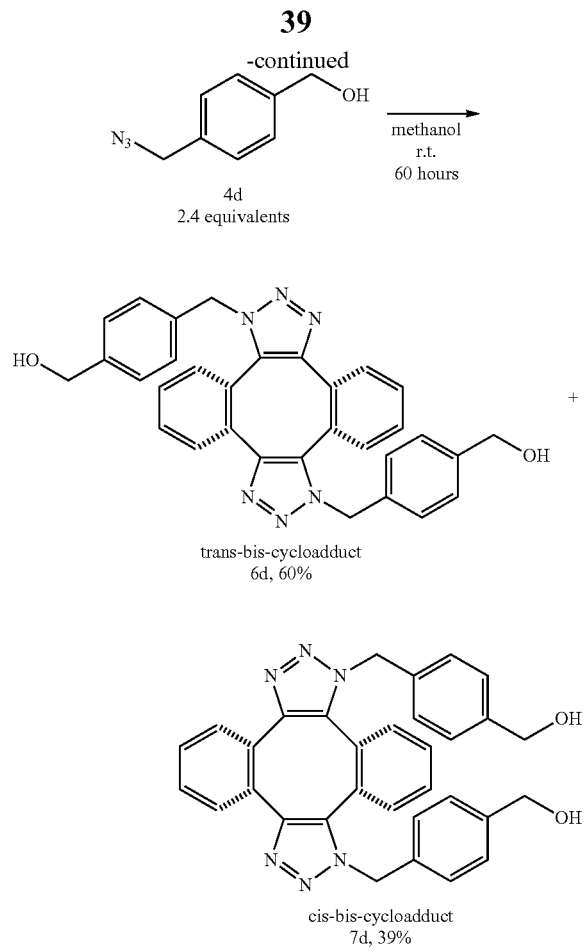

As shown in the reaction scheme (19) above, to a solution of diyne 3 (40.0 mg, 200 μmol) in methanol (23.5 mL) was added a solution of 4-(azidomethyl)benzyl alcohol (4d, synthesized by the method described in Non-Patent Document M. Smet, K. Metten, W. Dehaen, Collect. Czech. Chem. Commun. 2004, 69, 1097-1108) (78.3 mg, 480 μmol) in methanol (1.5 mL) at room temperature. After stirring for 60 minutes at the same temperature, the reaction solution was concentrated under reduced pressure using an evaporator. The residue was purified by flash column chromatography (silica-gel 10 g, dichloromethane/methanol=29/1) to give two regioisomeric bis-cycloadducts of trans-6d (63.5 mg, 121 μmol, 60.3%) and cis-7d (40.9 mg, 77.7 μmol, 38.9%). The geometries of the respective compounds were confirmed by X-ray crystallographical analyses (CCDC 759899 (6d) and CCDC 759904 (7d)).

1,8-Dihydro-1,8-bis[4-(hydroxylmethyl)benzyl]dibenzo[3,4:7,8]cycloocta[1,2-d:5,6-d']bis([1,2,3]triazole) (6d)

Recrystallization from dichloromethane/methanol gave colorless crystals. The following physical properties of the crystals were measured to conduct structural analysis.

Mp >300° C. (dec.);
$R_f$=0.45 (hexane/ethyl acetate=1/9);
$^1$H NMR (300 MHz, CDCl$_3$) δ 3.38 (br s, 2H), 4.52-4.70 (m, 4H), 5.27 (d, 2H, J=14.7 Hz), 5.29 (d, 2H, J=14.7 Hz), 6.52-6.62 (AA'BB'×2, 4H), 7.06-7.13 (AA'BB'×2, 4H), 7.13-7.20 (m, 2H), 7.38-7.57 (m, 6H);

$^{13}$C NMR (75.5 MHz, CDCl$_3$) δ 51.0 (2C), 62.4 (2C), 126.2 (4C), 126.5 (4C), 129.3 (2C), 130.1 (2C), 130.3 (2C), 130.9 (2C), 132.1 (2C), 134.0 (2C), 134.5 (2C), 142.1 (2C), 144.5 (2C), 147.7 (2C);
IR (KBr, cm$^{-1}$) 519, 594, 775, 986, 1028, 1105, 1132, 1215, 1252, 1314, 1352, 1422, 1474, 1514, 1616, 2097, 2868, 3366;
HRMS (ESI$^+$) m/z 527.2191 ([M+H]$^+$, C$_{32}$H$_{27}$N$_6$O$_2^+$ Calcd. 527.2190).

1,10-Dihydro-1,10-bis[4-(hydroxylmethyl)benzyl]dibenzo[3,4:7,8]cycloocta[1,2-d:5,6-d']bis([1,2,3]triazole) (7d)

Recrystallization from dichloromethane/methanol gave colorless crystals. The following physical properties of the crystals were measured to conduct structural analysis.

Mp >300° C. (dec.);
$R_f$=0.39 (hexane/ethyl acetate=1/9);
$^1$H NMR (300 MHz, CDCl$_3$) δ 2.03 (t, 2H, J=5.2 Hz), 4.66 (d, 4H, J=5.2 Hz), 4.96 (d, 2H, J=15.7 Hz), 5.33 (d, 2H, J=15.7 Hz), 6.90-7.00 (AA'BB'×2, 4H), 7.08-7.16 (m, 2H) 7.20-7.32 (AA'BB'×2, 4H), 7.40-7.52 (m, 4H), 7.62-7.70 (m, 2H);
$^{13}$C NMR (75.5 MHz, CDCl$_3$) δ 51.3 (2C), 62.5 (2C), 126.8 (4C), 127.0 (2C), 127.1 (4C), 129.2 (2C), 130.2 (2C), 130.3 (2C), 130.7 (2C), 130.8 (2C), 133.5 (2C), 133.8 (2C), 142.5 (2C), 145.0 (2C);
IR (KBr, cm$^{-1}$), 704, 737, 764, 986, 1028, 1134, 1209, 1248, 1265, 1287, 1315, 1346, 1422, 1514, 1634, 2089, 3360;
HRMS (ESI$^+$) m/z 527.2205 ([M+H]$^+$, C$_{32}$H$_{27}$N$_6$O$_2^+$ Calcd. 527.2190).

EXAMPLE 17

Production 17 of Bis-cycloadducts by SPDC Reaction

[Chemical formula (20)]

(20)

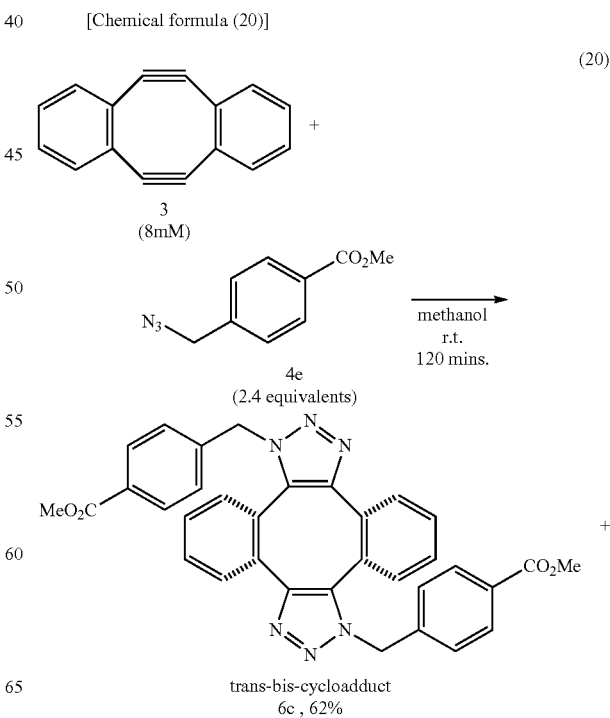

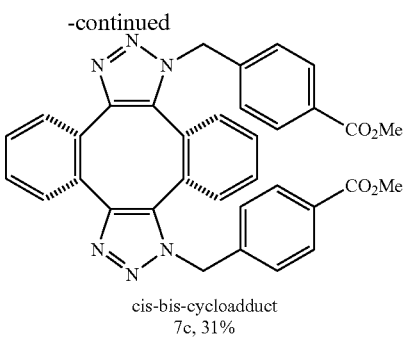

cis-bis-cycloadduct
7c, 31%

As shown in the reaction scheme (20) above, to a solution of diyne 3 (40.0 mg, 200 μmol) in methanol (23.5 mL) was added a solution of methyl 4-(azidomethyl)benzoate (4e, synthesized by the method described in Non-Patent Document E. A. Wydysh, S. M. Medghalchi, A. Vadlamudi, and C. A. Townsend, J. Med. Chem. 2009, 52, 3317-3327) (91.8 mg, 480 μmol) in methanol (1.5 mL) at room temperature. After stirring for 120 minutes at the same temperature, the reaction solution was concentrated under reduced pressure using an evaporator. The residual solid was placed on a Kiriyama funnel and washed with ethyl acetate to give pure cis-bis-cycloadduct 7e (36.1 mg, 61.9 μmol, 30.9%) as one of the two bis-cycloadduct regioisomers. The filtrate was concentrated under reduced pressure using an evaporator and the residue was purified by flash column chromatography (silica-gel 10 g, hexane/ethyl acetate=1/2 to ethyl acetate only) to give trans-bis-cycloadduct 6e (71.8 mg, 123 μmol, 61.5%). The geometries of these compounds were confirmed by their reduction of the esters to the corresponding diols 6d and 7d, respectively, using LiAlH$_4$ in THF (0° C. to heating under reflux, 7.5 hours).

1,8-Dihydro-1,8-bis[4-(methoxycarbonyl)benzyl]dibenzo[3,4:7,8]cycloocta[1,2-d:5,6-d']bis([1,2,3]triazole) (6e)

The following physical properties of the colorless solid obtained were measured to conduct structural analysis.
Mp 102-104° C.;
$R_f$=0.31 (hexane/ethyl acetate=2/1);
$R_f$=0.27 (dichloromethane/methanol=15/1);
$^1$H NMR (300 MHz, CDCl$_3$) δ 3.90 (s, 6H), 5.34 (d, 2H, J=15.9 Hz), 5.57 (d, 2H, J=15.9 Hz), 7.03 (d, 2H, J=7.6 Hz), 7.05-7.12 (AA'BB'×2, 4H), 7.39 (dd, 2H, J=7.6, 7.6 Hz), 7.54 (dd, 2H, J=7.6, 7.6 Hz), 7.73 (d, 2H, J=7.6 Hz), 7.91-8.00 (AA'BB'×2, 4H);
$^{13}$C NMR (75.5 MHz, CDCl$_3$) δ 51.0 (2C), 52.1 (2C), 126.0 (2C), 126.5 (4C), 128.9 (2C), 129.3 (4C), 129.4 (2C), 130.1 (2C), 130.4 (2C), 130.7 (2C), 131.8 (2C), 134.6 (2C), 140.9 (2C), 144.8 (2C), 165.6 (2C);
IR (KBr, cm$^{-1}$) 581, 735, 746, 764, 806, 910, 1020, 1111, 1180, 1283, 1352, 1435, 1516, 1614, 1719, 2951;
HRMS (ESI$^+$) m/z 583.2104 ([M+H]$^+$, C$_{34}$H$_{27}$N$_6$O$_4^+$ Calcd. 583.2088).

1,10-Dihydro-1,10-bis[4-(methoxycarbonyl)benzyl]dibenzo[3,4:7,8]cycloocta[1,2-d:5,6-d']bis([1,2,3]triazole) (7e)

The following physical properties of the colorless solid obtained were measured to conduct structural analysis.
Mp 287-290° C.;
$R_f$=0.31 (hexane/ethyl acetate=2/1);
$R_f$=0.27 (dichloromethane/methanol=15/1);
$^1$H NMR (300 MHz, CDCl$_3$) δ 3.91 (s, 6H), 4.98 (d, 2H, J=15.9 Hz), 5.36 (d, 2H, J=15.9 Hz), 6.98-7.11 (m, 6H), 7.38-7.45 (m, 2H), 7.46-7.56 (m, 2H), 7.64-7.72 (m, 2H), 7.94-8.00 (AA'BB'×2, 4H);
$^{13}$C NMR (75.5 MHz, CDCl$_3$) δ 51.7 (2C), 52.4 (2C), 127.1 (4C), 127.8 (2C), 129.3 (2C), 130.06 (2C), 130.14 (2C), 130.2 (4C), 130.3 (2C), 130.4 (2C), 130.6 (2C), 133.5 (2C), 140.1 (2C), 146.3 (2C), 166.3 (2C);
IR (KBr, cm$^{-1}$) 582, 735, 750, 764, 804, 910, 1020, 1111, 1180, 1283, 1435, 1516, 1614, 1719, 2951;
HRMS (ESI$^+$) m/z 583.2092 ([M+H]$^+$, C$_{34}$H$_{27}$N$_6$O$_4^+$ Calcd. 583.2088).

EXAMPLE 18

Production 18 of Bis-cycloadducts by SPDC Reaction

[Chemical formula (21)]

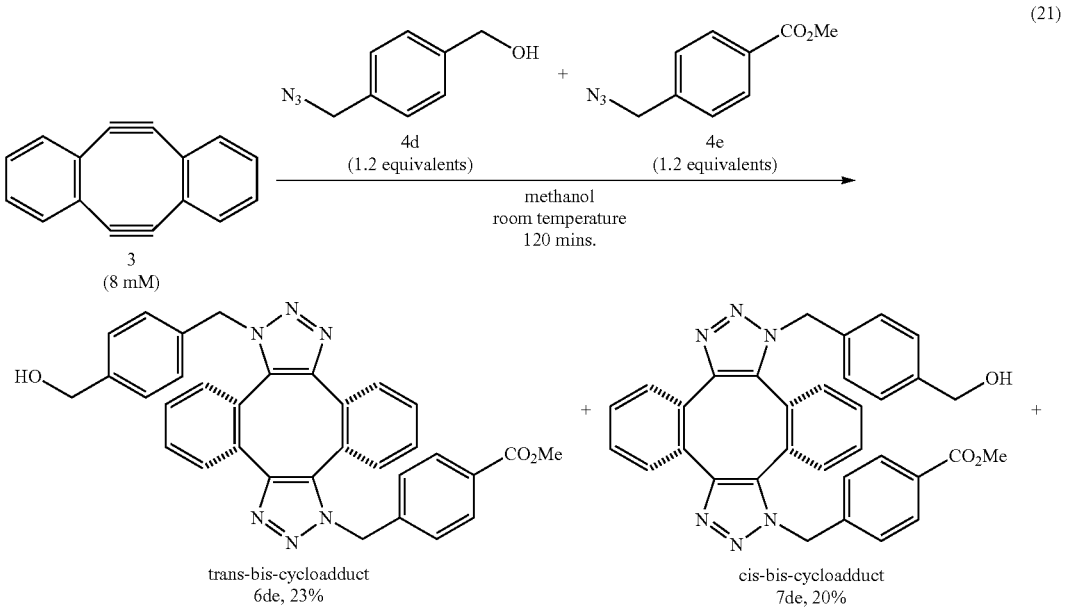

(21)

trans-bis-cycloadduct
6de, 23% cis-bis-cycloadduct
7de, 20%

-continued

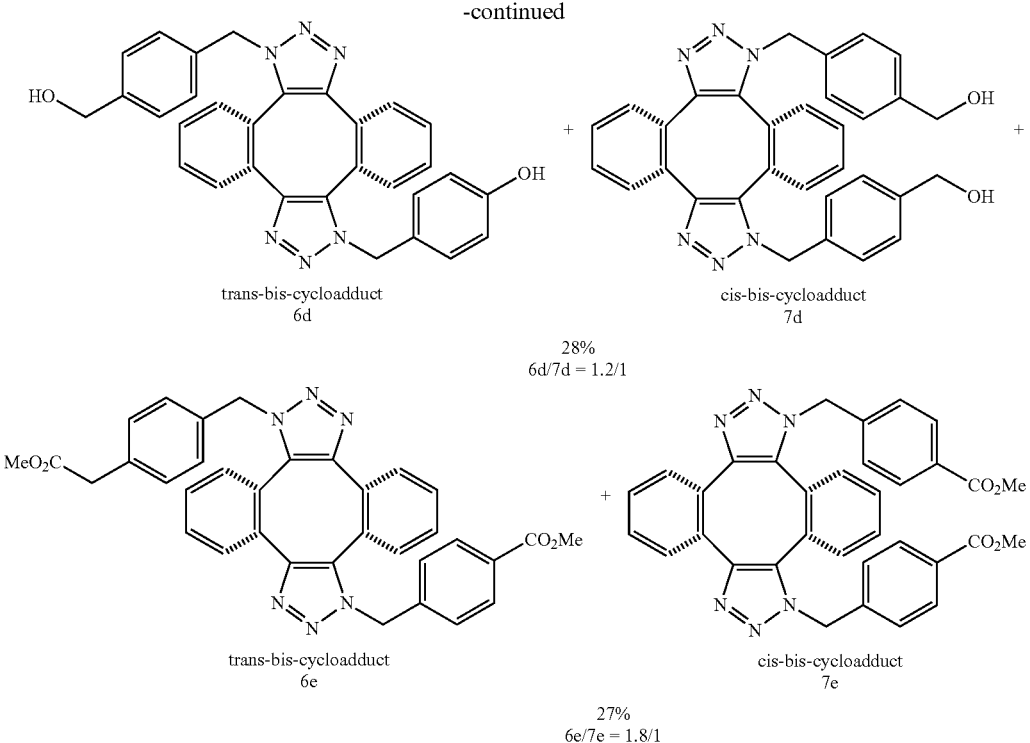

trans-bis-cycloadduct
6d cis-bis-cycloadduct
7d

28%
6d/7d = 1.2/1 trans-bis-cycloadduct
6e cis-bis-cycloadduct
7e

27%
6e/7e = 1.8/1

As illustrated in the reaction scheme (21), to a solution of diyne 3 (40.0 mg, 200 μmol) in methanol (22 mL) was added a mixture of 4-(azidomethyl)benzyl alcohol (4d) (39.2 mg, 240 μmol) and methyl 4-(azidomethyl)benzoate (4e) (45.9 mg, 240 μmol) in methanol (3 mL) at room temperature. After stirring for 120 minutes at the same temperature, the reaction solution was concentrated under reduced pressure using an evaporator. The residue was then purified by flash column chromatography (silica-gel 10 g, hexane/ethyl acetate=1/1 to 1/4 to ethyl acetate only) to give two regioisomeric hetero or unsymmetrical bis-cycloadducts of trans-6de (21.8 mg, 39.3 μmol, 19.7%) and cis-7de (25.3 mg, 45.6 μmol, 22.8%). In addition, two pairs of the homo or symmetrical bis-cycloadducts of trans-6d/cis-7d (29.2 mg, 55.5 μmol, 27.8%, 6d/7d=1.8/1) and trans-6e/cis-7e (31.4 mg, 53.9 μmol, 27.0%, 6e/7e=1.2/1) were obtained as a mixture of regioisomers, respectively. The isomeric ratios in the regioisomers were determined by comparing the integration ratios of benzylic proton peaks on $^1$H NMR spectrum. The geometries of 6de and 7de were confirmed by reduction of the esters to the corresponding diols 6d and 7d, respectively, through reaction with lithium aluminum hydride (LiAlH$_4$) in tetrahydrofuran (THF) (0° C. to heating under reflux, 7.5 hours).

1,8-Dihydro-1-[4-(hydroxylmethyl)benzyl]-8-[4-(methoxycarbonyl)benzyl]dibenzo[3,4:7,8]cycloocta[1,2-d:5,6-d]bis([1,2,3]triazole) (6de)

The following physical properties of the colorless solid obtained were determined to perform structural analysis.
Mp 116-118° C.;
$R_f$=0.30 (hexane/ethyl acetate=1/4);
$^1$H NMR (300 MHz, CDCl$_3$) δ 3.16 (br s, 1H), 3.91 (s, 3H), 4.60 (s, 2H), 5.28-5.40 (m, 2H), 5.51 (d, 1H, J=15.5 Hz), 5.61 (d, 1H, J=15.5 Hz), 6.64-6.72 (AA'BB', 2H), 6.92-7.03 (m, 3H), 7.05-7.12 (AA'BB', 2H), 7.23 (d, 1H, J=7.3 Hz), 7.38 (dd, 1H, J=7.3, 7.3 Hz), 7.42-7.62 (m, 4H), 7.71 (d, 1H, J=7.3 Hz), 7.90-7.98 (AA'BB', 2H);
$^{13}$C NMR (75.5 MHz, CDCl$_3$) δ 51.6, 52.1, 52.6, 64.8, 126.0, 126.5, 126.6 (2C), 127.2 (2C), 127.8 (2C), 128.8, 128.9, 129.67, 129.71, 130.0, 130.1 (3C), 130.4, 131.0, 131.2, 131.9, 132.5, 133.7, 134.7, 134.9, 139.9, 141.3, 144.6, 145.2, 166.4;
IR (KBr, cm$^{-1}$) 583, 748, 961, 986, 1018, 1049, 1109, 1182, 1215, 1281, 1352, 1435, 1514, 1614, 1719, 2068, 2359, 3389;
HRMS (ESI) m/z 555.2150 ([M+H]$^+$, C$_{33}$H$_{27}$N$_6$O$_3$$^+$ Calcd. 555.2139).

1,10-Dihydro-1-[4-(hydroxylmethyl)benzyl]-10-[4-(methoxycarbonyl)benzyl]dibenzo[3,4:7,8]cycloocta[1,2-d:5,6-d']bis([1,2,3]triazole) (7de)

The following physical properties of the colorless crystals obtained were determined to perform structural analysis.
Mp 134-136° C.;
$R_f$=0.38 (hexane/ethyl acetate=1/4);
$^1$H NMR (300 MHz, CDCl$_3$) δ 1.90 (t, 1H, J=5.4 Hz), 3.90 (s, 3H), 4.68 (d, 2H, J=5.4 Hz), 4.89 (d, 1H, J=16.0 Hz), 5.04 (d, 1H, J=16.0 Hz), 5.33 (d, 1H, J=16.0 Hz), 5.39 (d, 1H, J=16.0 Hz), 6.88-6.96 (AA'BB', 2H), 7.00 (d, 1H, J=7.6 Hz), 7.04-7.10 (AA'BB', 2H), 7.15 (d, 1H, J=7.6 Hz), 7.24-7.32 (AA'BB', 2H), 7.34-7.54 (m, 4H), 7.62-7.70 (m, 2H), 7.92-7.99 (AA'BB', 2H);
$^{13}$C NMR (75.5 MHz, CDCl$_3$) δ 51.6, 51.9, 52.3, 64.3, 127.0 (2C), 127.1 (2C), 127.4 (2C), 127.6, 128.0, 129.18, 129.22, 129.9, 130.06, 130.09 (3C), 130.3, 130.5, 130.61, 130.64, 130.7, 133.4, 133.7, 134.1, 140.4, 141.3, 146.1, 146.2, 150.8, 166.4;
IR (KBr, cm$^{-1}$) 471, 579, 750, 984, 1018, 1111, 1209, 1281, 1346, 1416, 1514, 1614, 1715, 2949, 3061, 3416;
HRMS (ESI$^+$) m/z 555.2127 ([M+H]$^+$, C$_{33}$H$_{27}$N$_6$O$_3$$^+$ Calcd. 555.2139).

As illustrated in the SPDC reaction of EXAMPLE 18 above, the hetero or unsymmetrical bis-cycloadduct can be obtained as the main product by using the two different azide compounds.

As shown in the results of EXAMPLES above, it is revealed that various azide compounds are applicable to the SPDC reaction. The substituent R in the vicinity of the azido group in azide compounds is modified to various types, whereby the substituent on the triazole ring in the bis-cycloadducts produced can be modified appropriately as shown in formula (1) or (2) described above.

As in the EXAMPLE above, the SPDC reaction proceeds rapidly even under catalyst-free, mild conditions at not very high temperatures. This is considered because the reaction with azide compounds would be promoted by strain of the cyclic diyne compound containing an 8-membered cyclic skeleton and proceed spontaneously. Furthermore, the SPDC reaction is efficient since two azide compounds can be added and ligated to a cyclic diyne in a single step.

On the other hand, when, e.g., an azido group and a triarylphosphine derivative are used to modify a biomolecule or in the case of a single click reaction wherein a single azide compound is added to an alkyne, a plurality of steps are required. This is because it becomes necessary to produce a functional azide compound including fluorescence labeling as a probe and react to add the functional azide compound to a biomolecule each time depending upon the purpose of experimentation.

[Chemical formula (22)]

(22)

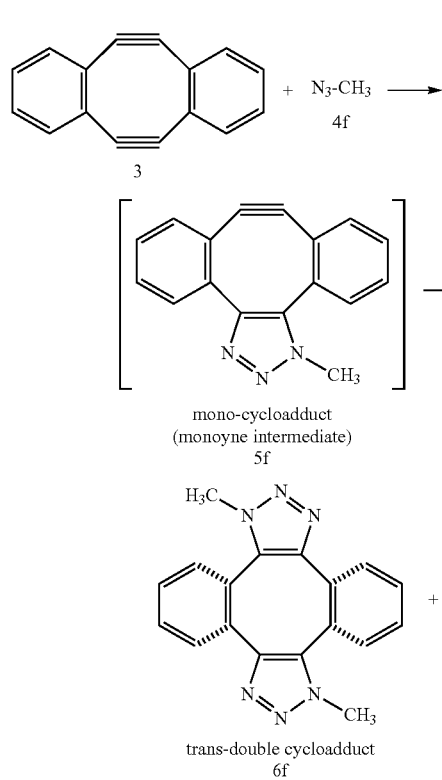

mono-cycloadduct
(monoyne intermediate)
5f trans-double cycloadduct
6f

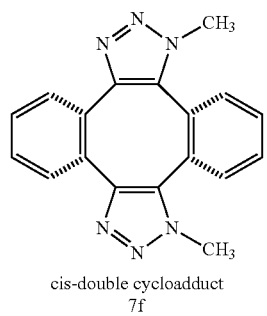

cis-double cycloadduct
7f

In the SPDC reaction of diyne 3 with methyl azide 4f shown by the reaction scheme (22) above, activation energy and transition state were calculated using a density functional theory: DFT [B3LYP/6-31G(d)]. As shown in FIG. 1, the results indicate that energy barriers for cycloaddition of methyl azide 4f to diyne 3 are low and methyl azide 4f is spontaneously reactive with both diyne 3 and monoyne intermediate 5f at room temperature. In particular, the activation energies for a second cycloaddition reaction of monoyne intermediate 5f (+8.8 and +9.5 kcal/mol for trans- and cis-additions, respectively) were smaller than the activation energy for a first cycloaddition reaction of diyne 3 (+12.4 kcal/mol). This indicates that monoyne intermediate 5f has a higher reactivity with methyl azide 4f than diyne 3 does. Therefore, when an addition reaction of two azide compounds proceeds stepwise in the SPDC reaction, a second azido group can also be introduced promptly.

EXAMPLE 19

Comparison in Reactivity Between SPDC Reaction and Conventional Single Click Reaction

[Chemical formula (23)]

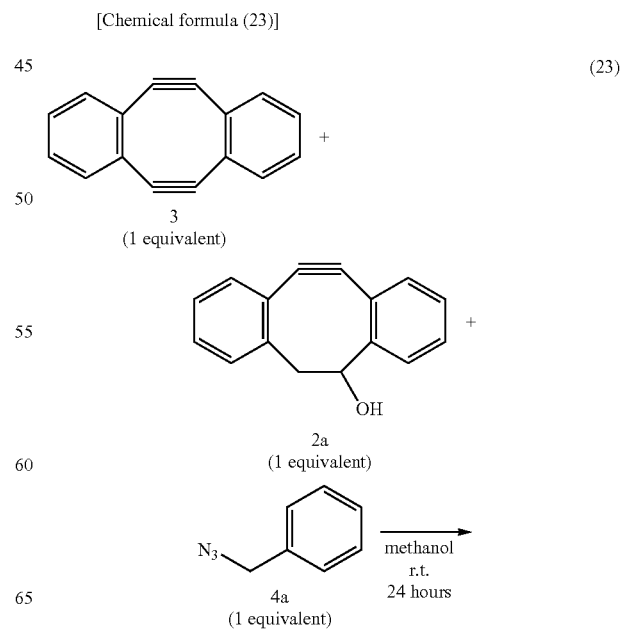

(23)

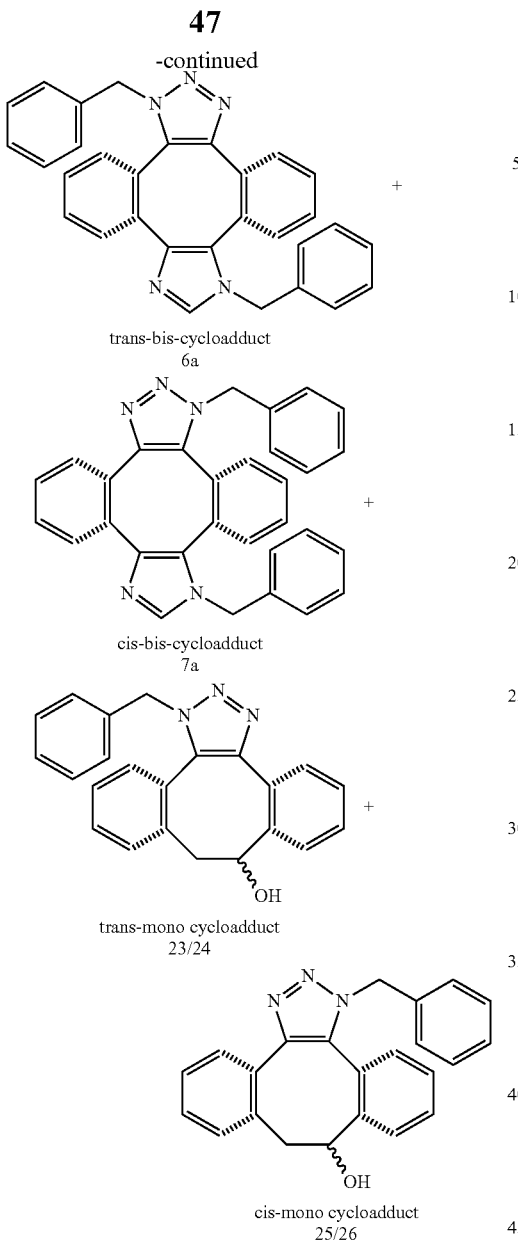

trans-bis-cycloadduct
6a cis-bis-cycloadduct
7a trans-mono cycloadduct
23/24 cis-mono cycloadduct
25/26

To compare the SPDC reaction with a conventional strain-promoted single click reaction, the competition experiment was performed. More specifically, to a mixture of diyne 3 (20.0 mg, 100 μmol) and monoyne 2a (11,12-didehydro-5,6-dihydrodibenzo[a,e]cycloocten-5-ol synthesized by the method described in Non-Patent Document X. Ning, J. Guo. M. A. Wolfert, G.-J. Boons, Angew. Chem. Int. Ed. 2008, 47, 2253-2255) (22.0 mg, 100 μmol) dissolved in methanol (22.5 mL) was added a solution of benzyl azide (4a) (13.3 mg, 100 μmol) in methanol (2.5 mL) at room temperature. After stirring for 24 hours at the same temperature, the reaction solution was concentrated under reduced pressure using an evaporator. The residue was a mixture of two bis-cycloadducts, trans 6a/cis 7a from diyne 3 and mono-cycloadducts 23-26 from monoyne 2a; it was difficult to separate chromatographically or determine the ratio of bis- and mono-cycloadducts by $^1$H NMR as they were. Thus, an oxidant was added to the mixture to convert the mono-cycloadduct alcohols 23-26 from monoyne 2a into the corresponding ketones 27 (trans) and 28 (cis) in the reaction scheme (24) described below to make their analysis easy. Specifically, to a solution of the above residue in chloroform (10 mL) was added Dess-Martin periodinane (37.2 mg, 87.7 μmol) at room temperature. After stirring for 4 hours at the same temperature, the reaction solution was concentrated under reduced pressure using an evaporator. The residue was passed through a short silica-gel column (5 g, ethyl acetate only) to give a mixture of bis-cycloadducts, trans-6a/cis-7a and mono-cycloadduct ketones, trans-27/cis-28. By comparing the integration values of protons on $^1$H NMR spectrum of the mixture, the ratio of 6a/7a to 27/28 was determined to be approximately 1:1. This indicates the similar reactivity of diyne 3 and monoyne 2a toward benzyl azide (4a).

[Chemical formula (24)]

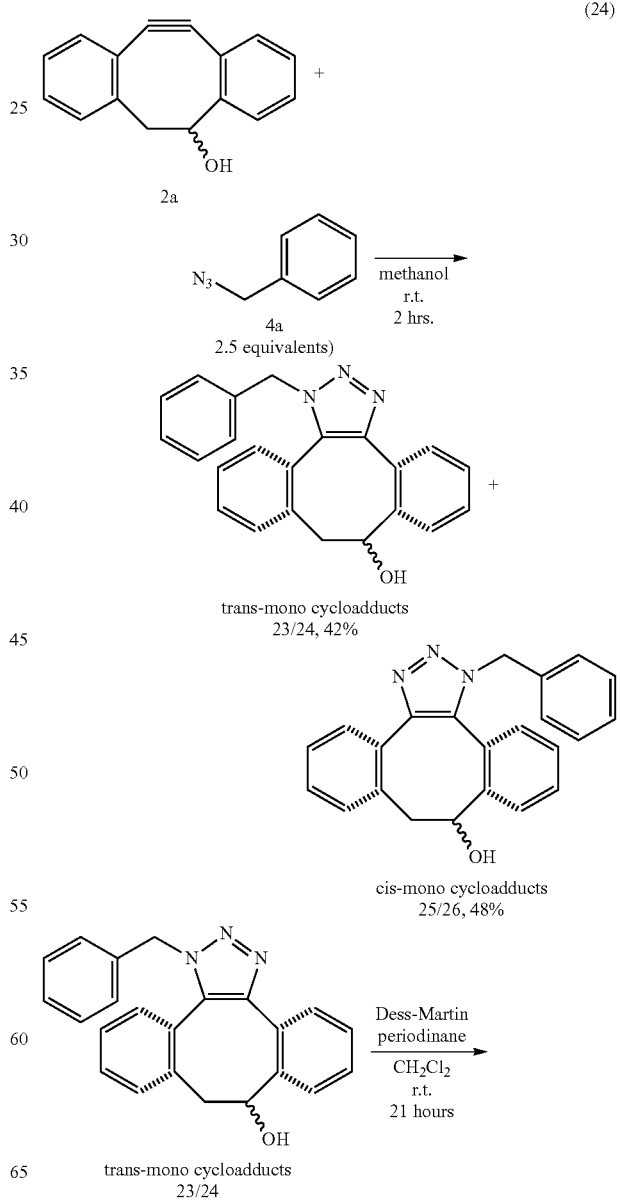

(24)

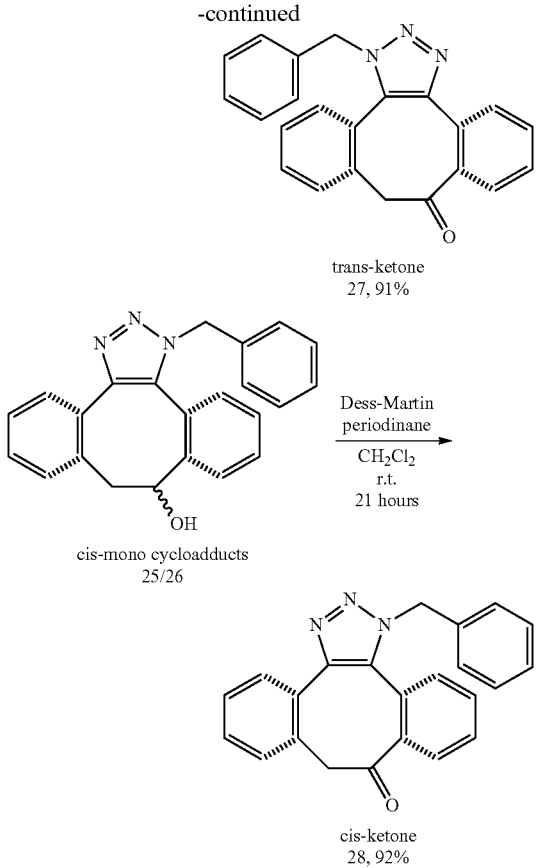

Authentic samples of the ketones 27 (trans) and 28 (cis) produced in EXAMPLE 19 above were synthesized as shown by the reaction scheme (24) above. More specifically, to a solution of monoyne 2a (108 mg, 490 μmol) mop in methanol (11 mL) was added a solution of benzyl azide (4a) (163 mg, 1.22 mmol) in methanol (4 mL) at room temperature. After stirring for 2 hours at the same temperature, the reaction solution was concentrated under reduced pressure using an evaporator. The residue was then purified by flash column chromatography (silica-gel 10 g, dichloromethane/methanol=150/1 to 9/1) to give a mixture of trans-alcohols 23/24 ($R_f$=0.14 (dichloromethane/methanol=49/1)) (72.8 mg, 206 μmol, 42.0% based on the azide (4a)) and a mixture of cis-alcohols 25/26 ($R_f$=0.22 (dichloromethane/methanol=49/1)) (83.0 mg, 235 μmol, 47.9% based on the azide (4a)), among the four regioisomers in the mono-cycloadducts.

To a solution of the mixture of trans-alcohols 23/24 (25.8 mg, 73.0 μmol) in dichloromethane (10 mL) was added Dess-Martin periodinane (37.2 mg, 87.7 μmol) at room temperature. After stirring for 21 hours at the same temperature, the reaction solution was concentrated under reduced pressure using an evaporator. The residue was purified by successive flash column chromatography (silica-gel 10 g, ethyl acetate only, and then silica-gel 10 g, dichloromethane only) to give trans-ketone 27 (23.3 mg, 66.3 mol, 90.8%).

On the other hand, to a solution of the mixture of cis-alcohols 25/26 (22.3 mg, 63.1 μmol) in dichloromethane (10 mL) was likewise added Dess-Martin periodinane (32.1 mg, 75.7 μmol) at room temperature. After stirring for 21 hours at the same temperature, the reaction solution was concentrated under reduced pressure using an evaporator. The residue was purified by successive flash column chromatography (silica-gel 10 g, ethyl acetate only, and then silica-gel 10 g, dichloromethane only) to give cis-ketone 28 (20.5 mg, 58.3 μmol, 92.5%).

The geometries of the respective ketones were confirmed by X-ray crystallographical analyses (CCDC 761157 (27) and CCDC 761156 (28)).

1-Benzyl-1H-dibenzo[3,4:7,8]cycloocta[1,2-d][1,2,3]triazol-8(9H)-one (27)

Recrystallization from n-hexane/ethyl acetate gave colorless crystals. The following physical properties of the crystals were measured to conduct structural analysis.

Mp 220-222° C.;

$R_f$=0.55 (dichloromethane/methanol=9/1);

$^1$H NMR (300 MHz, CDCl$_3$) δ 3.66 (d, 1H, J=12.1 Hz), 3.76 (d, 1H, J=12.1 Hz), 5.57 (d, 1H, J=15.1 Hz), 5.69 (d, 1H, J=15.1 Hz), 7.03-7.10 (m, 2H), 7.23-7.37 (m, 5H), 7.38-7.52 (m, 3H), 7.64 (ddd, 1H, J=1.4, 8.0, 8.0 Hz), 8.01 (dd, 1H, J=1.4, 8.0 Hz), 8.29 (dd, 1H, J=1.4, 8.0 Hz);

$^{13}$C NMR (75.5 MHz, CDCl$_3$) δ 48.0, 52.5, 125.4, 127.2 (2C), 127.5, 128.2, 128.29, 128.34 (3C), 128.8, 129.8, 130.8, 130.9, 131.3, 133.0, 133.2, 133.8, 134.0, 135.0, 146.6, 195.4;

IR (KBr, cm$^{-1}$) 542, 603, 704, 735, 764, 908, 1013, 1150, 1207, 1256, 1279, 1346, 1431, 1454, 1497, 1597, 1668, 3063

1-Benzyl-1H-dibenzo[3,4:7,8]cycloocta[1,2-d][1,2,3]triazol-9(8H)-one (28)

Recrystallization from n-hexane/ethyl acetate gave colorless crystals. The following physical properties of the crystals were measured to conduct structural analysis.

Mp 178-180° C.;

$R_f$=0.67 (dichloromethane/methanol=9/1);

$^1$H NMR (300 MHz, CDCl$_3$) δ 3.60 (br, 1H), 3.81 (br, 1H), 5.67 (d, 2H, J=5.5 Hz), 7.01-7.09 (m, 2H), 7.18 (dd, 1H, J=1.7, 7.7 Hz), 7.24-7.30 (m, 3H), 7.32-7.41 (m, 3H), 7.43-7.56 (m, 2H), 7.66-7.74 (m, 114), 8.15 (dd, 1H, J=1.7, 7.7 Hz);

$^{13}$C NMR (75.5 MHz, CDCl$_3$) δ 49.4, 53.1, 126.3, 127.3 (2C), 127.8, 128.5, 128.7, 128.9 (2C), 129.4, 129.5, 129.6, 130.5, 131.2, 131.4, 132.4, 133.2, 134.5, 134.8, 136.1, 145.8, 196.9;

IR (KBr, cm$^{-1}$) 538, 604, 706, 730, 766, 908, 1028, 1157, 1211, 1250, 1281, 1352, 1429, 1454, 1497, 1597, 1672, 3063

EXAMPLE 20

Kinetic Study for SPDC Reaction

[Chemical formula (25)]

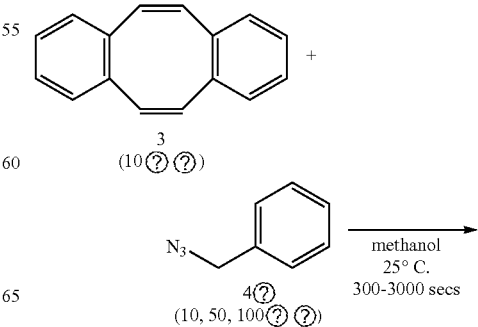

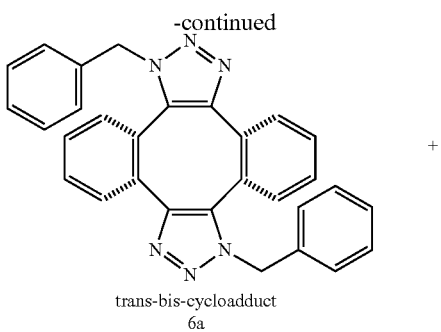

trans-bis-cycloadduct
6a

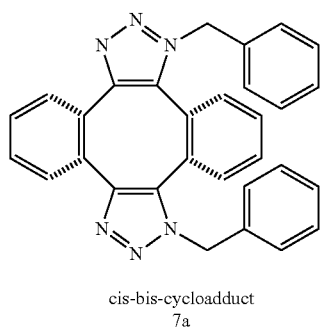

cis-bis-cycloadduct
7a

To compare the difference in reaction rate between the SPDC reaction and the single click reaction more quantitatively, the kinetic study for the SPDC reaction shown by the reaction scheme (25) above was carried out. That is, second order rate constants of the first cycloaddition in the SPDC reaction were monitored by reacting an excess amount of benzyl azide (4a) with diyne 3 and measuring time dependent decreases of the diyne 3.

Figure 2:
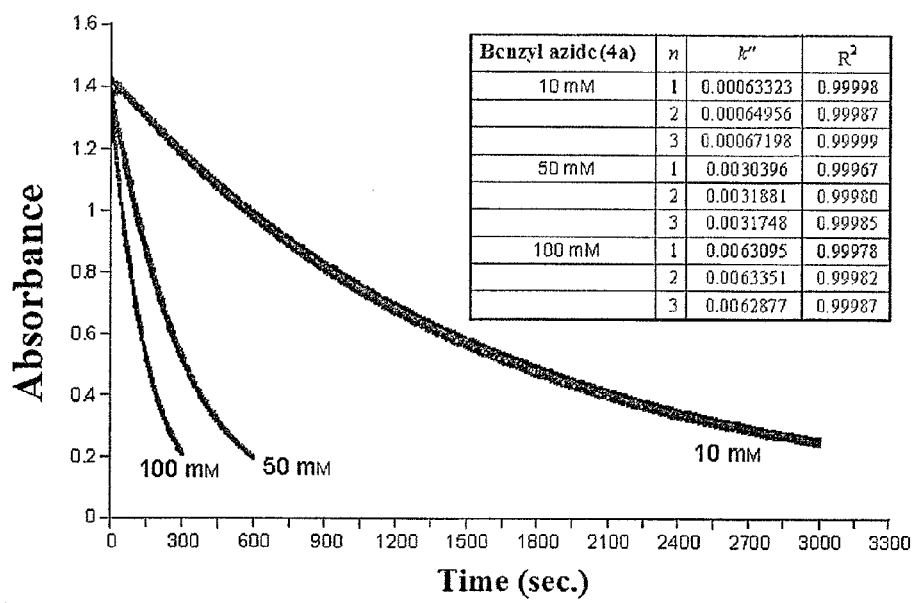
FIG. 2 shows decay curves of the azide compound (benzyl azide) in the SPDC reaction shown by scheme (14).
Figure 3:
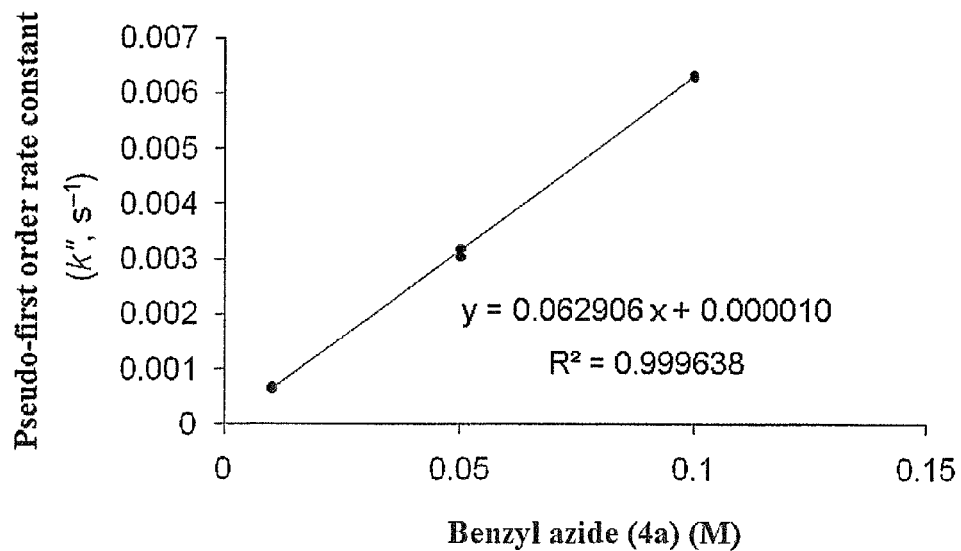
FIG. 3 shows a straight line obtained by plotting the pseudo-first order rate constants versus the azide compound with different concentrations in the SPDC reaction of FIG. 2 (pseudo-first order rate constants in the SPDC reaction).

More specifically, to 1.5 mL of 2.0 mM (fmal concentration at 1.0 mM) solution of diyne 3 in methanol placed in a quartz cuvette of a 10 mm light path, was added 1.5 mL of methanol solution of benzyl azide (4a) in three different concentrations (20, 100 or 200 mM; final concentration at 10, 50 and 100 mM, respectively), while keeping temperature at 25° C. Immediately after initiation of the reaction, the absorbance focusing at 351.5 nm ($\log\epsilon=3.22$), which is an absorption wavelength characteristic of diyne 3, was monitored by UV spectroscopy. For information, almost no significant absorption for benzyl azide (4a) and bis-cycloadducts 6a/7a was observed at 351.5 nm. The monitoring above was continued for 300-3000 seconds and the above measurements were repeated in triplicate for each concentration of benzyl azide (4a) described above. By plotting the absorbance data versus time (second), the exponential decay curves were obtained as shown in FIG. 2. The approximation curves were determined by least-squares fitting using KaleidaGraph (ver. 4.1.1.) to calculate the pseudo-first order rate constants (k"). As such, the pseudo-first order rate constants (k") were plotted versus each concentration of benzyl azide (4a) to give a straight line shown in FIG. 3. A linear regression analysis using Microsoft Office Excel 2007 was conducted and as a result, the slope of this straight line, namely, the second order rate constant for the first cycloaddition in the SPDC reaction, which is the rate-determining step of the SPDC reaction, was found to be $(6.29\pm0.05\ SE)\times10^{-2}\ M^{-1}s^{-1}$.

The second order rate constant of monoyne 2a with benzyl azide (4a) in the single click reaction under the same conditions (25° C. in methanol) is reportedly $(5.67\pm0.27\ SE)\times10^{-2}\ M^{-1}s^{-1}$ (25° C. in methanol) (Non-Patent Document: A. A. Poloukhtine, N. E. Mbua, M. A. Wolfert, G.-J. Boons, V. V. Popik, J. Am. Chem. Soc. 2009, 131, 15769-15776). It was thus shown that both reactions proceed at almost all the same rates also from a kinetic viewpoint.

EXAMPLE 21

Chemical Modification of Azido-biomolecules

Figure 4:
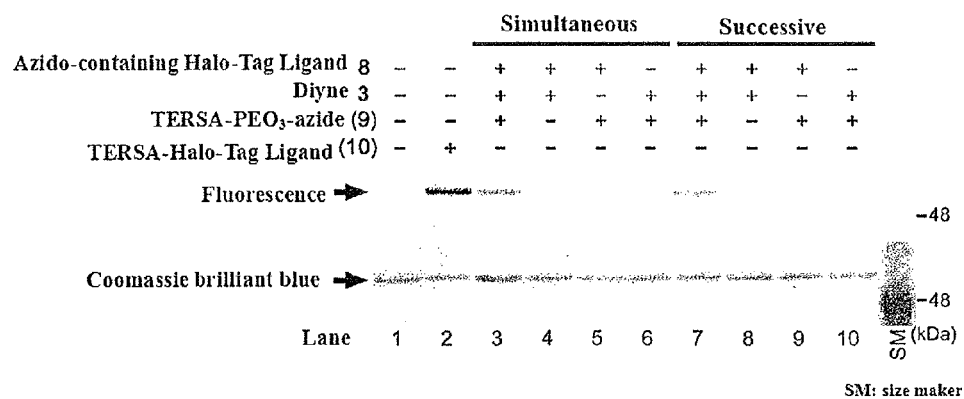
FIG. 4 shows the results of SDS-PAGE analysis of fluorescence-labeled HaloTag proteins by the SPDC reaction using a highly strained diyne and TESRA-PEO$_3$-azide.

Next, EXAMPLE 21 is described for chemical modification of azido-biomolecules by the SPDC reaction. In EXAMPLE 21, expression vector pGEX6P-1-HaloTag capable of expressing the fusion protein GST-HaloTag protein between GST protein and HaloTag protein was first prepared. The expression vector was then transformed into *Escherichia coli*. Expression was induced by the addition of IPTG (isopropyl thiogalactoside) to give the GST-HaloTag protein. The HaloTag-GST protein was purified from the *E. coli* lysate using a GSH-Sepharose resin on which GST is specifically bound. The GST-HaloTag protein thus purified was used for the following chemical modification in the state immobilized onto the GSH-Sepharose resin (hereinafter referred to as HaloTag-Sepharose resin). This HaloTag-Sepharose resin was reacted with HaloTag ligand possessing a long-chain chloroalkane and an azido group (azido-HaloTag ligand) 8 (see formula (26) below) to give the desired azido-HaloTag-Sepharose resin. The fluorescence modification of azido-HaloTag-Sepharose resin was attempted in the SPDC reaction by adding diyne 3 to a solution of the azido-HaloTag-Sepharose resin thus obtained and TESRA-PEO$_3$-azide (9) (an azido-conjugated tetraethylsulforhodamine (TESRA) derivative, cf., formula (26)). After the reaction described above, to the azido-HaloTag-Sepharose resin was first added a SDS-sample buffer containing a reducing agent. The ligation between GST and GSH was cleaved by heating, and the modified GST-HaloTag protein was excised from the resin. These proteins were separated using an acrylamide gel (SDS-PAGE), and then analyzed in a fluorescence imaging analyzer (Typhoon 7600, GE Healthcare) if they were labeled with fluorescence. The GST-HaloTag protein labeled was visualized by staining with Coomassie brilliant blue (CBB). The SDS-PAGE analysis showed a fluorescent band (51 kDa) that corresponds to the TESRA-labeled HaloTag protein in nearly 40% of total labeling efficiency (cf., Lane 3 in FIG. 4). This efficiency was estimated by taking as almost 100% the case where an azido-free HaloTag-Sepharose resin is fluorescence labeled with TESRA-HaloTag ligand (10) (cf., formula (26)). The fluorescence labeling efficiency of azido-free HaloTag-Sepharose resin with TESRA-HaloTag ligand (10) was almost 100%, which was confirmed by MALDI-TOF-MS analysis as described below.

Modification of HaloTag Protein with TESRA-HaloTag Ligand (10)

Figure 5:
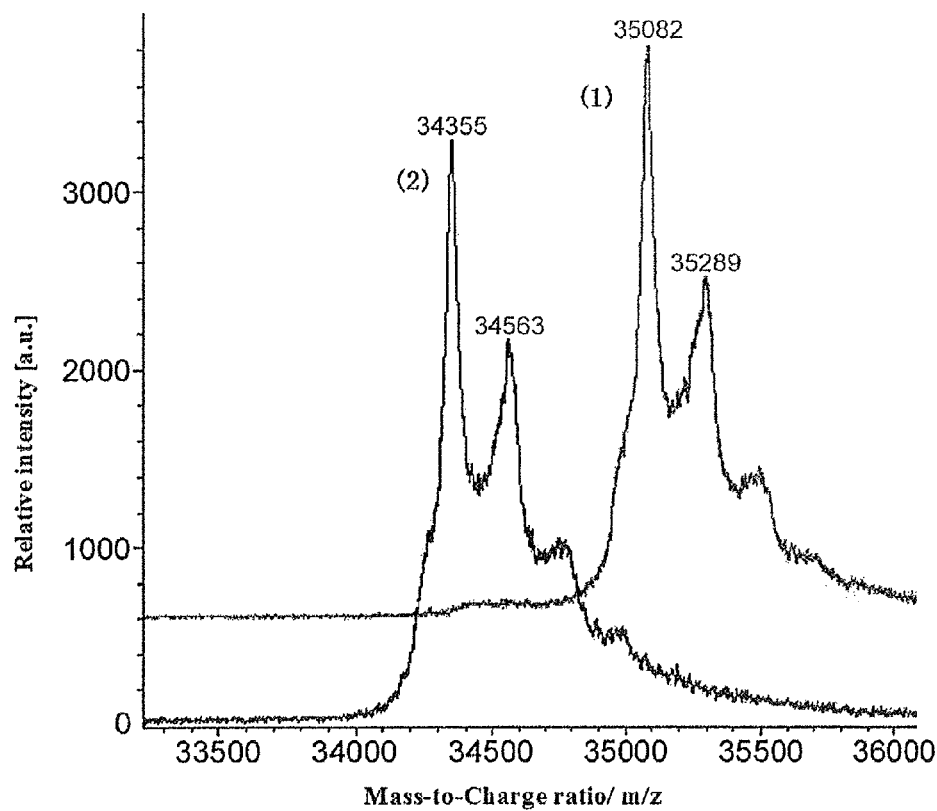
FIG. 5 shows the results of mass spectrometry of fluorescence-labeled HaloTag proteins with TESRA-HaloTag ligand.

First, the azido-free HaloTag-Sepharose resin was modified with the TESRA-HaloTag ligand (10). The modified HaloTag proteins were digested with a protease to elute from the Sepharose resin. The mass of the HaloTag proteins eluted was analyzed by MALDI-TOF-MS (cf., FIG. 5). In FIG. 5 showing the results of the mass spectrometry, line (1) (the peak of relative intensity is 35082 [a.u.]) and line (2) (the peak of relative intensity is 34355 [a.u.]) designate the molecular weight of the HaloTag protein modified with TERSRA-HaloTag ligand (10) and the molecular weight of unmodified HaloTag protein, respectively. As such, almost 100% peak shift was observed by the modification with TESRA-HaloTag ligand (10). The results indicate that the modification efficiency with TESRA-HaloTag ligand (10) is almost 100%.

If any one of the azido-HaloTag ligand 8, diyne 3 and TESRA-PEO$_3$-azide (9) lacks, the GST-HaloTag protein was not fluorescence-labeled. In other words, the fluorescence labeling is a reaction having particularly high specificity that is almost free of non-specific reaction with respect to proteins.

Figure 6:
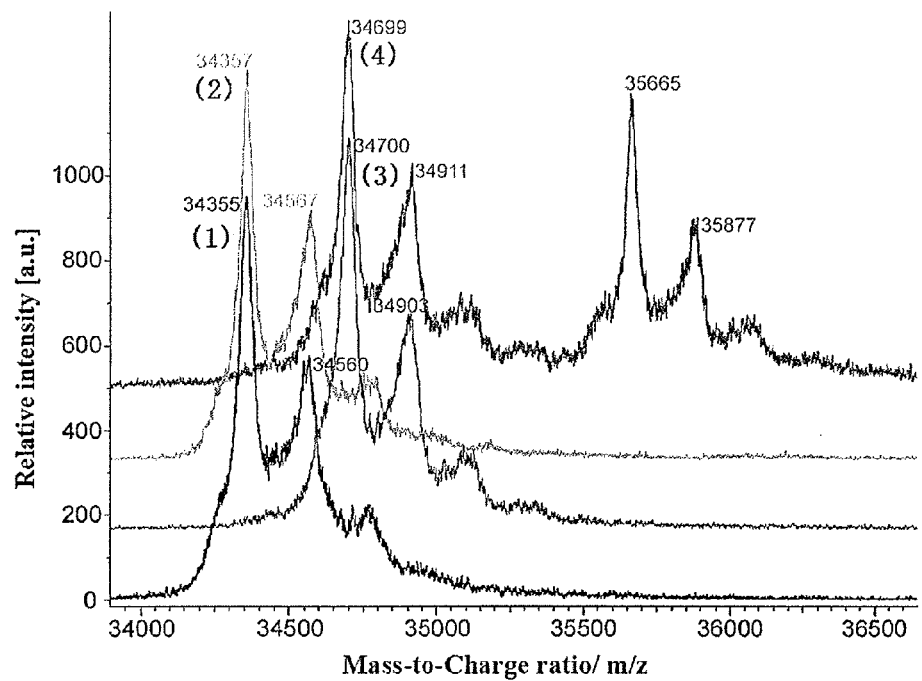
FIG. 6 shows the results of mass spectrometry of fluorescence-modified HaloTag proteins by the SPDC reaction using the highly strained diyne and TESRA-PEO$_3$-azide.

To confirm if the SPDC reaction proceeds as expected, the molecular weight of the azido-HaloTag protein labeled with TESRA by the SPDC reaction described above (EXAMPLE 21) was analyzed by MALDI-TOF-MS. By excising the junction region of GST and HaloTag proteins through limited digestion with a protease, each HaloTag protein was eluted from the GSH-Sepharose resin. The eluate was directly subjected to MALDI-TOF-MS analysis. The results of this mass spectrometry are shown in FIG. 6. In FIG. 6, line (1) (the peak of relative intensity is 34355 [a.u.]) designates the molecular weight of unreacted HaloTag protein and line (2) (the peak of relative intensity is 34357 [a.u.]) designates the molecular weight of azido-free HaloTag proteins obtained by reacting TESRA-PEO$_3$-azide (9) with diyne 3. Also, line (3) (the peak of relative intensity is 34700 [a.u.]) designates the molecular weight of HaloTag protein labeled with azido-HaloTag ligand 8 (azido-HaloTag protein) and line (4) (the peaks of relative intensity are 34699 and 35665 [a.u.]) designates the molecular weights of azido-HaloTag proteins obtained by reacting azido-HaloTag protein with TESRA-PEO$_3$-azide (9) and diyne 3, respectively. Changes in molecular weight of these azido-HaloTag proteins by the SPDC reaction almost matched with the expected change in molecular weight (35643 [a.u.]) by covalent bond of TESRA-PEO$_3$-azide (9) and diyne 3. It was therefore revealed that the SPDC reaction for the azido-HaloTag proteins proceeded smoothly as expected.

[Chemical formula (26)]

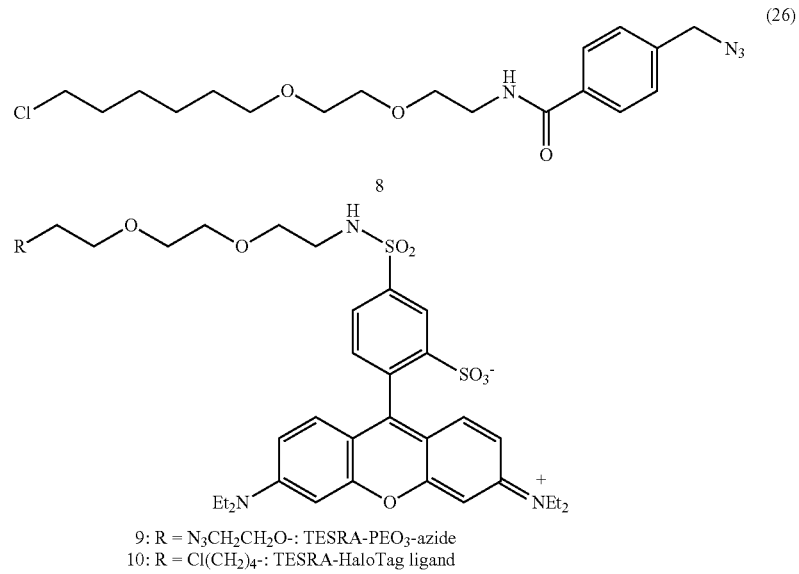

9: R = N$_3$CH$_2$CH$_2$O-: TESRA-PEO$_3$-azide
10: R = Cl(CH$_2$)$_4$-: TESRA-HaloTag ligand In the reaction described above, the reaction was allowed to proceed in a state where the azido-HaloTag protein (azido-HaloTag-Sepharose resin), diyne 3 and fluorescent azide molecule (TESRA-PEO$_3$-azide (9)) were co-present in one test tube (simultaneous SPDC reaction). It is thus difficult to artificially control the progress of the two click reactions in the SPDC reaction. However, the inventors have found that the two click reactions of the SPDC reaction can be controlled. A specific procedure is given below. The azido-HaloTag-Sepharose resin was treated with diyne 3. The unreacted diyne 3 was then quickly washed out by buffer. In this state it is expected that the monoyne intermediate in which the triple bond on one side of diyne 3 is conjugated with the azido-HaloTag-Sepharose would be present. Unexpectedly from the simultaneous SPDC reaction described above, fluorescence labeling of the azido-HaloTag protein was achieved with an efficiency of approximately 45% (cf., FIG. 4, Lane 7) even by sequential procedures of immediately adding TESRA-PEO$_3$-azide (9) in this state (sequential SPDC reaction). That is, it was demonstrated that the monoyne intermediate wherein only one side in diyne 3 was reacted could certainly be present.

Furthermore, in the simultaneous and sequential SPDC reactions described above, the signal for the homo-dimer of the azido-HaloTag protein was hardly detected. These results indicate that the SPDC reaction between azido-proteins does not proceed at least under the conditions examined. This means that formation of the homo-dimer of the azido-protein, which is a relatively large molecule, is almost certainly blocked under the SPDC reaction conditions for the proteins described above, indicating that efficient chemical modification can be achieved. Particularly in the simultaneous SPDC reaction where the azido-HaloTag protein, diyne compound and fluorescent azide molecule are co-present, the azido-HaloTag protein and the fluorescent azide molecule can be added to the diyne compound substantially simultaneously in one step, which makes chemical modification more efficient.

Synthesis of Azido-HaloTag Ligand 8

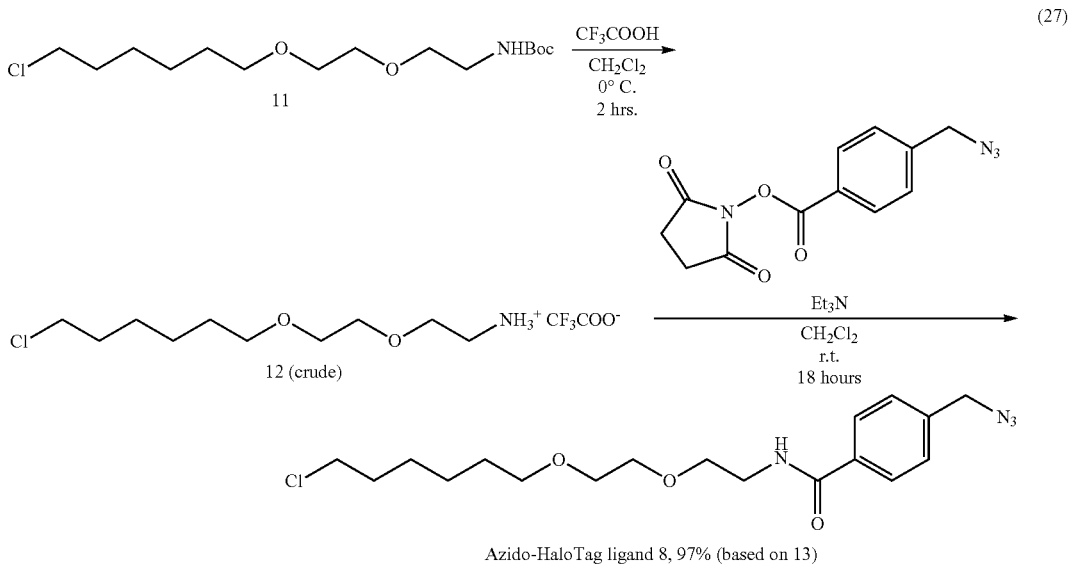

Under argon atmosphere, to a solution of tert-butyl N-[2-{2-(6-chlorohexyloxy)ethoxy}ethyl]carbamate (11) (synthesized by the method described in Non-Patent Document Y. Zhang, M.-k. So, A. M. Loening, H. Yao, S. S. Gambhir, J. Rao, Angew. Chem. Int. Ed., 2006, 118, 4936-4940) (142 mg, 438 μmol) in dichloromethane (3.5 mL) was added trifluoroacetic acid (0.5 mL) at 0° C. After stirring for 2 hours at the same temperature of 0° C., the starting compound 11 completely disappeared as judged from TLC study ($R_f$=0.41, dichloromethane/methanol=9/1). The reaction solution was then concentrated under reduced pressure using an evaporator to give crude 2-[2-(6-chlorohexyloxy)ethoxy]ethylammonium trifluoroacetate (12) as a colorless oil. The product was used in the next step without further purification.

Under argon atmosphere, to a solution of succinimido 4-(azidomethyl)benzoate (13) (synthesized by the method described in Non-Patent Document A. Gopin, S. Ebner, B. Attali, D. Shabat, Bioconjugate Chem. 2006, 17, 1432-1440) (100 mg, 365 μmol) in dichloromethane (2 mL) were successively added triethylamine (153 μL, 1.09 mmol) and and a solution of the crude 12 prepared above at room temperature. After stirring for 18 hours at the same temperature, to the mixture was added water (15 mL) and the product was extracted with dichloromethane (×3). The organic layer was washed with water (×1) and dried over anhydrous sodium sulfate. After filtration, the filtrate was concentrated under reduced pressure using an evaporator and the residue was purified by flash column chromatography (silica-gel 10 g, n-hexane/ethyl acetate=1/1) to give 4-(azidomethyl)-N[2-{2-(6-chlorohexyloxy)ethoxy}ethyl]benzamide 8 (136 mg, 355 μmol, 97.3% based on 13) as a yellow oil.

$R_f$=0.29 (hexane/ethyl acetate=1/1);

$^1$H NMR (300 MHz, CDCl$_3$) δ 1.28-1.50 (m, 4H), 1.51-1.66 (m, 2H), 1.67-1.82 (m, 2H), 3.46 (t, 2H, J=6.7 Hz), 3.52 (t, 2H, J=6.7 Hz), 3.57-3.62 (m, 2H), 3.64-3.71 (m, 6H), 4.40 (s, 2H), 6.75 (br s, 1H), 7.36-7.42 (AA'BB', 2H), 7.79-7.85 (AA'BB', 2H);

$^{13}$C NMR (75.5 MHz, CDCl$_3$) δ 25.3, 26.6, 29.3, 32.4, 39.6, 45.0, 54.1, 69.6, 69.9, 70.1, 71.2, 127.5 (2C), 128.0 (2C), 134.4, 138.7, 166.8;

IR (KBr, cm$^{-1}$) 557, 650, 733, 754, 853, 908, 1018, 1115, 1200, 1252, 1300, 1350, 1456, 1504, 1541, 1614, 1643, 2099, 2862, 2936, 3065, 3331;

HRMS (EI) m/z 382.1775 (M, $C_{18}H_{27}{}^{35}ClN_4O_3$ Calcd. 382.1772).

Synthesis of TESRA-PEO$_3$-azide (9)

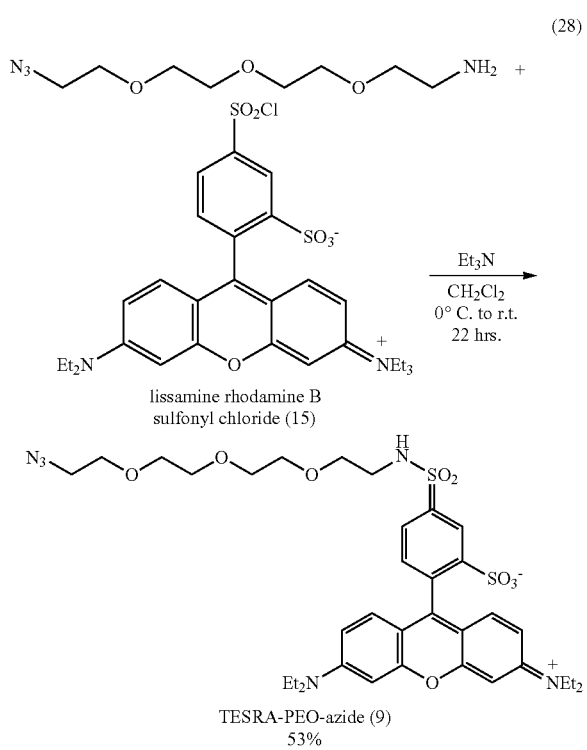

Under argon atmosphere, to a solution of lissamine rhodamine B sulfonyl chloride (15) (synthesized by the method described in Non-Patent Document H. Yang, S. Vasudevan, C. O. Oriakhi, J. Shields, R. G. Carter, Synthesis 2008, 957-961) (600 mg, 1.04 mmol) in dichloromethane (30 mL) were successively added triethylamine (291 µL, 2.08 mmol) and 11-azido-3,6,9-trioxaundecan-1-amine (14, commercial product) (90%) (275 µL, 1.25 mmol) at 0° C. The mixture was allowed to warm to room temperature and stirred for 22 hours. The reaction solution was concentrated under reduced pressure using an evaporator. The residual solid was placed on a Kiriyama funnel and then washed with ethyl acetate. The collected solid was purified by flash column chromatography (silica-gel 50 g, dichloromethane/methanol=19/1) to give TESRA-PEO$_3$-azide (9) (421 mg, 554 µmol, 53.4%) as a purple solid.

$R_f$=0.61 (dichloromethane/methanol=6/1);

$^1$H NMR (300 MHz, DMSO-d$_6$) δ 1.20 (t, 12H, J=7.1 Hz), 3.01 (br s, 2H), 3.32-3.68 (m, 22H), 6.86-7.07 (m, 6H), 7.46 (d, 1H, J=7.7 Hz), 7.94 (d, 1H, J=7.7 Hz), 8.06 (br s, 1H), 8.40 (s, 1H);

IR (KBr, cm$^{-1}$) 613, 683, 1024, 1074, 1134, 1182, 1197, 1248, 1281, 1341, 1352, 1420, 1466, 1526, 1595, 1647;

UV (methanol) λmax (logε) 560.5 nm (5.16);

FL (methanol) λmax Em. 577 nm (Ex. 450 nm);

HRMS (ESI$^+$) m/z 781.2649 ([M+Na]$^+$, C$_{35}$H$_{46}$N$_6$NaO$_9$S$_2{}^+$ Calcd. 781.2660).

Synthesis of TESRA-HaloTag Ligand (10)

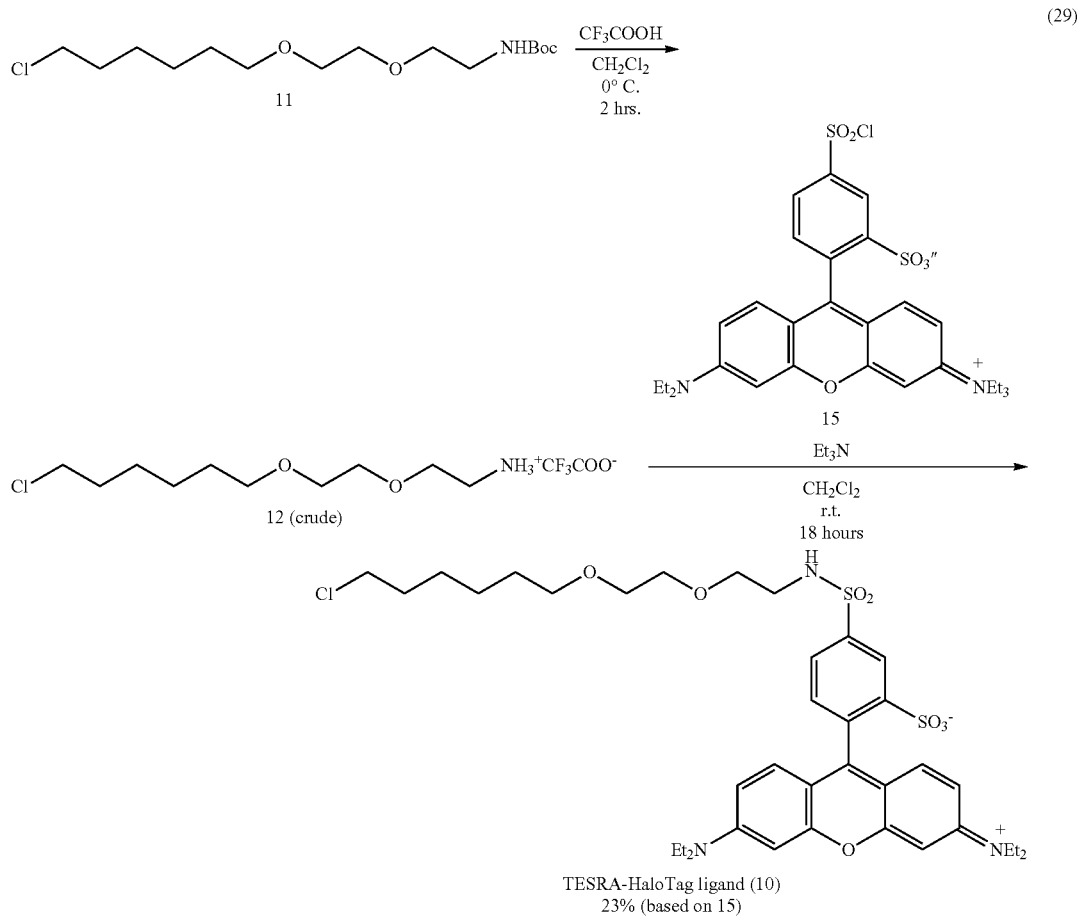

[Chemical formula (29)]

(29)

TESRA-HaloTag ligand (10)
23% (based on 15)

Under argon atmosphere, to a solution of tert-butyl N-[2-{2-(6-chlorohexyloxy)ethoxy}ethyl]carbamate (11) (synthesized by the method described in Non-Patent Document Y. Zhang, M.-k. So, A. M. Loening, H. Yao, S. S. Gambhir, J. Rao, Angew. Chem. Int. Ed., 2006, 118, 4936-4940) (84.2 mg, 260 µmol) in dichloromethane (2.5 mL) was added trifluoroacetic acid (0.5 mL) at 0° C. After stirring for 2 hours at the same temperature of 0° C., the starting compound 11 completely disappeared as judged from TLC study ($R_f$=0.41, dichloromethane/methanol=9/1). The reaction solution was then concentrated under reduced pressure using an evaporator to give crude 2-[2-(6-chlorohexyloxy)ethoxy]ethylammonium trifluoroacetate (12) as a colorless oil. The crude product was used in the next reaction without further purification.

Under argon atmosphere, to a solution of lissamine rhodamine B sulfonyl chloride (15) (100 mg, 173 µmol) in dichloromethane (2 mL) were successively added triethylamine (72.4 µL, 519 µmol) and a solution of the crude product 12 obtained above in dichloromethane (1.5 mL) at room temperature. After stirring for 18 hours at the same temperature, the reaction solution was concentrated under reduced pressure using an evaporator. The residue was purified by flash column chromatography (silica-gel 10 g, dichloromethane/methanol=15/1) to give TESRA-HaloTag ligand (10) (30.1 mg, 39.8 μmol, 22.8% based on 15) as a purple solid.

$R_f$=0.54 (dichloromethane/methanol=6/1);

$^1$H NMR (300 MHz, DMSO-$d_6$) δ 1.20 (t, 12H, J=7.0 Hz), 1.25-1.40 (m, 4H), 1.42-1.52 (m, 2H), 1.62-1.73 (m, 2H), 3.01 (br s, 2H), 3.42-3.51 (m, 8H), 3.55-3.70 (m, 10H), 6.90-7.10 (m, 6H), 7.45 (d, 1H, J=7.7 Hz), 7.94 (d, 1H, J=7.7 Hz), 8.06 (br s, 1H), 8.40 (s, 1H);

IR (KBr, cm$^{-1}$) 579, 683, 1026, 1076, 1136, 1165, 1182, 1202, 1258, 1277, 1350, 1396, 1420, 1466, 1483, 1524, 1597, 1645;

UV (methanol) λmax (logε) 561 nm (5.15);

FL (methanol) λmax Em. 577 nm (Ex. 450 nm);

HRMS (FAB$^+$/NBA) m/z 764.2834 (M+H, $C_{37}H_{51}^{35}ClN_3O_8S_2$ Calcd. 764.2806).

EXAMPLE 22

Fluorescence Labeling of Azido-glycoconjugates on the Surface of Living Cells

Figure 7:
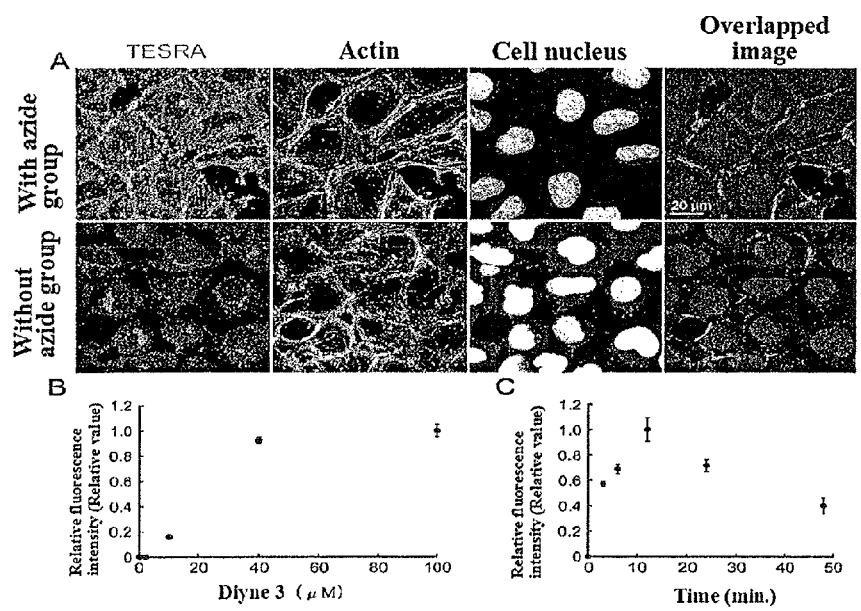
FIG. 7 shows the results of fluorescence labeling test of glycoconjugates at the living cell surface by the SPDC reaction using the highly strained diyne and TESRA-PEO$_3$-azide (modification of cell surface with the diyne and the azide).

To apply chemical modification to living cells by the SPDC reaction further in EXAMPLE 22, fluorescence labeling of azido-glycoconjugates localized on the cell surface was attempted. In EXAMPLE 22, HEK293 cells were cultured for 2 days with a medium containing tetraacetylated N-azidoacetyl-D-mannosamine ($Ac_4ManNAz$) and 10% fetal bovine serum in a final concentration. Thereafter, the serum-containing culture medium was exchanged with fresh medium, and diyne 3 was added thereto. The mixture was allowed to stand at 37° C. for 20 minutes in the presence of 5% carbon dioxide. Immediately thereafter, the mixture was washed with fresh serum-containing culture medium to remove unreacted diyne 3. This procedure was performed to prevent the side reaction that the azide compound only is added to the cyclic diyne compound. Immediately thereafter, TESRA-PEO$_3$-azide (9) (cf., formula (26) above) was added and the mixture was allowed to stand at 37° C. for 20 minutes in the presence of 5% carbon dioxide. To confirm the morphology of cells or the location of nuclei, the cells above were fixed and then further stained with Alexa Fluor 488-labeled phalloidin, which is a reagent for cytoskeleton staining, and a nuclear staining reagent TO-PRO-3. These fluorescence-labeled cells were observed on a laser-scanning confocal microscopy manufactured by Olympus Corporation, and visualized using an Adobe Photoshop CS2 software. As a result, a reliable fluorescence signal was detected in the boundary between the cells where azidosugars are incorporated into glycoconjugates on the cell surface (cf., the superimposed images in FIG. 7A, upper right corner). In contrast, in the cells where azidosugars are not incorporated into glycoconjugates on the cell surface (cf., buffer (−) in FIG. 7A, lower side), only a trace of fluorescence signal was barely detected at almost a negligible level. It is thus revealed that fluorescence labeling of the cell surface can be achieved only in the presence of azido-glycoconjugates and non-specific modification to cells was hardly observed.

In the fluorescence labeling test system for the azido-glycoconjugates in the HEK293 cells described above, the optimum results were obtained when diyne 3 was used at concentrations of 40 to 100 μM. It was thus confirmed that the labeling efficiency with diyne 3 was dependent on concentration (cf., FIG. 7B). To determine the fluorescence labeling efficiency, intensities of the fluorescence images obtained were digitalized using an Image-J software and represented graphically using averaged values. Standard error at each point is shown as well.

On the other hand, to optimize the reaction time of diyne 3, 40 μM of diyne 3 was added to the serum-containing culture medium of HEK293 cells with azido-glycoconjugates, and the mixture was allowed to stand for 0 to 48 minutes. Thereafter, fluorescence labeling was performed using TESRA-PEO$_3$-azide (9) as described above. The fluorescence images obtained were quantified by the procedure described above and represented graphically. The results reveal that the efficiency became maximum in the reaction time for approximately 20 minutes but the efficiency decreased in the reaction time exceeding 20 minutes (cf., FIG. 7C). This decrease in the labeling efficiency due to the passage of time shows instability of the monoyne intermediate that only one side of diyne 3 has reacted with an azido group and is considered to be because the monoyne intermediate is degraded with the passage of time.

Figure 8:
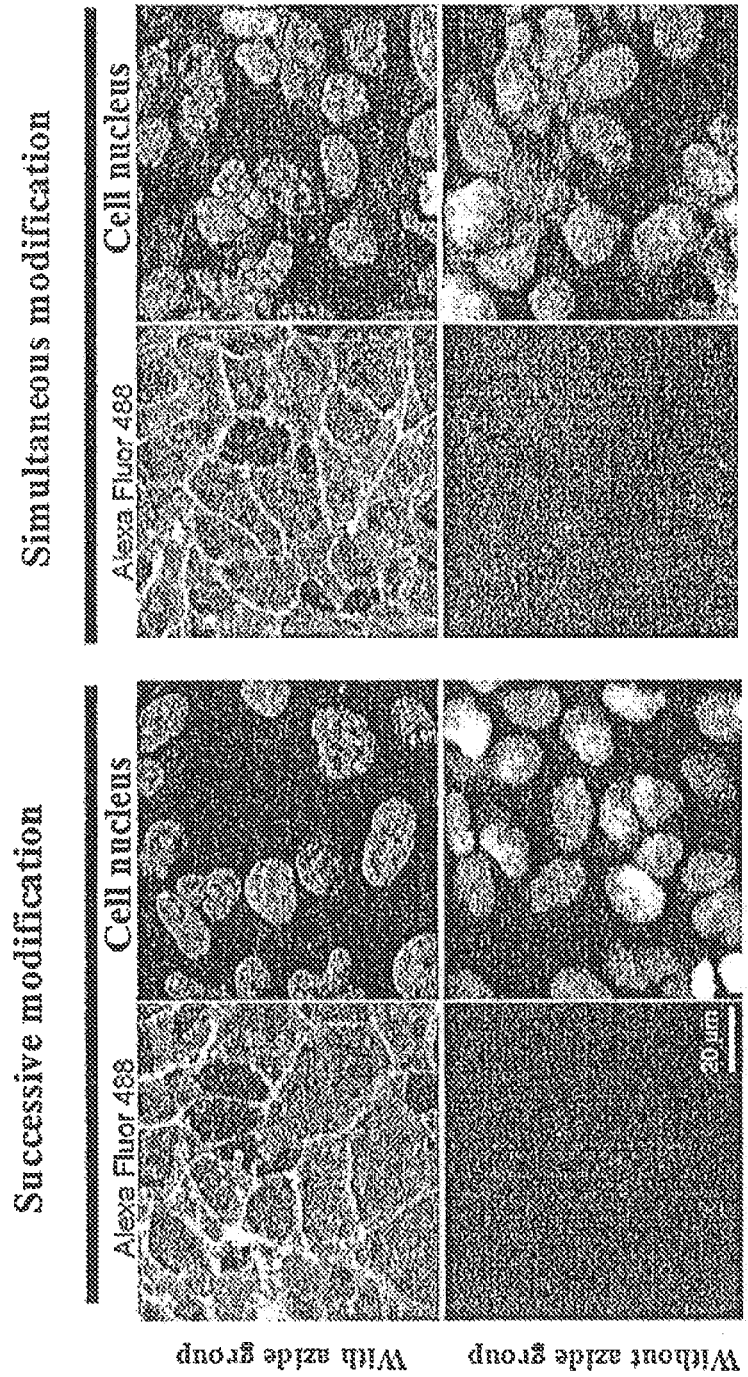
FIG. 8 shows the results of fluorescence labeling test of glycoconjugates on the surface of living cells by the SPDC reaction using a highly strained diyne and Alexa Fluor 488 azide.

In order to study if not only the TESRA-PEO$_3$-azide (9) independently synthesized by the inventors but also low molecular azide compounds commercially available can be used for the SPDC reaction, fluorescence labeling tests were conducted on HEK293 cells with azido-glycoconjugates, using commercially available Alexa Fluor 488 azide. As a result, fluorescence labeling could be efficiently achieved as well not only by the sequential procedures described above but also by the simultaneous procedures of adding diyne 3 and Alexa Fluor 488 azide to the cell culture medium as shown in FIG. 8. FIG. 8 shows the surface of HEK293 cells (azido-incorporated) labeled with Alexa Fluor 488 azide and cell nuclei, and the surface of unlabeled cells and cell nuclei (azido-free), respectively. The foregoing results indicate that there is no big limitation to low molecular azide compounds used for chemical modification but diverse low molecular azide compounds may be used.

Figure 9:
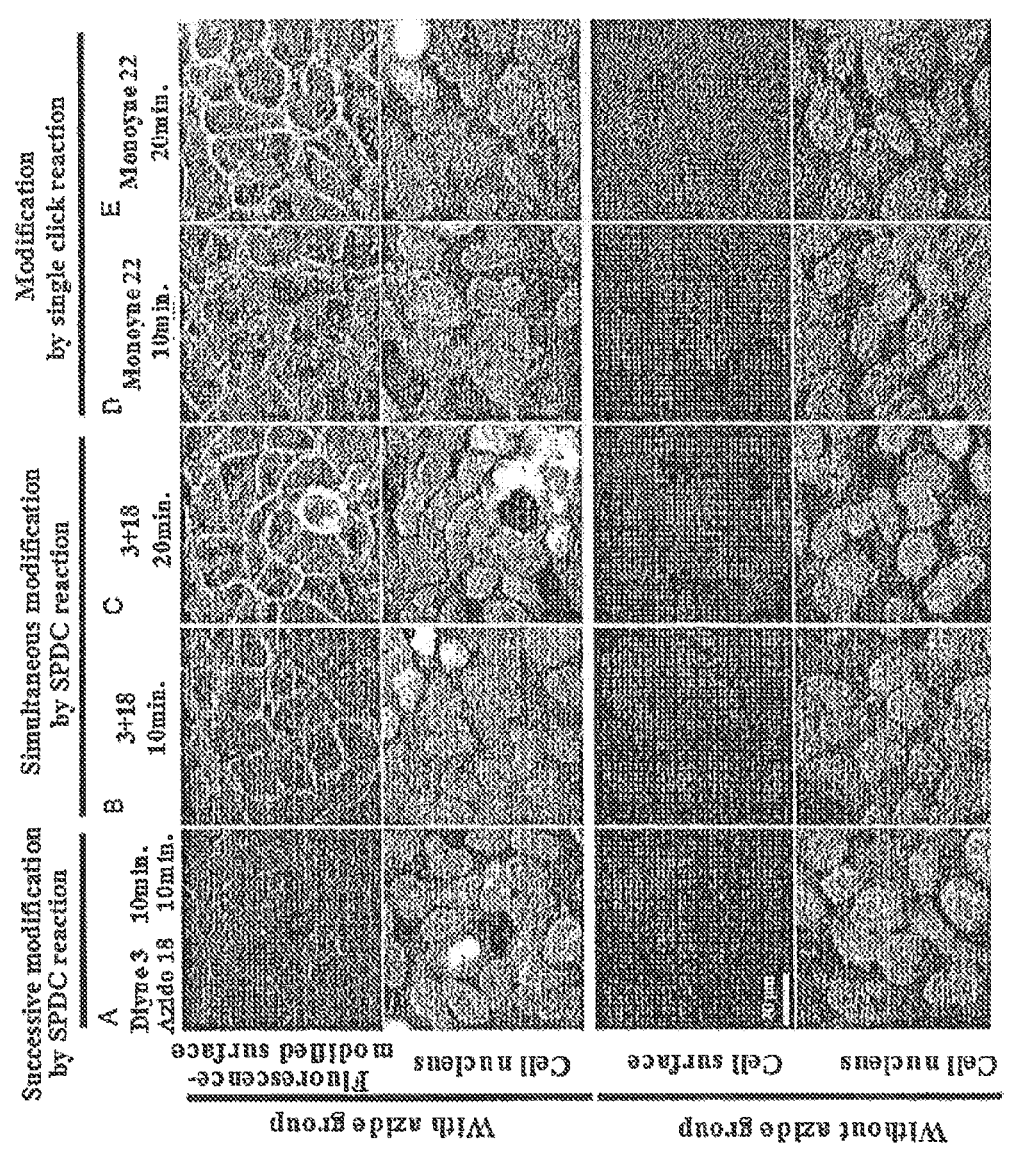

Furthermore, the inventors made comparative studies between the modification by the SPDC reaction and the modification by the single click reaction using the existing monoyne fluorescence derivatives. The results are shown in FIG. 9. Herein, fluorescence labeling was performed for the azidosugar-incorporated HEK293 cells (azido-incorporated) and azidosugar-not incorporated HEK293 cells (azido-free), respectively, by the SPDC reaction using diyne 3 and fluorescein-conjugated azide 18 and by the single click reaction using monoyne 22 (cf., reaction scheme 31) which is a fluorescence derivative of monoyne 2a. The SPDC reaction was carried out in two types of reactions by simultaneous and sequential procedures. The respective reaction times are shown in the figure. As a result of the comparative test, substantial difference in fluorescence labeling efficiency between the SPDC reaction and the single click reaction was hardly observed at the same reaction time. The results showed a good match with the competition experiment demonstrated in EXAMPLE 19 and the results of the kinetic study shown in EXAMPLE 20 (cf., the corresponding paragraphs above and FIGS. 2 and 3). That is, it was demonstrated that the SPDC modification reaction using the fluorescein-conjugated azide 18 for diyne 3 and fluorescein-conjugated monoyne 22 described above to monoyne 2a proceeded at almost the same rate.

[Chemical formula (30)]

[Chemical formula (31)]

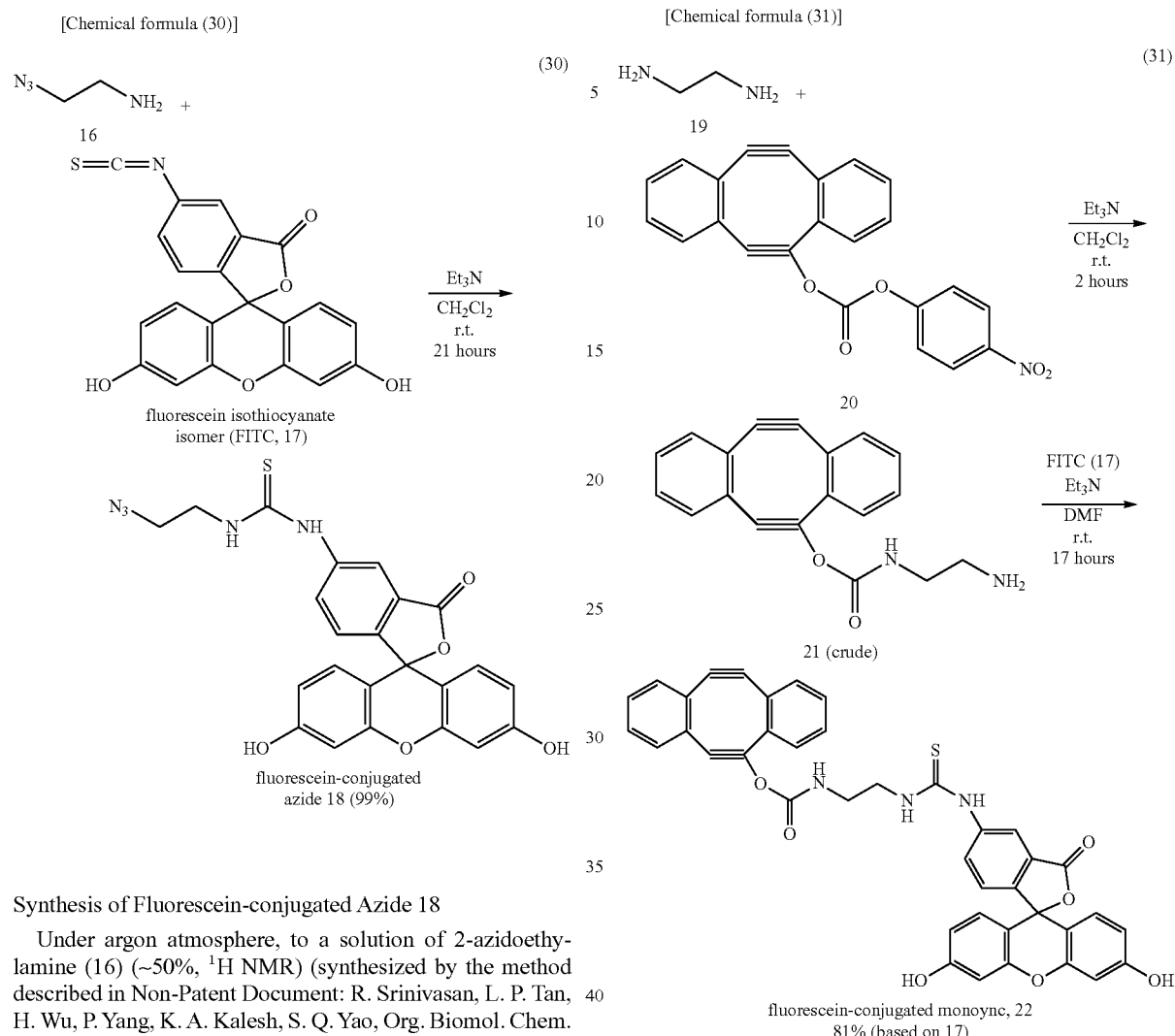

fluorescein isothiocyanate isomer (FITC, 17)

fluorescein-conjugated azide 18 (99%)

fluorescein-conjugated monoyne, 22
81% (based on 17)

Synthesis of Fluorescein-conjugated Azide 18

Under argon atmosphere, to a solution of 2-azidoethylamine (16) (~50%, $^1$H NMR) (synthesized by the method described in Non-Patent Document: R. Srinivasan, L. P. Tan, H. Wu, P. Yang, K. A. Kalesh, S. Q. Yao, Org. Biomol. Chem. 2009, 7, 1821-1828) (200 mg, ~1.16 mmol) in dichloromethane (5 mL) were successively added triethylamine (70.0 µL, 502 µmol) and fluorescein isothiocyanate isomer I (FITC, 17, commercial product) (90%, HPLC) (100 mg, 231 µmol) at room temperature. After stirring for 21 hours at the same temperature, the reaction solution was concentrated under reduced pressure using an evaporator. The residue was purified by flash column chromatography (silica-gel 30 g, dichloromethane/methanol=9/1) to give 1-(2-azidoethyl)-3-(5-fluoresceinyl)thiourea (18) (109 mg, 229 µmol, 99.2%) as an orange solid.

TLC $R_f$=0.61 (dichloromethane/methanol=6/1);

$^1$H NMR (300 MHz, DMSO-$d_6$) δ 2.73 (t, 2H, J=5.8 Hz), 3.56 (t, 2H, J=5.8 Hz), 3.65-3.80 (br, 2H), 6.54 (dd, 2H, J=2.2, 8.6 Hz), 6.61 (d, 2H, J=8.6 Hz), 6.65 (d, 2H, J=2.2 Hz), 7.18 (d, 1H, J=8.4 Hz), 7,72 (dd, 1H, J=1.7, 8.4 Hz), 8.21 (d, 1H, J=1.7 Hz), 8.25-8.40 (br, 1H), 9.80-10.60 (br, 1H);

IR (KBr, cm$^{-1}$) 459, 476, 577, 600, 667, 812, 851, 914, 1111, 1173, 1207, 1296, 1389, 1458, 1570, 2108, 2930;

UV (methanol) λmax (logε) 456 nm (4.07), 482 nm (4.09);

FL (methanol) λmax Em. 516.5 nm (Ex. 450 nm);

HRMS (ESI$^+$) m/z 476.1024 ([M+H]$^+$, $C_{23}H_{18}N_5O_5S^+$ required 476.1023).

Synthesis of Fluorescein-conjugated Monoyne 22

Under argon atmosphere, to a solution of ethylenediamine (19) (320 µL, 479 µmol) in dichloromethane (5 mL) were successively added triethylamine (330 µL, 237 µmol) and 11,12-didehydro-5,6-dihydrodibenzo[a,e]cycloocten-5-yl 4-nitrophenyl carbonate (20) (synthesized by the method described in Non-Patent Document X. Ning, J. Guo. M. A. Wolfert, G-J. Boons, Angew. Chem. Int. Ed. 2008, 47, 2253-2255) (60.3 mg, 156 µmol) at room temperature. After stirring for 2 hours at the same temperature, the starting compound 20 completely disappeared as judged from the TLC study. To the reaction solution was added dichloromethane (70 mL) and the mixture was washed with saturated aqueous sodium hydrogen carbonate solution (20 mL×7), dried over anhydrous sodium sulfate and filtered. The filtrate was concentrated under reduced pressure using an evaporator to give crude 11,12-didehydro-5,6-dihydrodibenzo[a,e]cycloocten-5-yl N-(2-azidoethyl)carbamate (21) (51.2 mg) as a pale yellow oil, which was used in the next step without further purification.

Under argon atmosphere, to a solution of the crude 21 obtain as above in DMF (3 mL) were successively added triethylamine (29.0 µL, 208 µmol) and fluorescein isothiocyanate isomer I (FITC, 17, commercial product) (90%, HPLC)

(45.0 mg, 104 μmol) at room temperature. After stirring for 17 hours at the same temperature, the reaction solution was concentrated under reduced pressure. The residue was purified by flash column chromatography (silica-gel 8 g, dichloromethane/methanol=12/1) to give 1-[2-{(11,12-didehydro-5,6-dihydrodibenzo[a,e]cycloocten-5-yl)oxycarbonylamino}ethyl]-3-(5-fluoresceinyl)thiourea (22) (59.0 mg, 84.8 μmol, 80.7% based on 17) as a yellow solid. TLC $R_f$=0.52 (dichloromethane/methanol=6/1);
$^1$H NMR (300 Mz, CD$_3$OD) δ 2.73 (dd, 1H, J=3.7, 14.9 Hz), 3.20 (dd, 1H, J=2.4, 14.9 Hz), 3.70-3.80 (m, 2H), 5.28 (s, 1H), 6.41 (dd, 2H, J=2.3, 9.2 Hz), 6.59 (dd, 2H, J=2.3, 9.2 Hz), 6.70 (d, 1H, J=2.3 Hz), 6.71 (d, 1H, J=2.3 Hz), 6.97-7.56 (m, 12H), 7.83 (s, 1H);
IR (KBr, cm$^{-1}$) 488, 546, 565, 578, 760, 851, 914, 993, 1022, 1076, 1113, 1179, 1207, 1258, 1317, 1449, 1506, 1595, 1701, 2938, 3063, 3287;
UV (methanol) λmax (logε) 455 nm (3.95), 481 nm (3.95);
FL (methanol) λmax Em. 515 nm (Ex. 450 nm);
HRMS (ESI$^+$) m/z 696.1785 ([M+H]$^+$, C$_{40}$H$_{30}$N$_3$O$_7$S$^+$ required 696.1799).

Figure 10:
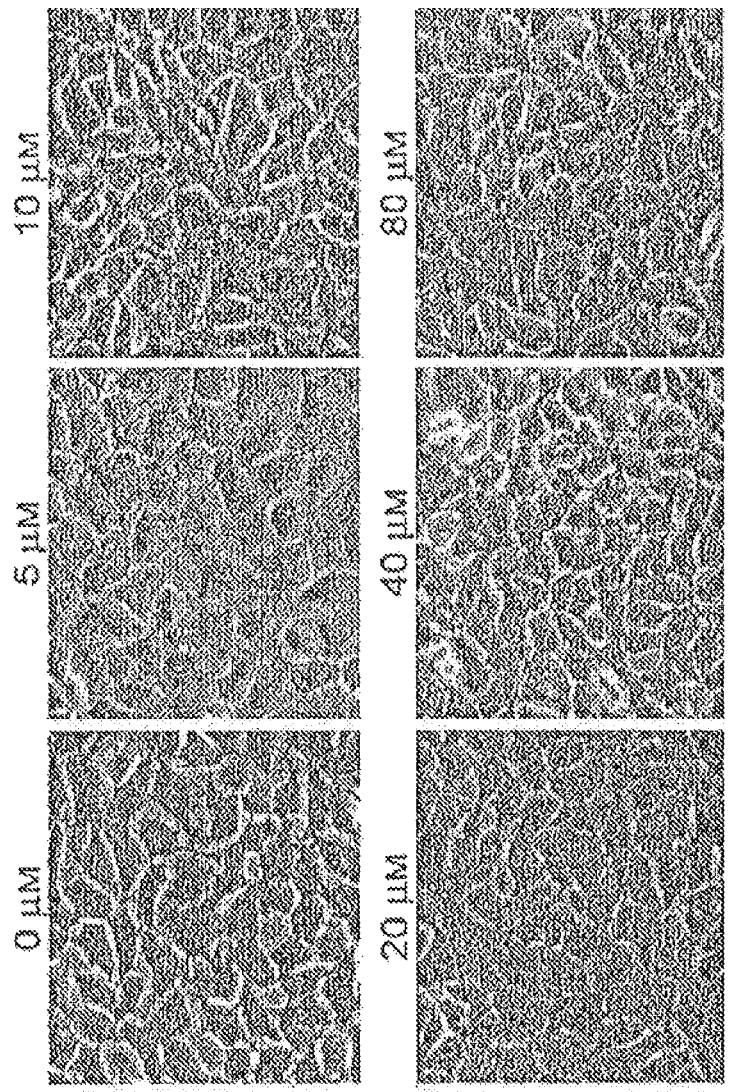
FIG. 10 shows the results of cytotoxicity assay of the highly strained diyne used in the SPDC reaction.

Finally, cytotoxicity assay of diyne 3 was performed in living cells. HEK293 cells were incubated and diyne 3 was added to the cells in a concentration of 0 to 80 μM, followed by incubation overnight. Morphological images of the cells after incubation, which were taken under a phase-contrast microscope and visualized with Adobe Photoshop CS2, are shown in FIG. 10. The results indicate that diyne 3 did not show cytotoxicity and is applicable to chemical modification of living cells as well.

As demonstrated above, it was revealed that diyne 3 is useful as a substrate in the modification of azido-biomolecules with the functional azide compound having a fluorescent functional group, etc. as a probe, taking advantage of the SPDC reaction. In particular, diyne 3 (or cyclic diyne compounds having similar structures) and a variety of functional azido-compounds are readily available or can be easily synthesized. Thus, various functional biomolecules can be prepared by applying the SPDC reaction. Furthermore, two azide compounds can be added and ligated in a single step and by utilizing the SPDC reaction which rapidly proceeds even under catalyst-free, mild conditions, functional biomolecules can be prepared easily and efficiently even in living cells, etc. while maintaining their functions.

The invention claimed is:

1. A method for producing a cyclic compound, which comprises adding and ligating an azide compound having an azido group to each of the two carbon-carbon triple bond sites on the cyclic skeleton in a cyclic diyne compound by a double click reaction to produce a cyclic compound comprising two triazole rings.

2. The method according to claim 1, wherein the cyclic compound comprises the cyclic skeleton of an 8-membered ring.

3. The method according to claim 1, wherein the cyclic compound further comprises a benzene ring and/or heteroaromatic ring sharing the carbon-carbon double bond sites with the cyclic skeleton.

4. The method according to claim 2, wherein the cyclic compound further comprises a benzene ring and/or heteroaromatic ring sharing the carbon-carbon double bond sites with the cyclic skeleton.

5. The method according to claim 1, wherein the cyclic compound is represented by formula (1) or (2) below:

[Chemical formula (1)]

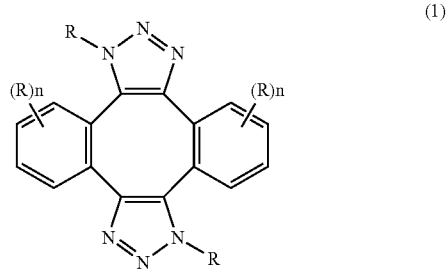

(1)

in formula (1), each R independently represents hydrogen or a hydrocarbon group, and each n independently represents an integer of 0 to 4, and,

[Chemical formula (2)]

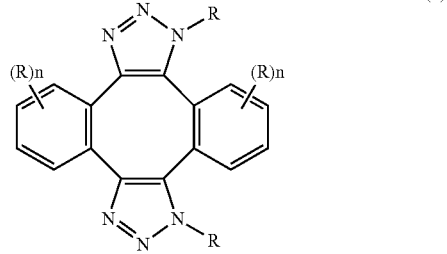

(2)

in formula (2), each R independently represents hydrogen or a hydrocarbon group, and each n independently represents an integer of 0 to 4.

* * * * *